US008247201B2

(12) United States Patent
Tajima et al.

(10) Patent No.: US 8,247,201 B2
(45) Date of Patent: Aug. 21, 2012

(54) METHOD FOR PRODUCING AN ORGANIC ACID

(75) Inventors: Yoshinori Tajima, Kawasaki (JP); Keita Fukui, Kawasaki (JP); Kenichi Hashiguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 22 days.

(21) Appl. No.: 12/793,107

(22) Filed: Jun. 3, 2010

(65) Prior Publication Data

US 2010/0297716 A1 Nov. 25, 2010

Related U.S. Application Data

(63) Continuation of application No. PCT/JP2008/072055, filed on Dec. 4, 2008.

(30) Foreign Application Priority Data

Dec. 6, 2007 (JP) .................................. 2007-315764

(51) Int. Cl.
*C12P 7/46* (2006.01)
*C12N 9/00* (2006.01)
*C12N 15/00* (2006.01)
*C07H 21/04* (2006.01)

(52) U.S. Cl. ...................... 435/145; 435/183; 435/320.1; 536/23.2

(58) Field of Classification Search .................. None
See application file for complete search history.

(56) References Cited

U.S. PATENT DOCUMENTS

| | | | |
|---|---|---|---|
| 5,142,834 | A | 9/1992 | Laclave et al. |
| 5,143,833 | A | 9/1992 | Datta |
| 5,504,004 | A | 4/1996 | Guettler et al. |
| 2005/0170482 | A1 | 8/2005 | San et al. |
| 2006/0073577 | A1 | 4/2006 | Ka-Yiu et al. |
| 2007/0154999 | A1* | 7/2007 | Fukui et al. .................. 435/145 |
| 2007/0254345 | A1 | 11/2007 | Fukui et al. |
| 2009/0239269 | A1 | 9/2009 | Tajima et al. |
| 2010/0068774 | A1 | 3/2010 | Fukui et al. |
| 2010/0081180 | A1 | 4/2010 | Fukui et al. |
| 2010/0112647 | A1 | 5/2010 | Hara et al. |

FOREIGN PATENT DOCUMENTS

| | | |
|---|---|---|
| JP | 11-113588 | 4/1999 |
| JP | 11-196887 | 7/1999 |
| JP | 11-196888 | 7/1999 |
| JP | 2006-180782 | 7/2006 |
| WO | WO2005/113745 | 12/2005 |
| WO | WO2005/116227 | 12/2005 |
| WO | WO2006/034156 | 3/2006 |
| WO | WO2009/072562 | 11/2009 |

OTHER PUBLICATIONS

Accession A6VKV4. Aug. 21, 2007.*
Chica et al. Curr Opin Biotechnol. Aug. 2005;16(4):378-84.*
Sen et al. Appl Biochem Biotechnol. Dec. 2007;143(3):212-23.*
International Preliminary Report on Patentability for PCT Patent App. No. PCT/JP2008/072055 (Aug. 19, 2010).
Ito, T., et al., "High-Yield Production of Hydrogen by *Enterobacter aerogenes* Mutants with Decreased α-Acetolactate Synthase Activity," J. Biosci. Bioeng. 2004;97(4):227-232.
Sánchez, A. M., et al., "Efficient Succinic Acid Production from Glucose through Overexpression of Pyruvate Carboxylase in an *Escherichia coli* Alcohol Dehydrogenase and Lactate Dehydrogenase Mutant," Biotechnol. Prog. 2005;21:358-365.
Wu, H., et al., "Improved Succinic Acid Production in the Anaerobic Culture of an *Escherichia coli pflB ldhA* Double Mutant as a Result of Enhanced Anaplerotic Activities in the Preceding Aerobic Culture," Appl. Environmen. Microbiol. 2007;73(24):7837-7843.
International Search Report for PCT Patent App. No. PCT/JP2008/072055 (Jan. 13, 2009).
Asanuma, N., et al., "Molecular characterization, enzyme properties and transcriptional regulation of phosphoenolpyruvate carboxykinase and pyruvate kinase in a ruminal bacterium, *Selenomonas ruminantium*," Microbiology 2001;147:681-690.
Chao, Y-P., et al., "Alteration of Growth Yield by Overexpression of Phosphoenolpyruvate Carboxylase and Phosphoenolpyruvate Carboxykinase in *Escherichia coli*," Appl. Environmen. Microbiol. 1993;59(12):4261-4265.
Guettler, M. V., et al., "*Actinobacillus succinogenes* sp. nov., a novel succinic-acid-producing strain from the bovine rumen," Int. J. Sys. Bacteriol. 1999;49:207-216.
Ito, T., et al., "Hydrogen and Ethanol Production from Glycerol-Containing Wastes Discharged after Biodiesel Manufacturing Process," J. Biosci. Bioeng. 2005;100(3):260-265.
Kim, P., et al., "Effect of Overexpression of *Actinobacillus succinogenes* Phosphoenolpyruvate Carboxykinase on Succinate Production in *Escherichia coli*," Appl. Environmen. Microbiol. 2004;70(2):1238-1241.
Laivenieks, M., et al., "Cloning, Sequencing, and Overexpression of the *Anaerobiospirillum succiniciproducens* Phosphoenolpyruvate Carboxykinase (*pckA*) Gene," Appl. Environmen. Microbiol. 1997;63(6):2273-2280.
Lee, S. J., et al, "Genome-Based Metabolic Engineering of *Mannheimia succiniciproducens* for Succinic Acid Production," Appl. Environmen. Microbiol. 2006;72(3):1939-1948.
Millard, C. S., et al., "Enhanced Production of Succinic Acid by Overexpression of Phosphoenolpyruvate Carboxylase in *Escherichia coli*," Appl. Environmen. Microbiol. 1996;62(5):1808-1810.
Vemuri, G. N., et al., "Succinate production in dual-phase *Escherichia coli* fermentations depends on the time of transition from aerobic to anaerobic conditions," J. Ind. Microbiol. Biotechnol. 2002;28:325-332.
Supplementary European Search Report for European Patent App. No. 08857657.4 (Dec. 7, 2011).

* cited by examiner

*Primary Examiner* — Christian Fronda

(74) *Attorney, Agent, or Firm* — Shelly Guest Cermak; Cermak Nakajima LLP

(57) ABSTRACT

An organic acid is produced by allowing a bacterium belonging to the family Enterobacteriaceae, which has an ability to produce an organic acid and has been modified so that the phosphoenolpyruvate carboxykinase activity is enhanced, which is selected from *Enterobacter, Pantoea, Erwinia, Klebsiella* and *Raoultella* bacteria, or a product obtained by processing the bacterium, to act on an organic raw material in a reaction mixture containing carbonate ions, bicarbonate ions, or carbon dioxide gas to produce the organic acid, and collecting the organic acid.

11 Claims, 6 Drawing Sheets

Fig. 3

```
A. succinogenes ATCC55618         1:----MTDLNKLVKELNDLGLTDVKEIVYNPSYEQLFEEETKPGLEGFDKGTLTTLGAVAVD  57
  (SEQ ID NO:7)
H. influenzae 86-028NP            1:----MTDLNKVVKELEALGIYDVKEVVYNPSYEQLFEEETKPGLEGFEKGTLTTGAVAVD  57
  (SEQ ID NO:9)
M. succiniciproducens MBEL55E     1:----MTDLNQLTQELGALGIHDVQEVVYNPSYELLFAEETKPGLEGYEKGTVTNQGAVAVN  57
  (SEQ ID NO:13)
P. multocida subsp.multocida str. Pm70  1:----MTDLNKVINELGALGIHDVKEIVYNPSYEQLFEEETKPGLEGYEKGIVTQSGAVAVD  57
  (SEQ ID NO:11)
S. ruminantium subsp. lactilytica 1:--------MANIDLSQYGITGTTGILHNPSYKTLFEEETKEGLTGYEQGQVSELGAVNVK  52
  (SEQ ID NO:64)
V. cholerae 623-39                1:MTVMEHTKAAQIDLAQYGITGVTELVRNPSYEMLFAEETRSDLEGYERGVVTELGAVAVD  60
  (SEQ ID NO:17)
Y. pseudotubeculosis IP32953      1:----MSVKGITPQELAAYGIHNVSEIVYNPSYDLLFEEETKPTLEGYERGTLTTGAIAVD  57
  (SEQ ID NO:15)
consensus                         1:   XXXXXXXXXXLXXXGXXXXXXXXXXNPSYXXLEXEETXXXLXGXXXXXGAXXVX  57
  (SEQ ID NO:24)

A. succinogenes ATCC55618        58:TGIFTGRSPKDKYIVCDETTKDTVWWNSE-AAKNDNKPMTQETWKSLRELVAKQLSGKRL 116
H. influenzae 86-028NP           58:TGIFTGRSPKDKYIVLDEKTKDTVWWTSE-TAKNDNKPMNQATWQSLKDLVTNQLSRKRL 116
M. succiniciproducens MBEL55E    58:TGIFTGRSPKDKYIVLDDKTKDTVWWTSE-KVKNDNKPMSQDTWNSLKGLVADQLSGKRL 116
P. multocida subsp.multocida str. Pm70  58:TGIFTGRSPKDKYIVLDDKTKDTVWWTSD-AAKNDNKPMTQDTWKSLKGLVTEQLSGKRL 116
S. ruminantium subsp. lactilytica 53:TGIFTGRSPKDKFIVDDETSHDTVWWDSE-DYHNDNHRATPETWNALKEIAKKELSNKKL 111
V. cholerae 623-39               61:TGIFTGRSPKDKFIVKDDTTRDTLWWTSD-KAKNDNKPINQEVWNDLKALVTKQLSGKRV 119
Y. pseudotubeculosis IP32953     58:TGIFTGRSPKDKYIVRDAITQDTVWWADQGKGKNDNKPLSQEIWSHLKGLVTEQLSGKRL 117
consensus                        58:TGIFTGRSPKDKXIVXDXXXXDTXWWXXXXXXXNDXXXXXXXWXXLXXXXXXLSXKXX 117
```

Fig. 4

```
A. succinogenes ATCC55618            117:FVVEGYCGASEKHRIGVRMVTEVAWQAHFVKNMFIRPTDEELKNFKADFTVLNGAKCTNP 176
H. influenzae 86-028NP               117:FVVDGFCGASEHDRLAVRIVTEVAWQAHFVKNMFIRPTEEQLKNFEPDFVMNGSKVTNP 176
M. succiniciproducens MBEL55E        117:FVVDAFCGANKDTRLAVRVVTEVAWQAHFVTNMFIRPSAEELKGFKPDFVVMNGAKCTNP 176
P. multocida subsp. multocida str. Pm70 117:FVIDAFCGANADTRLSVRIVTEVAWQAHFVKNMFIRPTEAELVGFKPDFVMNGSKVTNP 176
S. ruminantium subsp. lactilytica    112:YVVDAFCGANKDTRMAVRFIVEVAWQAHFVTNMFIQPTEEELANFKPDFVYNASKAKVE 171
V. cholerae 623-39                   120:FVLDGYCGANADTRLSVRFITEVAWQAHFVKNMFIRPSEEELAHFKPDFVVMNGAKCTNA 179
Y. pseudotuberculosis IP32953        118:FVVDITFCGANADTRLQVRFITEVAWQAHFVKNMFIRPSDEELARFEPDFIVMNGAKCTNP 177
consensus                            118:XVXXXXCGAXXXXRXXVRXXXEVAWQAHFVXNMFIXPXXXXLXXFXXDFXYXNXXKXXXX 177

A. succinogenes ATCC55618            177:NWKEQGLNSENFVAFNITEGIQLIGGTWYGGEMKKGMFSWMNYFLPLKGVASMHCSANVG 236
H. influenzae 86-028NP               177:NWKEQGLNSENFVAFNLTERIQLIGGTWYGGEMKKGMFSWMNYFLPLKGVGAMHCSANVG 236
M. succiniciproducens MBEL55E        177:NWKEQGLNSENFVAFNITEGVQLIGGTWYGGEMKKGMFSMMNYFLPLRGIASMICSANVG 236
P. multocida subsp. multocida str. Pm70 177:NWKEQGLNSENFVAFNLTEGVQLIGGTWYGGEMKKGMFSMMNYFLPLKGIASMHCSANVG 236
S. ruminantium subsp. lactilytica    172:NYKELGLHSETAVVFNLTSREQVIINTWYGGEMKKGMFSMMNYFLPLKGIAAMHCSANTD 231
V. cholerae 623-39                   180:KWKEHGLNSENFTVFNLTERMQLIGGTWYGGEMKKGMFAMMNYFLPLQGIASMHCSANMG 239
Y. pseudotuberculosis IP32953        178:QWKDQGLNSENFVAFNLTERMQLIGGTWYGGEMKKGMFSMMNYLLPLKGIASMHCSANVG 237
consensus                            178:XXKEXGLXSEXXXXFNXTXXXQXIXXTWYGGEMKKGMFXMMNYXLPLXGXXXMHCSANXX 237

A. succinogenes ATCC55618            237:KDG-DVAIFFGLSGTGKTTLSTDPKRQLIGDDEHGWDESGVFNFEGGCYAKTINLSQENE 295
H. influenzae 86-028NP               237:KDG-DVAIFFGLSGTGKTTLSTDPKREL IGDDEHGWDDVGIFNFEGGCYAKTIHLSEENE 295
M. succiniciproducens MBEL55E        237:KDG-DTAIFFGLSGTGKTTLSTDPKRQLIGDDEHGWDDEGVFNFEGGCYAKTINLSAENE 295
P. multocida subsp. multocida str. Pm70 237:EKG-DVAVFFGLSGTGKTTLSTDPKRQLIGDDEHGWDDDGVFNYEGGCYAKTIKLSPENE 295
S. ruminantium subsp. lactilytica    232:KGGQNTAIFFGLSGTGKTTLSTDPKRLLIGDDEHGWDDEGVFNFEGGCYAKVINLDMFSE 291
V. cholerae 623-39                   240:KAG-DVAIFFGLSGTGKTTLSTDPKRALIGDDEHGWDDDGVFNFEGGCYAKTIKLSKEAE 298
Y. pseudotuberculosis IP32953        238:EKG-DVAIFFGLSGTGKTTLSTDPKRKLIGDDEHGWDDDGVFNFEGGCYAKTIKLSEEAE 296
consensus                            238:XXGXXXAXFFGLSGTGKTTLSTDPKRXIIGDDEHGWDXXGXFNXEGGCYAKXIXLXXEXE 297
```

Fig. 5

```
A. succinogenes ATCC55618              296:PDIYGAIRRDALLENVVRADGSVDFDDGSKTENTRVSYPIYHIDNIVR----PVSKAGH 351
H. influenzae 86-028NP                 296:PDIYHAIRRDALLENVVRSDGSVDFDDGSKTENTRVSYPIYHIDNIVK----PVSRAGH 351
M. succiniciproducens MBEL55E          296:PDIYGAIKRDAIJENVVLDNGDVDYADGSKTENTRVSYPIYHIQNIVK----PVSKAGP 351
P. multocida subsp.multocida str. Pm70 296:PDIYKAIKRDALLENVVRADGSVDYDDGSKTENTRVSYPIYHIDNIVT----PVSKAGH 351
S. ruminantium subsp. lactilytica      292:PDIYGAIKRNALLENVTLDDKGNIDFADKTITENTRVSYPIDHIKGTVKGFVNDKSAAPA 351
V. cholerae 623-39                     299:PDIYVAIRRDALLENVTVRSDGSIDFDDGSKTENTRVSYPIYHIDNIVK----PVSKGGH 354
Y. pseudotubeculosis IP32953           297:PDIYHAIKRDALLENVVLADGTVDFNDGSKTENTRVSYPIYHIDNIVK----PVSKAGH 352
consensus                              298:PDIYXAIXRXALLENVXXXXGXXDXXTENTRVSYPIXHIXXXVXXXXXSXXXX 357

A. succinogenes ATCC55618              352:ATKVIFLTADAFGVLPPVSKLTPEQTEYYFLSGFTAKLAGTERGVTEPTPTFSACFGAAF 411
H. influenzae 86-028NP                 352:ATKVIFLTADAFGVLPPVSKLTPEQTKYYFI.SGFTAKLAGTERGITEPTPTFSACFGAAF 411
M. succiniciproducens MBEL55E          352:ATKVIFLSADAFGVLPPVSKLTPEQTKYYFLSGFTAKLAGTERGITEPTPTFSACFGAAF 411
P. multocida subsp.multocida str. Pm70 352:AKKVIFLTADAFGVLPPVSKLTPEQTKYYFLSGFTAKLAGTERGITEPTPTFSACFGAAF 411
S. ruminantium subsp. lactilytica      352:AKSVIFI.SADAFGVLPPVSIL TPEQTKYVHFLSGFTAKLAGTERGITEPTPTFSACFGQAF 411
V. cholerae 623-39                     355:ATKVIFLSADAFGVLPPVSKLTPEQTKVHFLSGFTAKLAGTERGITEPTPTFSACFGAAF 414
Y. pseudotubeculosis IP32953           353:ATKVIFLXADAFGVLPPVSRLTANQTQYHFLSGFTAKLAGTERGVTEPTPTFSACFGAAF 412
consensus                              358:AXXVIFLXADAFGVLPPVSXLTXXQTXYXFLSGFTAKLAGTERGXTEPTPTFSACFGXAF 417

A. succinogenes ATCC55618              412:LSLIIPIQYADVLVERMKASGAEAYLVNTGWNGTGKRISIKDTRGIDAILDGSIFKAEMG 471
H. influenzae 86-028NP                 412:LTLHPTQYAEVLVKRMQAAGAEAYLVNTGWNGTGKRISIKDTRGIIDAILDGSIEKAEMG 471
M. succiniciproducens MBEL55E          412:LSLHPTQYAEVLVKRMQESGAEAYLVNTGWNGTGKRISIKDTRGIIDAILDGSIDKAEMG 471
P. multocida subsp.multocida str. Pm70 412:LSLHPTQYAEVLVKRMEAAGAEAYL VNTGWNGTGKRISIKDTRGIIDAILDGSIEKAEMG 471
S. ruminantium subsp. lactilytica      415:LELHPTKYAEELVKKMEANGTKAYLVNTGWNGSGKRISIKDTRGIIDAIHSGAIKKAPTK 471
V. cholerae 623-39                     412:LTLHPTQYAEVLVKRMEAAGAEAYLVNTGWNGSGKRISIKDTRGIIDAILDGSIEKAETK 474
Y. pseudotubeculosis IP32953           413:LSI.HPTQYAEVLVKRMQAVGAQAYLVNTGWNGTGKRISIKDTRAIIDAILNGEIDKAETF 472
consensus                              418:LXLHPXXYAXXLVXXMXXGXXAYLVNTGWNGXGKRISIKDTRXIIDAIXXGXIXKAXXX 477
```

Fig. 6

| | |
|---|---|
| A. succinogenes ATCC55618 | 472:ELPIFNLAIPKALPGVDPAILDPRDTYADKAQWQVKAEDLANRFVKNFVKYTANPE-AAK 530 |
| H. influenzae 86-028NP | 472:ELPIFNLAIPKALPGVDSAILDPRDTYADKAQWQSKAEDLAGRFVKNFVKYATNEE-GKA 530 |
| M. succiniciproducens MBEL55E | 472:SLPIFDFSIPKALPGVNPAILDPRDTYADKAQWEEKAQDLAGRFVKNFEKYTGTAE-GQA 530 |
| P. multocida subsp. multocida str. Pm70 | 472:KLPIFDLAIPTALPGVDPAILDPRDTYADKAQWQAKAEDLAGRFVKNFEKYTTNDE-GKA 530 |
| S. ruminantium subsp. lactilytica | 472:KIPFFNLEVPTELEGVDTNILDPKDTYANPADWEAKAKDLAQRFIKNFDKYTKNNEAGKA 531 |
| V. cholerae 623-39 | 475:QIPIFNLQVPTALPGVDPMILDPRDTYVDPLQWESKAKDLATRFINNFDKYTDNAE-GKA 533 |
| Y. pseudotubeculosis IP32953 | 473:TLPIFDLAVPMALPGVNPDILDPRDTYADKAQWQEKAEDLAKRFATNFDKYTDTPA-GAA 531 |
| consensus | 478:XXPXFXXXXPXXLXGVXXXILDPXDTYXXXXWXXKAXDLAXRFXXNFXKYXXXXXXXXX 537 |

| | |
|---|---|
| A. succinogenes ATCC55618 | 531:LVGAGPKA- 538 |
| H. influenzae 86-028NP | 531:LIAAGPKA- 538 |
| M. succiniciproducens MBEL55E | 531:LVAAGPKA- 538 |
| P. multocida subsp. multocida str. Pm70 | 531:LVAAGPKA- 538 |
| S. ruminantium subsp. lactilytica | 532:LVAAGPQL- 539 |
| V. cholerae 623-39 | 534:LVAAGPKLD 542 |
| Y. pseudotubeculosis IP32953 | 532:LVSAGPKI- 539 |
| consensus | 538:LXXAGPXX 5450 |

METHOD FOR PRODUCING AN ORGANIC ACID

This application is a continuation under 35 U.S.C. §120 of PCT Patent Application No. PCT/JP2008/072055, filed on Dec. 4, 2008, which claims priority under 35 U.S.C. §119 to Japanese Patent Application No. 2007-315764, filed on Dec. 6, 2007, both of which are incorporated in their entireties by reference. The Sequence Listing in electronic format filed herewith is also hereby incorporated by reference in its entirety (File Name: 2010-06-03T_US-429_Seq_List; File Size: 202 KB; Date Created: Jun. 3, 2010).

BACKGROUND OF THE INVENTION

1. Field of the Invention

The present invention relates to a method for producing an organic acid such as succinic acid using a bacterium.

2. Brief Description of the Related Art

For the production of non-amino organic acids, including succinic acid, by fermentation, anaerobic bacteria are typically used, including bacteria belonging to the genus *Anaerobiospirillum* or *Actinobacillus* (U.S. Pat. Nos. 5,142,834 and 5,504,004, International Journal of Systematic Bacteriology (1999), 49, 207-216). Although such anaerobic bacteria provide high product yields, many nutrients are required for their growth, and therefore it is necessary to add large amounts of organic nitrogen sources such as corn steep liquor (CSL) into the culture medium. The addition of large amounts of sources of organic nitrogen results in not only an increase in cost for the culture medium, but also an increase in the purification cost for isolating the product, and therefore it is not economical.

In addition, methods are known in which aerobic bacteria such as coryneform bacteria are cultured once under aerobic conditions to proliferate the bacterial cells, then the bacteria are harvested and washed. As a result, a non-amino organic acid is produced without having to supply oxygen (Japanese Patent Laid-open (KOKAI) Nos. 11-113588 and 11-196888). These methods are economical, since smaller amounts of organic nitrogen can be added, and sufficient growth of the bacteria can be obtained in a simple culture medium. However, there is still room for improvement in terms of production amounts, concentration, and production rate per cell of the target organic acids, and the like. Furthermore, the production process could be simplified.

*Escherichia coli* is a facultative anaerobic gram negative bacterium, and similar to when using coryneform bacteria, methods are known for producing a non-amino organic acid by culturing the bacteria once under aerobic conditions to allow for bacterial growth, and then culturing again in the absence of oxygen to anaerobically produce the non-amino organic acid (Journal of Industrial Microbiology and Biotechnology (2002), 28 (6), 325-332). Alternatively, the bacteria can be aerobically cultured to aerobically produce the non-amino organic acid (U.S. Patent Published Application No. 20050170482). However, since *Escherichia coli* is a gram-negative bacterium, it is vulnerable to osmotic pressure, and there remains room for improvement in productivity per cell etc.

As for the breeding of such bacteria as described above and in regards to the anaplerotic pathway, the production of non-amino organic acids by fermentation utilizing strains of *Escherichia coli*, coryneform bacterium, or the like, has been reported. Specifically, in these bacteria, phosphoenolpyruvate carboxylase (PEPC) activity or pyruvate carboxylase (PYC) activity is enhanced, and the like (for example, Japanese Patent Laid-open Nos. 11-196888 and 11-196887, Applied and Environmental Microbiology (1996), 62, 1808-1810).

As for phosphoenolpyruvate carboxykinase (PEPCK), it is thought that this enzyme generates phosphoenolpyruvic acid from oxalacetic acid by decarboxylation, and it mainly advances the metabolic reactions toward glyconeogenesis (Applied and Environmental Microbiology (1996), 62, 1808-1810, Applied and Environmental Microbiology (1993), 59, 4261-4265). Another type of PEPCK enzyme has been reported that is in equilibrium with the reverse reaction of the reaction described above, that is, the reaction that generates oxalacetic acid from phosphoenolpyruvic acid by carbon dioxide fixation. The presence of this type of PEPCK has been confirmed in some bacteria which produce succinic acid in the presence of high concentrations of carbon dioxide, that is, *Mannheimia succiniciproducens, Actinobacillus succinogenes, Anaerobiospirillum succiniciproducens*, and *Selenomonas ruminantium* (Applied and Environmental Microbiology (2006), 72, 1939-1948, Applied and Environmental Microbiology (1997), 63, 2273-2280, Applied and Environmental Microbiology (2004), 70, 1238-1241, Microbiology (2001), 147, 681-690). It has also been reported that increasing the activity of PEPCK derived from *Actinobacillus succinogenes* in *Escherichia coli* is effective for increasing production of succinic acid (Applied and Environmental Microbiology (2004), 70, 1238-1241). However, this improvement was confirmed only in a PEPC-deficient strain, and the converse has also been reported, in that the increase in the production of succinic acid is NOT observed in a non-deficient strain (Applied and Environmental Microbiology (2004), 70, 1238-1241).

Furthermore, although efficient production of ethanol and hydrogen has been reported in strains of *Enterobacter* bacteria, it has not been reported whether any strain can efficiently produce a non-amino organic acid (Journal of Bioscience and Bioengineering (2005), 100, 260-265, Japanese Patent Laid-open No. 2006-180782).

SUMMARY OF THE INVENTION

An aspect of the present invention is to provide a method for producing an organic acid using a bacterium that shows higher production efficiency.

It has been found that the production yield of an organic acid can be increased by using a bacterium which belongs to the family Enterobacteriaceae, such as *Enterobacter, Pantoea, Erwinia, Klebsiella*, and *Raoultella*, and has been modified so that the phosphoenolpyruvate carboxykinase activity is enhanced. A product obtained by processing such a bacterium can also be used.

It is an aspect of the present invention to provide a method for producing an organic acid comprising:

A) allowing a substance to act on an organic raw material in a reaction mixture containing carbonate ions, bicarbonate ions, or carbon dioxide gas, wherein the substance is selected from the group consisting of:
  i) a bacterium belonging to the family Enterobacteriaceae which has an ability to produce an organic acid and has been modified so that the phosphoenolpyruvate carboxykinase activity is enhanced,
  ii) a product obtained by processing the bacterium of i), and
  iii) combinations thereof; and
B) collecting the organic acid,
wherein the bacterium belongs to a genus selected from the group consisting of *Enterobacter, Pantoea, Erwinia, Klebsiella*, and *Raoultella*.

It is a further aspect of the present invention to provide the method as described above, wherein the bacterium has been modified by a method selected from the group consisting of:
  i) increasing the copy number of the pckA gene,
  ii) modifying an expression control sequence of the pckA gene, and
  iii) combinations thereof.

It is a further aspect of the present invention to provide the method as described above, wherein the pckA gene is selected from the group consisting of:
  (a) a DNA comprising a nucleotide sequence selected from the group consisting of SEQ ID NO: 6, 8, 10, 12, 14, 16 and 64, and
  (b) a DNA which hybridizes with a nucleotide sequence complementary to a nucleotide sequence selected from the group consisting of SEQ ID NO: 6, 8, 10, 12, 14, 16 and 64 under stringent conditions, and said DNA codes for a protein having phosphoenolpyruvate carboxykinase activity.

It is a further aspect of the present invention to provide the method as described above, wherein the pckA gene codes for a protein selected from the group consisting of:
  A) a protein comprising an amino acid sequence selected from the group consisting of SEQ ID NO: 7, 9, 11, 13, 15, 17, 65, and 24; and
  B) a protein comprising an amino acid sequence selected from the group consisting of SEQ ID NO: 7, 9, 11, 13, 15, 17, 65 and 24, but which includes one or more substitutions, deletions, insertions, or additions of one or several amino acid residues.

It is a further aspect of the present invention to provide the method as described above, wherein the bacterium has been further modified to decrease the activity of an enzyme selected from the group consisting of alcohol dehydrogenase, lactate dehydrogenase, phosphate acetyltransferase, α-acetolactate decarboxylase, pyruvate formate lyase, and combinations thereof.

It is a further aspect of the present invention to provide the method as described above, wherein the enzyme is alcohol dehydrogenase.

It is a further aspect of the present invention to provide the method as described above, wherein the enzymes are alcohol dehydrogenase and lactate dehydrogenase.

It is a further aspect of the present invention to provide the method as described above, wherein the enzymes are alcohol dehydrogenase, lactate dehydrogenase, and phosphate acetyltransferase.

It is a further aspect of the present invention to provide the method as described above, wherein the enzymes are alcohol dehydrogenase, lactate dehydrogenase, phosphate acetyltransferase, and α-acetolactate decarboxylase.

It is a further aspect of the present invention to provide the method as described above, wherein the enzymes are alcohol dehydrogenase, lactate dehydrogenase, phosphate acetyltransferase, α-acetolactate decarboxylase, and pyruvate formate lyase.

It is a further aspect of the present invention to provide the method as described above, wherein the bacterium has been further modified so that pyruvate carboxylase activity is enhanced.

It is a further aspect of the present invention to provide the method as described above, wherein the organic acid is succinic acid.

It is a further aspect of the present invention to provide a method for producing a succinic acid-containing polymer comprising:
  A) producing succinic acid by the method as described above, and
  B) polymerizing the succinic acid.

BRIEF DESCRIPTION OF THE DRAWINGS

FIG. 3 shows the alignment and consensus sequence of the amino acid sequences of various types of PEPCK.

FIG. 4 shows the alignment and consensus sequence of amino acid sequences of various types of PEPCK (continuation).

FIG. 5 shows the alignment and consensus sequence of amino acid sequences of various types of PEPCK (continuation).

FIG. 6 shows the alignment and consensus sequence of amino acid sequences of various types of PEPCK (continuation).

DETAILED DESCRIPTION OF THE PREFERRED EMBODIMENTS

Figure 1:
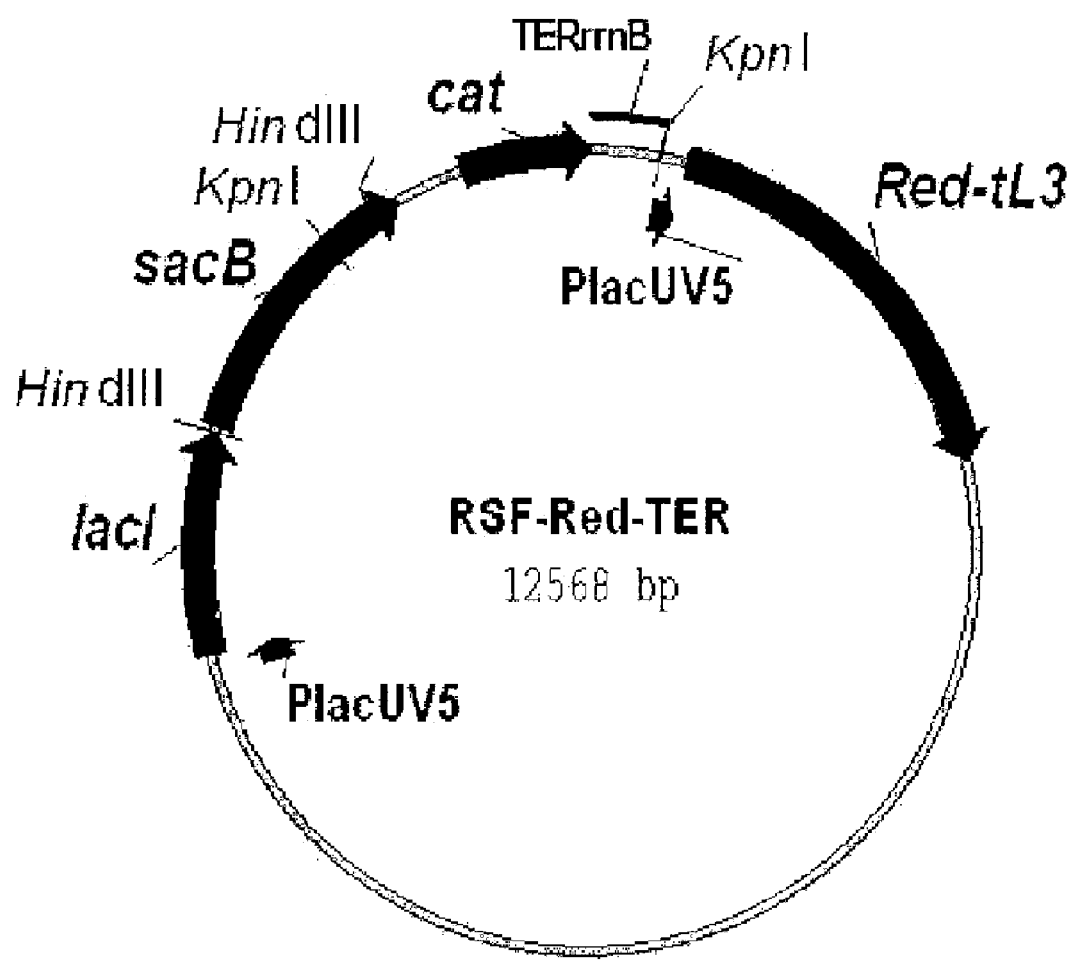
FIG. 1 shows the structure of the helper plasmid RSF-Red-TER.

Hereinafter, aspects of the presently disclosed subject matter will be explained in detail.

<1> Bacterium

The bacterium used in accordance with the presently disclosed subject matter can be a bacterium which has an ability to produce an organic acid and has been modified so that the phosphoenolpyruvate carboxykinase (henceforth abbreviated as "PEPCK") activity is enhanced. The term "ability to produce an organic acid" can mean that the bacterium is able to produce and accumulate an organic acid in a medium to such a degree that the organic acid can be collected from the medium when the bacterium is cultured in the medium. The bacterium of the present invention can produce a target organic acid in a medium in an amount of, for example, 0.5 g/L or more, or 1.0 g/L or more in another example. Such a bacterium can be obtained by modifying a parent bacterial strain which already is able to produce an organic acid so that the PEPCK activity is enhanced. When the parent strain does not naturally produce an organic acid, the ability to produce an organic acid can be imparted to the parent strain, and then the bacterium can be modified so that the PEPCK activity is enhanced. Furthermore, the ability to produce an organic acid can be imparted to a strain which has already been modified to enhance the PEPCK activity. The ability to produce an organic acid can be native to the chosen bacterium, or can be obtained by modifying the bacterium using mutational techniques or recombinant DNA techniques.

The organic acid can be a metabolic intermediate of the TCA cycle, and examples include succinic acid, malic acid, fumaric acid, citric acid, isocitric acid, cis-aconitic acid, and the like.

The parent strain that can be used to derive the bacterium as described in the presently disclosed subject matter can be a bacterium belonging to the family Enterobacteriaceae, such as *Enterobacter, Pantoea, Erwinia, Klebsiella*, and *Raoultella* bacteria.

*Pantoea* bacteria, *Erwinia* bacteria, *Enterobacter* bacteria, *Klebsiella* bacteria and *Raoultella* bacteria are classified as γ-proteobacteria, and they are taxonomically very close to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (Int. J. Syst. Bacteriol., 1989, 39:337-345). Furthermore, some bacteria belonging to the genus *Erwinia* were reclassified as *Pantoea ananas* or *Pantoea stewartii* (Int. J. Syst. Bacteriol., 1993, 43:162-173).

Examples of the *Enterobacter* bacteria include *Enterobacter agglomerans, Enterobacter aerogenes*, and the like. Specifically, the strains exemplified in European Patent Application Laid-open No. 952221 can be used. Typical strains of the genus *Enterobacter* include *Enterobacter agglomerans* ATCC 12287, *Enterobacter aerogenes* ATCC 13048, *Enterobacter aerogenes* NBRC 12010 strain (Biotechnol Bioeng., 2007, Mar. 27; 98(2):340-348), *Enterobacter aerogenes* AJ110637 (FERM ABP-10955), and the like.

These strains are available from, for example, the American Type Culture Collection (Address: 10801 University Boulevard, Manassas, Va. 20110, United States of America). That is, registration numbers are given to each of the strains, and the strains can be ordered using these numbers. The registration numbers of the strains are listed in the catalogue of the American Type Culture Collection. The *Enterobacter aerogenes* AJ110637 strain was deposited at the International Patent Organism Depositary, Agency of Industrial Science and Technology (Central 6, 1-1, Higashi 1-Chome, Tsukubashi, Ibaraki-ken, 305-8566, Japan) on Aug. 22, 2007, and assigned an accession number of FERM P-21348. Then, the deposit was converted to an international deposit based on the Budapest Treaty on Mar. 13, 2008, and assigned an accession number of FERM BP-10955.

Typical strains of the *Pantoea* bacteria include *Pantoea ananatis, Pantoea stewartii, Pantoea agglomerans*, and *Pantoea citrea*. Specific examples include the following strains:

*Pantoea ananatis* AJ13355 (FERM BP-6614, European Patent Laid-open No. 0952221)

*Pantoea ananatis* AJ13356 (FERM BP-6615, European Patent Laid-open No. 0952221)

Although these strains are described as *Enterobacter agglomerans* in European Patent Laid-open No. 0952221, they are currently classified as *Pantoea ananatis* on the basis of nucleotide sequence analysis of the 16S rRNA etc., as described above.

Examples of the *Erwinia* bacteria include *Erwinia amylovora* and *Erwinia carotovora*, examples of the *Klebsiella* bacteria include *Klebsiella oxytoca* and *Klebsiella planticola*, and examples of the *Raoultella* bacteria include *Raoultella terrigena* and *Raoultella planticola*.

Specific examples include the following strains:
*Erwinia amylovora* ATCC 15580 strain
*Erwinia carotovora* ATCC 15713 strain
*Klebsiella planticola* AJ13399 strain (FERM BP-6600, European Patent Laid-open No. 955368)
*Klebsiella planticola* AJ13410 strain (FERM BP-6617, European Patent Laid-open No. 955368).
*Raoultella planticola* ATCC 33531 strain Although the AJ13399 strain and the AJ13410 strain were classified as *Klebsiella planticola* at the time of the deposit, *Klebsiella planticola* is currently classified as *Raoultella planticola* (Int. J. Syst. Evol. Microbiol., 2001 May, 51(Pt 3):925-32).

<1-1> Impartation of the Ability to Produce an Organic Acid

Hereinafter, methods for imparting to bacteria the ability to produce an organic acid, or methods to enhance the ability of bacteria to produce an organic acid are described.

To impart the ability to produce an organic acid, methods conventionally used to breed bacteria for producing substances by fermentation can be used (see "Amino Acid Fermentation", Japan Scientific Societies Press, 1st Edition, published May 30, 1986, pp. 77-100). Such methods include by acquiring an auxotrophic mutant, an analogue-resistant strain, or a metabolic regulation mutant, or by constructing a recombinant strain having enhanced expression of an enzyme involved in the biosynthesis of an organic acid. When breeding bacteria to produce an organic acid, one or more properties, such as an auxotrophic mutation, analogue resistance, or metabolic regulation mutation, can be imparted. The expression of one or more enzymes involved in biosynthesis of an organic acid can be enhanced. Furthermore, imparting properties such as auxotrophy, analogue resistance, or metabolic regulation can be combined with enhancing biosynthetic enzymes.

An auxotrophic mutant strain, a strain resistant to an organic acid analogue, or a metabolic regulation mutant strain which is able to produce an organic acid can be obtained by subjecting a parent or wild-type strain to a conventional mutagenesis, such as exposure to X-rays or UV irradiation, or a treatment with a mutagen such as N-methyl-N'-nitro-N-nitrosoguanidine, and then selecting the bacteria which exhibit an auxotrophy, analogue resistance, or metabolic regulation mutation and which also are able to produce an organic acid.

Methods for imparting to bacteria an ability to produce an organic acid, and organic acid-producing bacteria will be specifically exemplified below.

Succinic Acid-Producing Bacteria

Bacteria which can be used to produce succinic acid include strains that are unable to produce acetic acid, lactic acid, ethanol, 2,3-butanediol and formic acid.

Strains that are unable to produce acetic acid, lactic acid, ethanol, 2,3-butanediol and formic acid include strains that cannot assimilate acetic acid and lactic acid in a minimal medium, or strains in which the activities of the lactic acid biosynthesis genes and acetic acid biosynthesis enzymes mentioned below are decreased (International Patent Publication WO2005/052135).

Moreover, such strains as described above can also be obtained by imparting resistance to monofluoroacetic acid (U.S. Pat. No. 5,521,075).

Production of succinic acid can be improved by imparting the ability to assimilate glucose under anaerobic conditions to a strain that is unable to produce both formic acid and lactic acid (International Patent Publication WO97/16528).

The ability to produce succinic acid can also be imparted by amplifying a gene which encodes an enzyme which is involved in the succinic acid biosynthesis system, or by deleting a gene which encodes an enzyme which catalyzes a reaction which branches off from the succinic acid biosynthesis system to produce another compound.

The ability to produce succinic acid can also be imparted by modifying a bacterium to decrease the enzymatic activity of lactate dehydrogenase (LDH), which is a lactic acid biosynthesis system enzyme (International Patent Publications WO2005/052135, WO2005/116227, U.S. Pat. No. 5,770,435, U.S. Patent Published Application No. 20070054387, International Patent Publication WO99/53035, Alam, K. Y. and Clark, D. P., 1989, J. Bacteriol., 171:6213-6217). Some bacteria can have L-lactate dehydrogenase and D-lactate dehydrogenase, and such bacteria can be modified to decrease the activity of either one, or both, of these enzymes.

The ability to produce succinic acid can also be imparted by modifying a bacterium to decrease the enzymatic activity of the formic acid biosynthesis system enzyme, pyruvate-formate lyase (PFL) (U.S. Patent Published Application No. 20070054387, International Patent Publications WO2005/116227, WO2005/52135, Donnelly, M. I., Millard, C. S., Clark, D. P., Chen, M. J., Rathke, J. W., 1998, Appl. Biochem. Biotechnol., 70-72, 187-198.).

The ability to produce succinic acid can also be imparted by modifying a bacterium to decrease the enzymatic activities of phosphate acetyltransferase (PTA), acetate kinase (ACK), pyruvate oxidase (PDXB), acetyl-CoA synthetase (ACS) and acetyl-CoA hydrolase (ACH), which are all acetic acid biosynthesis system enzymes (U.S. Patent Published Application No. 20070054387, International Patent Publications WO2005/052135, WO99/53035, WO2006/031424, WO2005/113745, and WO2005/113744).

The ability to produce succinic acid can also be enhanced by modifying a bacterium to decrease the enzymatic activity of alcohol dehydrogenase (ADH), which is an ethanol biosynthesis system enzyme (refer to International Patent Publication WO2006/031424).

A strain with an enhanced ability to produce succinic acid can also be obtained by decreasing the activity of α-acetolactate decarboxylase, which is a 2,3-butanediol biosynthesis system enzyme (J. Biosci. Bioeng., 2004, 97(4):227-32).

The ability to produce succinic acid can also be enhanced by decreasing the activities of pyruvate kinase, glucose PTS (ptsG), ArcA protein, IclR protein (iclR), glutamate dehydrogenase (gdh) and/or glutamine synthetase (glnA), and glutamate synthase (gltBD) (International Patent Publication WO2006/107127, No. 2007007933, Japanese Patent Laid-open No. 2005-168401). The gene abbreviations are in the parentheses following the enzyme names.

The ability to produce succinic acid can also be imparted by enhancing a biosynthesis system enzyme involved in succinic acid production.

The ability to produce succinic acid can also be enhanced by enhancing enzymatic activities of pyruvate carboxylase, malic enzyme, phosphoenolpyruvate carboxylase, fumarase, fumarate reductase, and malate dehydrogenase (Japanese Patent Laid-open No. 11-196888, International Patent Publication WO99/53035, 2001. Biotechnol. Bioeng., 74:89-95, Millard, C. S., Chao, Y. P., Liao, J. C., Donnelly, M. I., 1996, Appl. Environ. Microbiol., 62:1808-1810, International Patent Publication WO2005/021770, Japanese Patent Laid-open No. 2006-320208, Pil Kim, Maris Laivenieks, Claire Vieille, and J. Gregory Zeikus, 2004, Appl. Environ. Microbiol., 70:1238-1241). The enzymatic activities of these target enzymes can be enhanced by referring to the methods for enhancing expression of the pckA gene described later.

Specific examples of succinic acid-producing bacteria belonging to the family Enterobacteriaceae include the following strains:

*Enterobacter aerogenes* AJ110637 strain (FERM ABP-10955)

*Enterobacter aerogenes* VP-1 strain (J. Biosci. Bioeng., 2004, 97(4):227-32)

<1-2> Enhancing the Phosphoenolpyruvate Carboxykinase Activity

The bacterium in accordance with the presently disclosed subject matter can be obtained by modifying a bacterium having an ability to produce an organic acid such as those described above so that the phosphoenolpyruvate carboxykinase (PEPCK) activity is enhanced. However, the modification to enhance the PEPCK activity can be performed first, and then the ability to produce an organic acid can be imparted.

Phosphoenolpyruvate carboxykinase (PEPCK) reversibly catalyzes the reaction which produces oxalacetic acid (OAA) from phosphoenolpyruvic acid (PEP) by carbon dioxide fixation. "PEPCK activity" can mean the activity of catalyzing the reaction to produce OAA from PEP. PEPCK enzymes which are able to achieve reaction equilibrium and advance the reaction which results in the production of OAA from PEP can be used. The enzyme activity can be determined, for example, by measuring the amount of ATP produced at 37° C. according to the method of Pil Kim et al. using Sigma Diagnostics ATP Kit (Pil, Kim., Maris, Laivenieks., Claire, Vieille., Gregory, Zeikus., Applied And Environmental Microbiology, February 2004, pp. 1238-1241).

The increase of the PEPCK activity as compared to that of, for example, a wild-type or unmodified strain can be confirmed by measuring the enzyme activity according to the aforementioned method, or by comparing the amount of mRNA of a gene coding for PEPCK with that of the wild-type or unmodified strain. To confirm expression, exemplary methods include Northern hybridization and reverse transcriptase PCR (RT-PCR, Sambrook, J., and Russell, D. W., Molecular Cloning A Laboratory Manual/Third Edition, New York: Cold Spring Harbor Laboratory Press (2001)). The enzyme activity can be increased to any level so long as the activity is increased as compared to that of a wild-type or unmodified strain, and for example, is increased not less than 1.5 times, not less than 2 times in another example, or not less than 3 times in another example, as compared to that of, for example, a wild-type or an unmodified strain. Moreover, the increase in the enzyme activity can also be confirmed on the basis of detection of an increase in the amount of the PEPCK protein as compared to that in an unmodified or a wild-type strain, and it can be detected by, for example, Western blotting using an antibody (Sambrook, J., and Russell, D. W., Molecular Cloning A Laboratory Manual/Third Edition, New York: Cold Spring Harbor Laboratory Press (2001)).

Examples of the gene coding for PEPCK can include the pckA gene derived from *Actinobacillus succinogenes* (Gen-Bank Accession No. YP_001343536.1, SEQ ID NO: 6), and homologues of this pckA gene. A pckA gene homologue is a gene that can be derived from another microorganism, shows high homology to the aforementioned pckA gene of *Actinobacillus succinogenes*, and codes for a protein having the PEPCK activity. Examples include, for example, the pckA gene of *Haemophilus influenzae* (GenBank Accession No. YP_248516.1, SEQ ID NO: 8), the pckA gene of *Pasteurella multocida* (GenBank Accession No. NP_246481.1, SEQ ID NO: 10), the pckA gene of *Mannheimia succiniciproducens* (GenBank Accession No. YP_089485.1, SEQ ID NO: 12), the pckA gene of *Yersinia pseudotuberculosis* (GenBank Accession No. YP_072243, SEQ ID NO: 14), the pckA gene of *Vibrio cholerae* (GenBank Accession No. ZP_01981004.1, SEQ ID NO: 16), the pckA gene of *Selenomonas ruminantium* (GenBank Accession No. AB016600, SEQ ID NO: 64), and so forth.

Examples of pckA gene homologues include genes coding for a protein having a homology of, for example, 90% or more, 95% or more, 98% or more, or 99% or more in another example, to the amino acid sequence of SEQ ID NO: 7, 9, 11, 13, 15, 17 or 65, and coding for phosphoenolpyruvate carboxykinase. Homology of amino acid sequences and nucleotide sequences can be determined by using, for example, the algorithm BLAST of Karlin and Altschul (Pro. Natl. Acad. Sci. USA, 90, 5873 (1993)) or FASTA (Methods Enzymol., 183, 63 (1990)). The BLASTN and BLASTX programs were developed on the basis of this algorithm BLAST (refer to http://www.ncbi.nlm.nih.govbi.nlm.nih.gov). In this specification, the term "homology" can also refer to "identity", at least when referring to DNA sequences.

Alignment of the amino acid sequences of SEQ ID NOS: 7, 9, 11, 13, 15, 17 and 65 is shown in FIGS. 3 to 6. A consensus of these sequences is shown as SEQ ID NO: 24. The aforementioned pckA gene homologues can include a gene coding for the amino acid sequence of SEQ ID NO: 24, and genes coding for a protein having a homology of, for example, 90% or more, 95% or more, 98% or more, or 99% or more in another example, to the amino acid sequence of SEQ ID NO: 24, and coding for phosphoenolpyruvate carboxykinase.

Since sequences of the pckA gene from several different sources have already been reported as described above, the gene can be obtained by PCR using primers prepared on the basis of those nucleotide sequences. For example, the coding region of the pckA gene of *Actinobacillus succinogenes* and a flanking region which includes a control region, can be obtained by PCR (polymerase chain reaction, see White, T. J. et al., Trends Genet., 5, 185 (1989)) using the primers shown in SEQ ID NOS: 4 and 5 and chromosomal DNA of *Actinobacillus succinogenes* can be used as the template. Specific examples of *Actinobacillus succinogenes* include the 130Z strain (ATCC 55618). This strain can be obtained from American Type Culture Collection (Address: 10801 University Boulevard, Manassas, Va. 20110, United States of America). Homologues of pckA from other microorganisms can also be obtained in a similar manner.

Since the nucleotide sequence of the pckA gene can differ depending on the species or strain of bacteria belonging to the family Enterobacteriaceae, the pckA gene is not limited to a gene coding for the amino acid sequence of SEQ ID NO: 7, 9, 11, 13, 15, 17, 65 or 24, and it can be a mutant or artificially modified gene that codes for a protein having a sequence of SEQ ID NO: 7, 9, 11, 13, 15, 17, 65 or 24, but which includes substitutions, deletions, insertions, additions, etc. of one or several amino acid residues at one or more positions so long as the ability is maintained to improve production of an organic acid by the bacterium with enhanced expression of the gene. Although the number meant by the term "several" can differ depending on positions in the three-dimensional structure of the protein or types of amino acid residues, it can be 1 to 20, 1 to 10 in another example, or 1 to 5 in another example. The substitutions, deletions, insertions, additions, inversions or the like of amino acid residues described above can also include those caused by a naturally occurring mutation based on individual differences, differences in species of microorganisms that contain the pckA gene (mutant or variant), or the like.

The aforementioned substitution can be a conservative substitution that is a neutral substitution, that is, one that does not result in a functional change. The conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitutions considered to be conservative substitutions can include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

Furthermore, the pckA gene can include a nucleotide sequence encoding a protein having a homology not less than 80% in one example, not less than 90% in another example, not less than 95% in another example, or not less than 97% in another example, to the entire amino acid sequence of SEQ ID NO: 7, 9, 11, 13, 15, 17, 65 or 24, and wherein the encoded protein improves the ability of the bacterium to produce an organic acid when expression of the gene is enhanced. Furthermore, the degree of degeneracy of the gene can vary depending on the host into which the pckA gene is introduced, and therefore codons can be replaced with those which are favorable for the chosen host. Moreover, the pckA gene can code for a protein with an elongated or deleted N- or C-terminal sequence, so long as the gene improves the ability of the bacterium to produce an organic acid when expression of the gene is enhanced in the bacterium. The length of the amino acid sequence to be elongated or deleted can be 50 amino acid residues or less, 20 or less in another example, 10 or less in another example, or 5 or less in another example. More specifically, the pckA gene can encode a protein having the amino acid sequence of SEQ ID NO: 7, 9, 11, 13, 15, 17, 65, or 24, but wherein the sequence is elongated by 5 to 50 amino acid residues on the N-terminal or C-terminal side, or 5 to 50 residues are deleted on either side.

Genes homologous to the pckA gene as described above can be obtained by modifying a gene coding for the amino acid sequence of SEQ ID NO: 7, 9, 11, 13, 15, 17, 65 or 24 so that the protein encoded by the gene includes substitutions, deletions, insertions, or additions of amino acid residues at a specific site(s), for example, by site-specific mutagenesis. Furthermore, homologous genes can also be obtained by conventionally known mutation treatments, such as those described below. For example, the pckA gene can be treated with hydroxylamine or the like in vitro, or the microorganism, for example, *Actinobacillus succinogenes*, containing the gene can be treated with ultraviolet ray irradiation or a mutagen typically used for mutation, such as N-methyl-N'-nitro-N-nitrosoguanidine (NTG) or ethyl methanesulfonate (EMS). Another method for introducing mutations is error-prone PCR (Cadwell, R. C., PCR Meth. Appl., 2, 28 (1992)), DNA shuffling (Stemmer, W. P., Nature, 370, 389 (1994)), or StEP-PCR (Zhao, H., Nature Biotechnol., 16, 258 (1998)). Regardless of the method used, a mutation can be artificially introduced into the pckA gene by gene recombination to obtain a gene coding for highly active PEPCK.

Whether such homologous pckA genes code for a protein which improves the ability of the bacterium to produce an organic acid when expression is enhanced can be confirmed, for example, by introducing these genes into a ΔadhE strain of the *Enterobacter aerogenes* AJ110637 strain (FERM BP-10955) or the like, and determining whether the organic acid-producing ability of the bacterium is improved or not. For example, by adding a reducing substance such as glucose, and an organic acid such as malic acid, to the medium and comparing the amount of succinic acid or fumaric acid which is converted from the malic acid utilizing the reducing power which occurs when glucose is assimilated, the effect can be more clearly verified.

Examples of the pckA gene also include a DNA that hybridizes with a nucleotide sequence complementary to the sequence of SEQ ID NO: 6, 8, 10, 12, 14, 16 or 64, or a probe that can be prepared from these sequences under stringent conditions and codes for a protein which has the PEPCK activity. The "stringent conditions" can be conditions under which a so-called specific hybrid is formed, and non-specific hybrid is not formed. Examples include, for example, conditions under which DNAs having high homology to each other, for example, DNAs having a homology of, for example, not less than 80%, not less than 90%, not less than 95%, or not less than 97% in another example, hybridize with each other, and DNAs having homology lower than the above levels do not hybridize with each other. "Stringent conditions" can also include washing conditions which are typical in Southern hybridization, for example, washing once, or twice or three times, at salt concentrations and a temperature of 1×SSC, 0.1% SDS at 60° C., 0.1×SSC, 0.1% SDS at 60° C. in another example, or 0.1×SSC, 0.1% SDS at 68° C. in another example.

A partial sequence of a nucleotide sequence complementary to the sequence of SEQ ID NO: 6, 8, 10, 12, 14, 16 or 64 can also be used as the probe. Such a probe can be prepared by PCR using oligonucleotides prepared on the basis of any one of these nucleotide sequences as primers and a DNA fragment containing any one of the sequences as the template. When a DNA fragment having a length of about 300 bp is used as the probe, the washing conditions after hybridization under the aforementioned conditions can be exemplified by 2×SSC, 0.1% SDS at 50° C.

The aforementioned descriptions concerning gene homologues and conservative mutations can be similarly applied to the other enzyme genes described in this specification.

By modifying a bacterium so that expression of a pckA gene as described above is enhanced, the PEPCK enzyme activity can be enhanced.

The expression "modified so that expression of the pckA gene is enhanced" or "modified to enhance express of the pckA gene" can mean that the number of PEPCK molecules per cell is increased, or that the activity per PEPCK molecule is increased, etc., as compared to a parent strain or a wild-type strain. Examples of the wild-type strain that can be used for comparison include the *Enterobacter aerogenes* ATCC 13048 strain and so forth.

Expression of the pckA gene can be enhanced by increasing the copy number of the pckA gene. For example, the copy number of the gene can be increased by ligating a fragment containing the pckA gene to a vector that functions in the chosen bacterium, for example, a multi copy vector, to prepare a recombinant DNA, and transforming the bacterium which is able to produce an organic acid as described above with the DNA. Alternatively, after the transformation of a wild-type strain of a bacterium, the ability to produce an organic acid can be imparted to the transformed bacterium. The copy number of the gene can also be increased by transferring a single copy or multiple copies of the pckA gene to the bacterial chromosome. Transfer of the pckA gene to the chromosome can be confirmed by Southern hybridization using a portion of the pckA gene as a probe.

Expression of the pckA gene can also be enhanced by modifying an expression control sequence of the pckA gene. For example, the promoter sequence of the pckA gene can be replaced with a stronger promoter, or by making a promoter sequence closer to a consensus sequence (WO00/18935).

Methods for constructing a bacterium which has an ability to produce an organic acid and has been modified so that the expression level of the pckA gene is increased are explained below. These methods can be performed as described in a manual such as Molecular Cloning (Cold Spring Harbor Laboratory Press, Cold Spring Harbor (USA), 2001).

Expression of the pckA gene can be enhanced by increasing the copy number by amplifying the pckA gene using a plasmid such as those described below. First, the pckA gene is cloned from the chromosome of *Actinobacillus succinogenes* or the like. Chromosomal DNA can be prepared from a bacterium, for example, by the method of Saito and Miura (see H. Saito and K. Miura, Biochem. Biophys. Acta, 72, 619 (1963); Text for Bioengineering Experiments, Edited by the Society for Bioscience and Bioengineering, Japan, p 97-98, Baifukan Co., Ltd., 1992), or the like. Oligonucleotides for use in PCR can be synthesized on the basis of the aforementioned known information, for example, the synthetic oligonucleotides shown in SEQ ID NOS: 4 and 5 can be used to amplify the pckA gene.

A gene fragment including the pckA gene amplified by PCR can itself be amplified by inserting the fragment into a vector having a replication origin that enables autonomous replication in the chosen bacterium, then transforming the bacterium with the vector. Examples of vectors which can be used to transform Enterobacteriaceae bacteria include pUC19, pUC18, pHSG299, pHSG399, pHSG398, RSF1010, pBR322, pACYC184, pMW219, and the like.

To prepare a recombinant DNA by ligating the pckA gene to a vector that functions in the chosen bacterium, the vector is digested with a restriction enzyme suitable for the ends of the pckA gene. Such a restriction enzyme site can be introduced in advance into the synthetic oligonucleotide which is used to amplify the pckA gene. Ligation is usually performed by a ligase such as T4 DNA ligase.

In order to introduce a recombinant plasmid prepared as described above into a bacterium, any known transformation method reported to date can be employed. For example, recipient cells can be treated with calcium chloride so as to increase permeability for the DNA, which has been reported for *Escherichia coli* K-12 (Mandel, M. and Higa, A., J. Mol. Biol., 53, 159 (1970)). Also, competent cells can be prepared from growing cells and DNA can be introduced into these cells, which has been reported for *Bacillus subtilis* (Duncan, C. H., Wilson, G. A. and Young, F. E., Gene, 1, 153 (1977)). Another method is to make DNA recipient cells into protoplasts or spheroplasts which easily take up a recombinant DNA, and a recombinant DNA can be introduced into these cells, which are known for *Bacillus subtilis*, actinomycetes, and yeasts (Chang, S. and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)). In addition, bacteria can also be transformed by the electric pulse method (Japanese Patent Laid-open No. 2-207791) or by the conjugal transfer method (Biotechnology (NY). 1991 January; 9(1):84-7).

The copy number of the pckA gene can also be increased by integrating multiple copies of the pckA gene into the chromosomal DNA of the bacterium, which can be accomplished by homologous recombination. This technique is performed by targeting a sequence which is present in multiple copies on the chromosomal DNA. Such sequences can include a repetitive DNA or inverted repeat present at the end of a transposable element. Alternatively, as disclosed in Japanese Patent Laid-open No. 2-109985, multiple copies of the pckA gene can be introduced into a chromosomal DNA by incorporating them into a transposon, and transferring the transposon (Japanese Patent Laid-open Nos. 2-109985, 7-107976, Mol. Gen. Genet., 245, 397-405 (1994); Plasmid, 2000 November; 44(3): 285-91).

Expression of the pckA gene can also be enhanced by replacing a native expression control sequence, such as a promoter of the pckA gene, on the chromosomal DNA or a plasmid with a stronger promoter. Other methods include modifying a factor involved in expression control of the pckA gene, such as operator or repressor, or ligating a strong terminator (Hamilton et al., Journal of Bacteriology 171:4617-4622; WO98/004715). For example, the lac promoter, trp promoter, trc promoter, tac promoter, PR promoter derived from λ-phage, lacUV promoter, and the like are known as strong promoters. Methods for evaluating the strength of promoters and examples of strong promoters are described in the paper of Goldstein et al. (Prokaryotic promoters in biotechnology, Biotechnol. Annu. Rev., 1955, 1, 105-128), and the like. Furthermore, as disclosed in WO00/18935, the strength of a promoter can be increased by making several nucleotide substitutions in the promoter region of a target gene so as to make the sequence closer to a consensus sequence. For example, the −35 region can be replaced with TTGACA or TTGCCA, and the −10 region can be replaced with TATAAT or TATAAC. In addition, it is known that the translation efficiency of mRNA is significantly affected by substituting several nucleotides in the spacer region between the ribosome-binding site (RBS) and the translation initiation codon, in particular, the sequence immediately upstream of the initiation codon.

Expression of a gene can also be enhanced by extending the survival time of the mRNA or by preventing degradation of the encoded protein in the cells. An expression control sequence such as a promoter which is upstream of the pckA gene can also be identified by using a promoter search vector or gene analysis software such as GENETYX. Expression of the pckA gene can be enhanced by substituting or modifying the promoter.

Modifying an expression control sequence can be combined with increasing the copy number of the pckA gene.

A bacterial strain which is modified to decrease the activity of one or more enzymes such as lactate dehydrogenase (LDH), α-acetolactate decarboxylase (α-ALDC), alcohol dehydrogenase (ADH), pyruvate formate lyase (PFL) and phosphate acetyltransferase (PTA), in addition to increasing the expression of the pckA gene, can be more effective. The expression "modified so that lactate dehydrogenase activity is decreased" can mean that the lactate dehydrogenase activity is decreased as compared to the activity in a strain in which lactate dehydrogenase is unmodified. The lactate dehydrogenase activity per cell can be decreased to 10% or lower as compared to that of a strain in which lactate dehydrogenase is unmodified. The lactate dehydrogenase activity can also be completely deleted. The decrease of the lactate dehydrogenase activity can be confirmed by measuring the lactate dehydrogenase activity by a known method (Kanarek, L. and Hill, R. L., 1964, J. Biol. Chem., 239:4202). Specific examples of a method for producing a mutant strain of bacteria belonging to the family Enterobacteriaceae in which the lactate dehydrogenase activity is decreased include the method described in Alam, K. Y., and Clark, D. P., 1989, J. Bacteriol., 171:6213-6217, and the like.

In order to decrease or delete the activity of LDH, a mutation can be introduced into the LDH gene on the chromosome by a typical mutagenesis method. For example, the gene coding for LDH on the chromosome can be deleted, or an expression control sequence such as a promoter and/or an Shine-Dalgarno (SD) sequence can be modified by gene recombination. Furthermore, a mutation which results in an amino acid substitution (missense mutation), a stop codon (nonsense mutation), or a frame shift mutation that adds or deletes one or two nucleotides into the LDH coding on the chromosome can be introduced. Alternatively, a part of the gene, or the entire gene can be deleted (Journal of Biological Chemistry 272:8611-8617 (1997)). Furthermore, the LDH activity can also be decreased or deleted by gene disruption, for example, by mutating or deleting the coding region of the LDH gene, and replacing the normal or native LDH gene on the chromosome with the mutant LDH gene by homologous recombination or the like. Alternatively, a transposon or IS factor can be introduced into the gene.

In order to introduce a mutation that reduces or deletes the LDH activity by genetic recombination, for example, the following methods can be used. The LDH gene on the chromosome can be replaced with a mutant gene by preparing a mutant LDH gene in which a partial sequence of the LDH gene is modified so that it does not produce a functional enzyme, and transforming a bacterium with a DNA containing the mutant gene to cause homologous recombination between the mutant gene and the gene on the chromosome. Such site-specific mutagenesis based on gene substitution utilizing homologous recombination has been already reported, and includes the method of Red driven integration developed by Datsenko and Wanner (Proc. Natl. Acad. Sci. USA, 2000, vol. 97, No. 12, pp. 6640-6645), which can use a linear DNA in the Red driven integration in combination with an excision system derived from λ phage (Cho, E. H., Gumport, R. I., Gardner, J. F., J. Bacteriol., 184: 5200-5203 (2002, and WO2005/010175), and/or a plasmid containing a temperature sensitive replication origin (U.S. Pat. No. 6,303,383, Japanese Patent Laid-open No. 05-007491, WO2005/010175), and the like. Site-specific mutagenesis based on gene substitution using homologous recombination as described above can also be performed with a plasmid that is unable to replicate in the chosen host.

The LDH gene of Enterobacter aerogenes, and specifically the nucleotide sequence of the D-LDH gene (ldhA) of the Enterobacter aerogenes AJ110637 strain (FERM BP-10955), is shown in SEQ ID NO: 20. The amino acid sequence encoded by this gene is shown in SEQ ID NO: 48.

The expression "modified so that alcohol dehydrogenase activity is decreased" or "modified to decrease alcohol dehydrogenase activity" can mean that the alcohol dehydrogenase activity is decreased as compared to that of a strain in which the alcohol dehydrogenase is unmodified. The alcohol dehydrogenase activity per cell can be decreased to 10% or lower as compared to that of a strain in which the alcohol dehydrogenase is unmodified. The alcohol dehydrogenase activity can also be completely deleted. The decrease of the alcohol dehydrogenase activity can be confirmed by measuring the alcohol dehydrogenase activity by a known method (Lutstorf, U. M., Schurch, P. M. & von Wartburg, J. P., Eur. J. Biochem., 17, 497-508 (1970)). Specific examples of the method for producing a mutant strain of bacterium belonging to the family Enterobacteriaceae in which the alcohol dehydrogenase activity is decreased include the method described in Sanchez A. M. et al., 2005, Biotechnol. Prog., 21:358-365, and the like. A bacterium in which the alcohol dehydrogenase activity is decreased and expression of the pckA gene is enhanced can be obtained, for example, by disrupting the gene coding for alcohol dehydrogenase (ADH), and transforming the bacterium with a recombinant vector containing the pckA gene. However, either the modification for decreasing the ADH activity or the modification for enhancing expression of the pckA gene can be performed first. The alcohol dehydrogenase activity can be decreased by a method similar to the method for decreasing the lactate dehydrogenase activity described above.

The nucleotide sequence of the ADH gene (adhE) from the *Enterobacter aerogenes* AJ110637 strain (FERM ABP-10955) is shown in SEQ ID NO: 21, and the amino acid sequence encoded by this gene is shown in SEQ ID NO: 49.

The bacterium in which the alcohol dehydrogenase activity is decreased and expression of the pckA gene is enhanced can be obtained, for example, by disrupting the ADH gene, and transforming the bacterium with a recombinant vector containing the pckA gene, as described in the examples section. A bacterium in which the ADH activity and the LDH activity are decreased and expression of the pckA gene is enhanced can be obtained by, for example, preparing a bacterium in which an LDH gene is disrupted from a bacterium in which an ADH gene is disrupted, and transforming this bacterium with a recombinant vector containing the pckA gene, as described in the examples section.

The expression "modified so that phosphate acetyltransferase activity is decreased" or "modified to decrease phosphate acetyltransferase activity" can mean that the phosphate acetyltransferase activity is decreased as compared to that of a strain in which the phosphate acetyltransferase is unmodified. The phosphate acetyltransferase activity per cell can be decreased to 10% or lower of that of an unmodified phosphate acetyltransferase. The phosphate acetyltransferase activity can also be completely deleted. The decrease of the phosphate acetyltransferase activity can be confirmed by measuring the phosphate acetyltransferase activity by a known method (Klotzsch, H. R., Meth. Enzymol., 12, 381-386 (1969)). The bacterium in which the phosphate acetyltransferase activity is decreased and expression of the pckA gene is enhanced can be obtained by, for example, preparing a bacterium in which the PTA gene is disrupted, and transforming this bacterium with a recombinant vector containing the pckA gene. However, either the modification for decreasing the PTA activity or the modification for enhancing expression of the pckA gene can be performed first. The phosphate acetyltransferase activity can be decreased by a method similar to the method for decreasing the lactate dehydrogenase activity described above.

The nucleotide sequence of the PTA gene (pta) of the *Enterobacter aerogenes* AJ110637 strain (FERM ABP-10955) is shown in SEQ ID NO: 50, and the amino acid sequence encoded by this gene is shown in SEQ ID NO: 51. Although the first amino acid residue is indicated as Val using the universal code in these sequences, gtg can be used as the start codon in bacteria, and it is very likely to be actually Met.

The bacterium in which the ADH activity, the LDH activity and the PTA activity are decreased, and expression of the pckA gene is enhanced can be obtained, for example, by disrupting the PTA gene in a bacterium in which the ADH gene and the LDH gene are already disrupted, and transforming the bacterium with a recombinant vector containing the pckA gene, as described in the examples section.

The expression "modified so that α-acetolactate decarboxylase activity is decreased" or "modified to decrease α-acetolactate decarboxylase activity" can mean that the α-acetolactate decarboxylase activity is decreased as compared to that of a strain in which α-acetolactate decarboxylase is unmodified. The α-acetolactate decarboxylase activity per cell can be decreased to 10% or lower as compared to that of a strain in which the α-acetolactate decarboxylase is unmodified. The α-acetolactate decarboxylase activity can be completely deleted. The decrease of the α-acetolactate decarboxylase activity can also be confirmed by measuring the α-acetolactate decarboxylase activity by a known method (Juni, E. J., Biol. Chem., 195, 715-726 (1952)). The bacterium in which the α-acetolactate decarboxylase is decreased and expression of the pckA gene is enhanced can be obtained, for example, by disrupting the α-ALDC gene (aldC), and transforming the bacterium with a recombinant vector containing the pckA gene. However, either the modification for decreasing the α-ALDC activity or the modification for enhancing expression of the pckA gene can be performed first. The α-ALDC activity can be decreased by a method similar to the method for decreasing the lactate dehydrogenase activity described above.

The nucleotide sequence of the α-ALDC gene (aldC) from the *Enterobacter aerogenes* AJ110637 strain (FERM ABP-10955) is shown in SEQ ID NO: 52, and the amino acid sequence encoded by this gene is shown in SEQ ID NO: 53.

The bacterium in which the ADH activity, the LDH activity, the PTA activity and the α-ALDC activity are decreased, and expression of the pckA gene is enhanced can be obtained, for example, by disrupting the α-ALDC gene in a bacterium in which the ADH gene, the LDH gene and the PTA gene are already disrupted, and transforming the bacterium with a recombinant vector containing the pckA gene, as described in the examples section.

The expression "modified so that pyruvate formate lyase activity is decreased" or "modified to decrease pyruvate formate lyase activity is decreased" can mean that the pyruvate formate lyase activity is decreased as compared to that of a strain in which the pyruvate formate lyase is unmodified. The pyruvate formate lyase activity per cell can be decreased to 10% or lower of that of a strain in which the pyruvate formate lyase is unmodified. The pyruvate formate lyase activity can also be completely deleted. The decrease of the pyruvate formate lyase activity can be confirmed by measuring the pyruvate formate lyase activity by a known method (Knappe, J. and Blaschkowski, H. P., 1975, Meth. Enzymol., 41:508-518). The bacterium in which pyruvate formate lyase activity is decreased and expression of the pckA gene is enhanced can be obtained, for example, by disrupting the PFL gene, and transforming the bacterium with a recombinant vector containing the pckA gene. However, either the modification for decreasing the PFL activity or the modification for enhancing expression of pckA can be performed first. The pyruvate formate lyase activity can be decreased by a method similar to the method for decreasing the lactate dehydrogenase activity described above.

The nucleotide sequence of the PFL gene (pflB) from the *Enterobacter aerogenes* AJ110637 strain (FERM ABP-10955) is shown in SEQ ID NO: 54, and the amino acid sequence encoded by this gene is shown in SEQ ID NO: 55.

The bacterium in which the ADH activity, the LDH activity, the PTA activity, the α-ALDC activity and the PFL activity are decreased, and expression of the pckA gene is enhanced can be obtained, for example, by disrupting the PFL gene in a bacterium in which the ADH gene, the LDH gene, the PTA gene and the α-ALDC gene are already disrupted, and transforming this bacterium with a recombinant vector containing the pckA gene, as described in the examples section.

A bacterium modified so that the pyruvate carboxylase (PC) activity is enhanced, in addition to the enhanced expression of the pckA gene, can also be used. Enhancing the pyruvate carboxylase activity can be combined with decreasing the activities of one or more enzymes, such as lactate dehydrogenase (LDH), the α-acetolactate decarboxylase (α-ALDC), the alcohol dehydrogenase (ADH), the pyruvate formate lyase (PFL), and the phosphate acetyltransferase (PTA). The expression "modified so that pyruvate carboxylase activity is enhanced" or "modified to enhance pyruvate carboxylase activity is enhanced" can mean that the pyruvate carboxylase activity is increased as compared to that of an unmodified strain such as a wild-type strain or parent strain. The pyruvate carboxylase activity can be measured by, for example, by measuring decrease of NADH (Moss, J. & Lane, M. D., Adv. Enzymol., 35, 321-442 (1971)).

As the PC gene, a gene for which the nucleotide sequence is already determined, or a gene obtained by isolating a DNA fragment encoding a protein having the PC activity from a chromosome of a microorganism, animal, plant, or the like and determining the nucleotide sequence can be used. After the nucleotide sequence is determined, a gene synthesized on the basis of that sequence can also be used.

As the PC gene, for example, a PC gene derived from or native to a coryneform bacterium such as *Corynebacterium glutamicum* or *Brevibacterium flavum* (Peters-Wendisch, P. G. et al., 1998, Microbiology, vol. 144:915-927) (SEQ ID NO: 22) can be used. Furthermore, so long as the function of the encoded PC, that is, the characteristic concerning carbon dioxide fixation, is not substantially degraded, the PC gene can have the nucleotide sequence of SEQ ID NO: 22, but can include substitution or deletion of one or more nucleotides, insertion of one or more nucleotides, or dislocation of a portion of the nucleotide sequence, or other derivatives. A DNA that hybridizes with a DNA having the nucleotide sequence of SEQ ID NO: 22 under stringent conditions, or a DNA having a homology of, for example, 90% or more, 95% or more, or 99% or more in another example, to the nucleotide sequence of SEQ ID NO: 22 and coding for a protein having the PC activity can also be used. Examples of the stringent conditions can include conditions of washing in ordinary Southern hybridization, i.e., conditions for hybridization at salt concentrations and temperatures of 1×SSC, 0.1% SDS at 60° C., or 0.1×SSC, 0.1% SDS at 60° C. in another example.

PC genes from bacteria other than *Corynebacterium glutamicum*, as well as from other microorganisms, animals, and plants can also be used. In particular, the reported sequences of PC genes derived from microorganisms, animals and plants described below (citations are indicated in brackets), and they can be obtained by hybridization or amplification of the ORF regions by PCR in the same manner as described above.

Human [Biochem. Biophys. Res. Comm., 202, 1009-1014, (1994)]

Mouse [Proc. Natl. Acad. Sci. USA., 90, 1766-1779, (1993)]

Rat [GENE, 165, 331-332, (1995)]

Yeast: *Saccharomyces cerevisiae* [Mol. Gen. Genet., 229, 307-315, (1991)],

*Schizosaccharomyces pombe* [DDBJ Accession No.; D78170]

*Bacillus stearothermophilus* [GENE, 191, 47-50, (1997)]

*Rhizobium etli* [J. Bacteriol., 178, 5960-5970, (1996)]

The PC gene can be enhanced in the same manner as those used for enhancing expression of the pckA gene described above.

The activity of phosphoenolpyruvate carboxylase (PEPC) of the bacterium of the present invention may not be decreased or eliminated, and the gene encoding PEPC can be a wild-type gene.

<2> Method for Producing Organic Acid

An organic acid can be produced by using a bacterium that is able to produce an organic acid, and has been modified so that expression of the pckA gene is enhanced as described above. Specifically, an organic acid can be produced by allowing the bacterium, or a product obtained by processing the bacterium, to act on an organic raw material in a reaction mixture containing carbonate ions, bicarbonate ions, or carbon dioxide gas to produce the organic acid, and collecting the organic acid.

In one example of the method, by culturing the bacterium in a medium containing carbonate ions, bicarbonate ions, or carbon dioxide gas, and an organic raw material, proliferation of the bacterium and production of the organic acid occur simultaneously. In this example, the medium can be the reaction mixture. Proliferation of the bacterium and production of the organic acid can be simultaneously attained, or there can be a period during the culture when proliferation of the bacterium mainly occurs, and a period in which production of the organic acid mainly occurs.

In another example, by allowing cells to proliferate in a medium in the presence of carbonate ions, bicarbonate ions, or carbon dioxide gas, and an organic raw material, and thereby allowing the cells to act on the organic raw material in the medium or reaction mixture, an organic acid can be produced. In this example, a product obtained by processing the cells of the bacterium can also be used. Examples of the product obtained by processing cells include, for example, immobilized cells which can be obtained with acrylamide, carragheenan, or the like, disrupted cells, centrifugation supernatant of the disrupted product, fraction obtained by partial purification of the supernatant by ammonium sulfate treatment or the like.

Although the bacteria can be cultured on a solid medium such as agar medium by slant culture, bacteria previously cultured in a liquid medium (seed culture) are other examples.

As the medium used for the culture, a typical microorganism culture medium can be used. For example, a typical medium obtained by adding natural nutrients such as meat extract, yeast extract and peptone, to a composition including inorganic salts such as ammonium sulfate, potassium phosphate and magnesium sulfate can be used.

In the aforementioned first example, the carbon source that is added to the medium also serves as the organic raw material for the production of the organic acid.

In the aforementioned second example, after the culture, the cells are collected by centrifugation, membrane separation, or the like, and used for the organic acid production reaction.

The organic raw material is not particularly limited so long as it includes a carbon source which the chosen bacterium can assimilate to produce succinic acid. However, fermentable carbohydrates including carbohydrates such as galactose, lactose, glucose, fructose, glycerol, sucrose, saccharose, starch and cellulose, polyalcohols such as mannitol, xylitol and ribitol, and the like are usually used. When the organic acid is succinic acid, fumaric acid or the like can be added in order to efficiently produce succinic acid as described in Japanese Patent Laid-open No. 5-68576, and malic acid can be added instead of fumaric acid.

Furthermore, a saccharified starch solution, molasses, or the like containing the fermentable carbohydrates can also be used. The fermentable carbohydrates can be used independently or in combination. Although the concentration of the aforementioned organic raw material is not particularly limited, it is more advantageous when the concentration is as high as possible within such a range that the production of the organic acid is not inhibited. In the aforementioned first example, concentration of the organic raw material in the medium is generally in the range of 5 to 30% (w/v), or 10 to 20% (w/v) in another example. Furthermore, in the aforementioned second example, the concentration of the organic raw material in the reaction mixture is generally in the range of 5 to 30% (w/v), or 10 to 20% (w/v) in another example. Furthermore, additional organic raw material can be added as its concentration decreases as the reaction progresses.

The aforementioned reaction mixture containing carbonate ions, bicarbonate ions, or carbon dioxide gas and the organic raw material is not particularly limited, and it can be, for example, a medium for culturing bacteria, or it can be a buffer such as phosphate buffer. The reaction mixture can be an aqueous solution containing a nitrogen source, inorganic salts, and the like. The nitrogen source is not particularly limited so long as it is a nitrogen source which the chosen bacterium can assimilate to produce an organic acid, and specific examples include various organic or inorganic nitrogen compounds such as ammonium salts, nitrates, urea, soybean hydrolysate, casein degradation products, peptone, yeast extract, meat extract, and corn steep liquor. Examples of the inorganic salts include various phosphates, sulfates, and metallic salts such as those of magnesium, potassium, manganese, iron, and zinc. If necessary, growth-promoting factors including vitamins such as biotin, pantothenic acid, inositol, and nicotinic acid, nucleotides, amino acids and the like can be added. In order to suppress foaming at the time of the reaction, an appropriate amount of commercially available antifoam can be added to the medium.

The pH of the reaction mixture can be adjusted by adding sodium carbonate, sodium bicarbonate, potassium carbonate, potassium bicarbonate, magnesium carbonate, sodium hydroxide, calcium hydroxide, magnesium hydroxide, or the like. Since the pH for the reaction is usually 5 to 10, or 6 to 9.5, the pH of the reaction mixture is adjusted to be within the aforementioned range with an alkaline substance, carbonate, urea, or the like even during the reaction, if needed.

The reaction mixture can include water, a buffer, a medium, or the like, but media is a particular example. The media can contain, for example, the aforementioned organic raw material, and carbonate ions, bicarbonate ions, or carbon dioxide gas, and the reaction can be performed under anaerobic conditions. The carbonate or bicarbonate ions can be supplied from magnesium carbonate, sodium carbonate, sodium bicarbonate, potassium carbonate, or potassium bicarbonate, which can also be used as a neutralizing agent. However, if necessary, carbonate or bicarbonate ions can also be supplied from carbonic acid or bicarbonic acid or salts thereof or carbon dioxide gas. Specific examples of the salts of carbonic acid or bicarbonic acid include, for example, magnesium carbonate, ammonium carbonate, sodium carbonate, potassium carbonate, ammonium bicarbonate, sodium bicarbonate, potassium bicarbonate, and the like. Carbonate ions or bicarbonate ions can be added at a concentration of 0.001 to 5 M, 0.1 to 3 M in another example, or 1 to 2 M in another example. When carbon dioxide gas is present, it can be present in an amount of 50 mg to 25 g, 100 mg to 15 g in another example, or 150 mg to 10 g in another example, per liter of the solution.

The optimal growth temperature of the bacterium is generally in the range of 25 to 40° C. The reaction temperature is generally in the range of 25 to 40° C., or in the range of 30 to 37° C. in another example. The amount of bacterial cells in the reaction mixture can be, although it is not particularly limited, 1 to 700 g/L, 10 to 500 g/L in another example, or 20 to 400 g/L in another example. The reaction time can be 1 to 168 hours, or 3 to 72 hours in another example. The reaction can be performed batchwise or on a column.

The bacterial culture can be performed under aerobic conditions. Alternatively, the organic acid production reaction can be performed under aerobic conditions, microaerobic conditions or anaerobic conditions. For the reaction under microaerobic conditions or anaerobic conditions, the reaction can be performed in a sealed reaction vessel without aeration, by supplying an inert gas such as nitrogen gas to the reaction mixture, by supplying an inert gas containing carbon dioxide gas to the reaction mixture, and the like.

The organic acid that accumulates in the reaction mixture (culture medium) can be separated and purified from the reaction mixture in a conventional manner. Specifically, solids such as bacterial cells can be removed by centrifugation, filtration, or the like, and then the resulting solution can be desalted with an ion exchange resin or the like. The organic acid can be separated and purified from the solution by crystallization or column chromatography.

Furthermore, when the target organic acid is succinic acid, after succinic acid is produced, a polymerization reaction can be carried out by using the succinic acid as a raw material to produce a polymer containing succinic acid. In recent years, with the increase of environmentally friendly industrial products, polymers prepared from raw materials of plant origin have been attracting attention. Succinic acid can be converted into polymers such as polyesters and polyamides and used (Japanese Patent Laid-open No. 4-189822). Specific examples of succinic acid-containing polymers include succinic acid polyesters obtainable by polymerizing a diol such as butanediol and ethylene glycol, and succinic acid, succinic acid polyamides obtainable by polymerizing a diamine such as hexamethylenediamine and succinic acid, and the like. In addition, succinic acid and succinic acid-containing polymers, and compositions containing these can be used as food additives, pharmaceutical agents, cosmetics, and the like.

EXAMPLES

Hereinafter, the present invention will be explained more specifically with reference to the following non-limiting examples.

Example 1

1-1> Acquisition of the Threonine Operon Promoter Fragment from the *Escherichia coli* MG1655 Strain The entire genomic nucleotide sequence of *Escherichia coli* (*Escherichia coli* K-12 strain) has already been elucidated (Genbank Accession No. U00096, Science, 277, 1453-1474 (1997)). On the basis of this sequence, the promoter region of the threonine operon (thrLABC) was amplified by PCR using a synthetic oligonucleotide having a SacI site (SEQ ID NO: 1) as the 5' primer, a synthetic oligonucleotide (SEQ ID NO: 2) as the 3' primer, and genomic DNA from the *Escherichia coli* MG1655 strain (ATCC 47076, ATCC 700926) as the template. As a result, the threonine operon promoter fragment (A) (SEQ ID NO: 3) was obtained.

<1-2> Acquisition of a Phosphoenolpyruvate Carboxykinase Gene Fragment from the *Actinobacillus succinogenes* 130Z Strain (ATCC 55618)

The entire genomic nucleotide sequence of the *Actinobacillus succinogenes* 130Z strain has also already been elucidated (GenBank Accession No. CP000746). Primers were designed based on the nucleotide sequence of the gene coding for PEPCK (gene name: pckA), and used to perform PCR amplification. PCR was performed by using the synthetic oligonucleotide shown in SEQ ID NO: 4 as the 5' primer, the synthetic oligonucleotide having an SacI site shown in SEQ ID NO: 5 as the 3' primer, and the genomic DNA from the *Actinobacillus succinogenes* 130Z strain as the template to obtain a pckA gene fragment (B) (SEQ ID NO: 6).

<1-3> Construction of the Plasmid for pckA Gene Amplification

PCR was performed by using the fragments (A) and (B) as templates, and the primers of SEQ ID NOS: 1 and 5 having the SalI site to obtain a gene fragment (C) consisting of the fragments (A) and (B) ligated to each other. This gene fragment (C) was treated with the restriction enzyme SacI, purified, and the product was ligated with the plasmid vector pSTV28 (Takara Bio) which had been digested with the restriction enzyme SacI to construct a plasmid pSTV28::Pthr::pckA for pckA amplification.

<1-4> Preparation of a pckA-amplified Strain from the *Enterobacter aerogenes* AJ110637 Strain (FERM BP-10955)

The *Enterobacter aerogenes* AJ110637 strain (FERM BP-10955, see Reference Example 1) was transformed with pSTV28::Pthr::pckA obtained above, and pSTV28 by the electric pulse method, applied to an LB agar medium containing 40 μg/ml of chloramphenicol, and cultured at 37° C. for about 18 hours. The colonies that appeared were purified, and plasmids were extracted in a conventional manner to confirm that the target plasmids were present. The obtained strains were designated *Enterobacter aerogenes* AJ110637 pSTV28::Pthr::pckA and *Enterobacter aerogenes* AJ110637 pSTV28, respectively.

Example 2

Effect of pckA Amplification in a Succinic Acid-Producing Strain from *Enterobacter* Bacterium The *Enterobacter aerogenes* AJ110637 pSTV28::Pthr::pckA and the *Enterobacter aerogenes* AJ110637 pSTV28 were each uniformly applied to an LB plate containing 40 μg/ml of chloramphenicol, and cultured at 37° C. for 16 hours. Then, each plate was put into Anaeropack (for compromised culture of anaerobes, Mitsubishi Gas Chemical, product number A-04), and incubated at 37° C. for 16 hours under anaerobic conditions. The cells which appeared on the plate were washed with 0.8% brine and suspended so that the resulting cell suspension has an OD=1.0 (600 nm) after 51-times dilution. This cell suspension in a volume of 100 μl, and a production medium in a volume of 1.3 ml in which dissolved gases in the medium were replaced with carbon dioxide beforehand, were put into a 1.5-ml volume microtube, and the cells were cultured at 31.5° C. for 10 hours with shaking. The composition of the production medium is shown below.

Composition of organic acid production medium for *Enterobacter* bacteria:

| Mixture A: | |
|---|---|
| Glucose | 40 g/L (final concentration) |
| Magnesium sulfate heptahydrate | 1 g/L |

| Mixture B: | |
|---|---|
| Ammonium sulfate | 1 g/L |
| Potassium dihydrogenphosphate | 1 g/L |
| Manganese sulfate pentahydrate | 10 mg/L |
| Iron sulfate heptahydrate | 10 mg/L |
| Yeast Extract | 2 g/L |
| Biotin | 1 mg/L |
| (adjusted to pH 5.5 with KOH) | |

| C: | |
|---|---|
| Calcium carbonate (Japanese Pharmacopoeia) | 50 g/L |

The ingredients of the A and B mixtures were sterilized at 115° C. for 10 minutes by autoclaving, the calcium carbonate (C) was sterilized at 180° C. for 3 hours with dry heat, and then left to cool, and A, B, and C were mixed.

After the culture, the amount of the organic acid which had accumulated in the medium was analyzed by liquid chromatography. Two Shim-pack SCR-102H (Shimadzu) columns connected in series were used, and the sample was eluted at 50° C. with 5 mM p-toluenesulfonic acid. The eluate was neutralized with 20 mM Bis-Tris aqueous solution containing 5 mM p-toluenesulfonic acid and 100 μM EDTA, and the organic acid was quantified by measuring electric conductivity with CDD-10AD (Shimadzu). The amount of consumed glucose, change in OD, and the accumulated organic acid and yield based on the consumed glucose determined after 24 hours are shown in Table 1.

TABLE 1

| | pSTV28 | pSTV28::Pthr::pckA |
|---|---|---|
| Consumed glucose (g/L) | 16.6 (±0.78) | 13.6 (±0.13) |
| ΔOD (600 nm) | 1.54 (±0.08) | 2.27 (±0.07) |
| Accumulated malic acid (g/L) | 0.04 (±0.01) | 0.20 (±0.02) |
| Yield of malic acid based on consumed glucose (%) | 0.24 (±0.05) | 1.45 (±0.15) |
| Accumulated succinic acid (g/L) | 0.63 (±0.01) | 2.97 (±0.13) |
| Yield of succinic acid based on consumed glucose (%) | 3.80 (±0.12) | 21.8 (±0.75) |

The pckA gene-amplified strain, *Enterobacter aerogenes* AJ110637 pSTV28::Pthr::pckA provided markedly improved accumulation of malic acid and succinic acid and yields thereof based on consumed glucose as compared to the control, *Enterobacter aerogenes* AJ110637 pSTV28.

Example 3

<3-1> Construction of adhE-deficient Strain of *Enterobacter aerogenes* AJ110637

When *Enterobacter aerogenes* AJ110637 is grown in a medium containing a sugar source, it produces a marked amount of ethanol. Therefore, adhE coding for alcohol dehydrogenase was deleted to suppress the production of ethanol.

A gene fragment for deletion of adhE was prepared by PCR using a plasmid pMW-attL-Tc-attR (WO2005/010175) as the template, and the oligonucleotides of SEQ ID NOS: 18 and 19 as primers. pMW118-attL-Tc-attR was obtained by inserting the attL and attR genes, which are the attachment sites of λ phage, and the Tc gene, which is an antibiotic resistance gene, into pMW118 (Takara Bio), in the following order: attL-Tc-attR (see Reference Example 3). By PCR described above, a gene fragment containing a tetracycline resistance gene, attL and attR sites of λ phage at the both ends of tetracycline gene, and 60 bp of the upstream sequence and 59 bp of the downstream sequence of the adhE gene added to the outer ends of the λ phage sequences was amplified. This fragment was purified by using Wizard PCR Prep DNA Purification System (Promega).

Then, the *Enterobacter aerogenes* AJ110637 strain was transformed with RSF-Red-TER (see FIG. 1, Reference Example 2) to obtain the *Enterobacter aerogenes* AJ110637/RSF-Red-TER strain. This strain was cultured overnight in LB medium containing 40 μg/mL of chloramphenicol. Then, the culture medium was inoculated in a 1/100 volume to 50 mL of LB medium containing 40 μg/mL of chloramphenicol and 0.4 mM isopropyl-β-D-thiogalactopyranoside, and a second culture was performed at 31° C. for 4 hours. The cells were collected, washed three times with ice-cooled 10% glycerol, and finally suspended in 0.5 mL of 10% glycerol. The suspended cells were used as competent cells, and 500 ng of the PCR fragment prepared in the above section was introduced into the cells by using GENE PULSER II (BioRad) under the following conditions: a field strength of 20 kV/cm, capacitor capacity of 25 μF, and resistance of 200 μl Ice-cooled SOC medium (20 g/L of Bacto tryptone, 5 g/L of yeast extract, 0.5 g/L of NaCl, 10 g/L of glucose) was added to the cell suspension, and culture was performed at 31° C. for 2 hours with shaking. Then, the culture was applied to a LB plate containing 25 μg/mL of tetracycline. The colonies that appeared were purified on the same plate, and then it was confirmed by PCR that the adhE gene had been replaced with the tetracycline resistance gene.

Then, in order to eliminate the RSF-Red-TER plasmid from each recombinant strain obtained as described above, the strains were applied to an LB medium containing 10% sucrose and 1 mM IPTG, and cultured overnight at 37° C. A strain lacking chloramphenicol resistance was selected as AJ110637ΔadhE from the colonies that appeared.

<3-2> Construction of a pckA-amplified Strain from *Enterobacter aerogenes* AJ110637ΔadhE The *Enterobacter aerogenes* AJ110637ΔadhE strain obtained above was transformed with the pSTV28::Pthr::pckA plasmid for amplification of pckA and pSTV28, applied to a LB agar medium containing 40 μg/ml of chloramphenicol and 25 μg/ml of tetracycline, and cultured at 37° C. for about 18 hours. The colonies that appeared were purified, and plasmids were extracted in a conventional manner to confirm that the target plasmids were present. The obtained strains were designated *Enterobacter aerogenes* AJ110637ΔadhE+pSTV28::Pthr::pckA and *Enterobacter aerogenes* AJ110637ΔadhE+pSTV28, respectively.

<3-3> Effect of pckA Amplification in a Succinic Acid-Producing Strain of *Enterobacter* Bacterium which is Deficient in Alcohol Dehydrogenase Succinic acid-producing abilities of *Enterobacter aerogenes* AJ110637ΔadhE+pSTV28::Pthr::pckA and *Enterobacter aerogenes* AJ110637ΔadhE+pSTV28 were compared by using the same evaluation method as outlined above. The results obtained after 45 hours are shown in Table 2.

TABLE 2

|  | ΔadhE+pSTV28 | ΔadhE+pSTV28::Pthr::pckA |
|---|---|---|
| Consumed glucose (g/L) | 3.29 (±0.43) | 7.45 (±0.95) |
| ΔOD (600 nm) | 0.30 (±0.10) | 0.85 (±0.18) |
| Accumulated succinic acid (g/L) | 0.40 (±0.10) | 5.19 (±0.69) |
| Yield of succinic acid based on consumed glucose (%) | 11.95 (±1.48) | 69.61 (±0.39) |

The pckA gene-amplified strain, *Enterobacter aerogenes* AJ110637ΔadhE+pSTV28::Pthr::pckA, showed markedly increased accumulation of succinic acid and yield thereof based on consumed glucose compared with *Enterobacter aerogenes* AJ110637ΔadhE+pSTV28 as compared to the control.

Example 4

<4-1> Construction of a Strain from *Enterobacter aerogenes* AJ110637ΔadhE which is Deficient in the Acetic Acid, Lactic Acid, 2,3-butanediol, and Formic Acid Synthesis Genes If AJ110637ΔadhE is allowed to grow in a medium containing a sugar source, acetic acid, lactic acid, 2,3-butanediol, and formic acid are produced in the medium. Therefore, a strain with an improved ability to produce succinic acid was constructed by deleting the synthesis pathways of these substances.

<4-2> Deletion of an Antibiotic Resistance Gene from AJ110637ΔadhE

The RSF-int-xis plasmid was used to remove the tetracycline resistance gene from AJ110637ΔadhE (refer to Reference Example 4). RSF-int-xis was introduced into the gene-disrupted strain by the electric pulse method, and the transformant was added to an LB medium containing 40 μg/ml of chloramphenicol, and cultured at 30° C. to obtain a strain containing RSF-int-xis. This strain was purified on LB medium containing 40 μg/ml of chloramphenicol and 1 mM IPTG, and plural single colonies were obtained. The obtained strains were added to a medium containing 25 μg/ml of tetracycline, and cultured overnight at 37° C. It was confirmed that the strains did not grow. Thus, these strains were confirmed to be lacking the antibiotic resistance gene. Then, in order to eliminate the RSF-int-xis plasmid from the strains, they were added to LB medium containing 10% sucrose and 1 mM IPTG, and cultured overnight at 37° C. A strain without chloramphenicol resistance was selected from the colonies that appeared, and used to delete the biosynthetic pathways of acetic acid, lactic acid, 2,3-butanediol and formic acid.

<4-3> Construction of a D-lactate Dehydrogenase-Deficient Strain

Lactic acid production can be suppressed by deleting lactate dehydrogenase. The ldhA gene, which encodes D-lactate dehydrogenase, was disrupted as follows. By performing PCR using the oligonucleotide primers shown in SEQ ID NOS: 56 and 57, and the template pMW-attL-Km-attR, AJ110637ΔadhEΔldhA was constructed from AJ110637ΔadhE in which the antibiotic resistance gene was deleted in the same manner as that of Example 3 described above. This strain was designated ES02.

<4-4> Construction of a Strain Deficient in Phosphate Acetyltransferase

Production of acetic acid can be suppressed by deleting phosphate acetyltransferase. The pta gene coding for phosphate acetyltransferase was disrupted as follows. By performing PCR using the oligonucleotides shown in SEQ ID NOS: 58 and 59 and pMW-attL-Km-attR as a template, AJ110637ΔadhEΔldhAΔpta was constructed from AJ110637ΔadhEΔldhA, in which the antibiotic resistance gene was deleted in the same manner as that of Example 3 mentioned above. This strain was designated ES03.

<4-5> Construction of a Strain Deficient in α-acetolactate Decarboxylase

Production of 2,3-butanediol can be suppressed by deleting α-acetolactate decarboxylase. The aldC gene coding for α-acetolactate decarboxylase was disrupted as follows. By performing PCR using the oligonucleotides shown in SEQ ID NOS: 60 and 61 and pMW-attL-Km-attR as a template, AJ110637ΔadhEΔldhAΔptaΔaldC was constructed from AJ110637ΔadhEΔldhAΔpta, in which the antibiotic resistance gene was deleted in the same manner as that of Example 3 described above. This strain was designated ES04.

<4-6> Construction of a Strain Deficient in Pyruvate Formate Lyase

Production of formic acid can be suppressed by deleting pyruvate formate lyase. The pflB gene coding for pyruvate formate lyase was disrupted as follows. By performing PCR using the oligonucleotides shown in SEQ ID NOS: 62 and 63 and pMW-attL-Km-attR as a template, AJ110637ΔadhEΔldhAΔptaΔaldCΔpflB was constructed from AJ110637ΔadhEΔldhAΔptaΔaldC, in which the antibiotic resistance gene was deleted in the same manner as that of Example 3 mentioned above. This strain was designated ES05.

Example 5

The Effect of Amplifying pckA on Succinic Acid Fermentation in the Various Deficient Strains Each of the ES02, ES03, ES04 and ES05 strains obtained above was transformed with pSTV28::Pthr::pckA and pSTV28 by the electric pulse method, applied to an LB agar medium containing 40 μg/ml of chloramphenicol, and cultured at 37° C. for about 18 hours. The colonies that appeared were purified, and plasmids were extracted in a conventional manner to confirm that the target plasmids were introduced. The obtained strains were designated ES02/pSTV28, ES02/pSTV28::Pthr::pckA, ES03/pSTV28, ES03/pSTV28::Pthr::pckA, ES04/pSTV28, ES04/pSTV28::Pthr::pckA, ES05/pSTV28, and ES05/pSTV28::Pthr::pckA, respectively.

The aforementioned strains were each inoculated into 4 ml of a seed medium containing 40 mg/L of chloramphenicol, and cultured at 31.5° C. for 16 hours in a test tube with shaking. Then, 4 ml of a glucose-containing production medium was added to the culture, the test tube was closed with a silicone stopper, and culture was performed at 31.5° C. for 24 hours with shaking. In this evaluation method, the inside of test tube was made to be under an anaerobic condition by the consumption of glucose. Therefore, the yield of succinic acid based on the consumed glucose is determined by combining the amount of consumed glucose used to form succinic acid with the amount of glucose necessary to establish the anaerobic conditions. The compositions of the seed medium and the glucose-containing production medium are shown below.

The composition of the organic acid production medium for *Enterobacter* bacteria, test tube evaluation

| Seed medium: | |
|---|---|
| Bacto tryptone | 20 g/L |
| | (final concentration) |
| Yeast Extract | 10 g/L |
| Sodium chloride | 10 g/L |

These were autoclaved at 120° C. for 10 minutes.

| Glucose-containing production medium: | |
|---|---|
| Glucose | 100 g/L |
| | (final concentration) |
| Calcium carbonate | 100 g/L |
| (Japanese Pharmacopoeia) | |

The glucose solution was autoclaved at 120° C. for 10 minutes, and the calcium carbonate was sterilized at 180° C. for 3 hours with dry heat. These were then left to cool and mixed.

After the culture, the amount of the organic acid which had accumulated in the medium was analyzed by liquid chromatography. Two Shim-pack SCR-102H (Shimadzu) were connected in series as the column, and a sample was eluted at 50° C. with 5 mM p-toluenesulfonic acid. The eluate was neutralized with 20 mM Bis-Tris aqueous solution containing 5 mM p-toluenesulfonic acid and 100 μM EDTA, and the organic acid was quantified by measuring electric conductivity with CDD-10AD (Shimadzu). The amount of consumed glucose, OD, accumulated organic acid, and yield based on the consumed glucose determined after 24 hours are shown in Table 3.

TABLE 3

| Strain | OD (600 nm) | Consumed glucose (g/L) | Accumulated succinic acid (g/L) | Yield of succinic acid based on consumed glucose (%) |
|---|---|---|---|---|
| ES02/pSTV28 | 7.03 (±0.47) | 4.35 (±0.25) | 0.03 (±0.06) | 0.72 (±1.44) |
| ES02/pSTV28::Pthr::pckA | 7.26 (±0.54) | 6.50 (±1.05) | 1.63 (±0.38) | 25.04 (±2.61) |
| ES03/pSTV28 | 7.30 (±0.68) | 8.93 (±0.30) | 0.36 (±0.04) | 4.03 (±0.44) |
| ES03/pSTV28::Pthr::pckA | 9.64 (±0.72) | 20.54 (±1.19) | 5.80 (±0.11) | 28.22 (±1.14) |
| ES04/pSTV28 | 7.65 (±0.37) | 11.18 (±1.15) | 0.46 (±0.03) | 4.30 (±0.42) |

TABLE 3-continued

| Strain | OD (600 nm) | Consumed glucose (g/L) | Accumulated succinic acid (g/L) | Yield of succinic acid based on consumed glucose (%) |
|---|---|---|---|---|
| ES04/pSTV28::Pthr::pckA | 8.14 (±0.40) | 18.76 (±0.86) | 7.20 (±0.29) | 38.44 (±2.46) |
| ES05/pSTV28 | 8.18 (±0.11) | 11.12 (±0.71) | 2.02 (±0.48) | 18.23 (±4.65) |
| ES05/pSTV28::Pthr::pckA | 8.97 (±0.27) | 15.47 (±0.36) | 8.23 (±0.33) | 53.17 (±1.41) |

Accumulation of succinic acid and yield based on consumed glucose were markedly increased by the pckA amplification in all the ES02, ES03, ES04 and ES05 strains.

Reference Example 1

Acquisition of Succinic Acid-Producing Bacterium Belonging to Genus *Enterobacter*

The *Enterobacter aerogenes* AJ110637 strain was obtained from soil at the seashore of Susuki Kaigan, Makinohara-shi, Shizuoka-ken on March, 2006 by cumulative liquid culture using glycerol as the carbon source. The full-length 16S rDNA sequence was then determined, and a homology of 99.9% to that of the *Enterobacter aerogenes* NCTC 10006 strain was found. Moreover, also in a physiological test using an API kit, the strain showed results similar to the prototype species of *Enterobacter aerogenes*, and therefore the obtained isolated strain was identified as *Enterobacter aerogenes*.

Reference Example 2

Construction of the Helper Plasmid RSF-Red-TER

Figure 2:
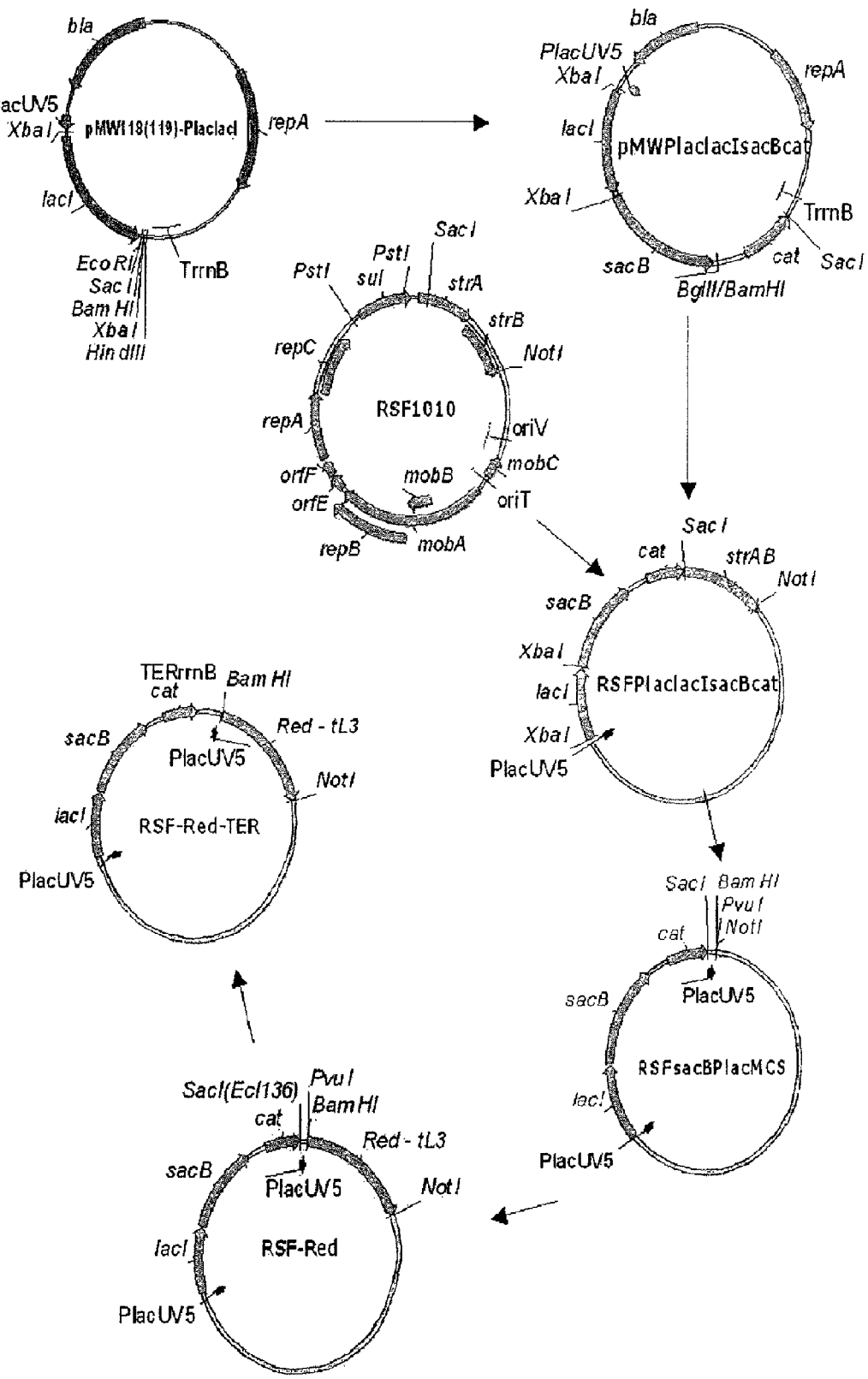
FIG. 2 shows the construction scheme of the helper plasmid RSF-Red-TER.

The scheme for constructing the helper plasmid RSF-Red-TER shown in FIG. 2.

As the first step of the construction, an RSFsacBPlacMCS vector was designed. For this purpose, DNA fragments containing the cat gene of the pACYC184 plasmid and the structural region of the sacB gene of *Bacillus subtilis* were amplified by PCR using the oligonucleotides of SEQ ID NOS: 25 and 26, and 27 and 28, respectively. These oligonucleotides contain BglII, SadI, XbaI and BamHI restriction enzyme sites, which are required and convenient for further cloning, in the 5' end regions, respectively. The obtained sacB fragment of 1.5 kb was cloned into the previously obtained pMW119-$P_{lac}$lacI vector at the XbaI-BamHI site. This vector was constructed in the same manner as that described for the pMW118-$P_{lac}$lacI vector (Skorokhodova, A. Y. et al, 2004, Biotekhnologiya (Rus), 5:3-21). However, this vector contains a polylinker moiety derived from pMW219 instead of the pMW218 plasmid.

Then, the aforementioned cat fragment of 1.0 kb was treated with BglII and SadI, and cloned into the RSF-$P_{lac}$lacIsacB plasmid which had been obtained in the previous step at the BamHI-SacI site. pMW-$P_{lac}$lacIsacBcat contains the PlacUV5-lacI-sacB-cat fragment. In order to subclone this fragment into the RSF1010 vector, pMW-$P_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from a 1% agarose gel, and ligated with the RSF1010 vector which had been treated with PstI and SacI. *Escherichia coli* TG1 was transformed with the ligation mixture, and plated on LB medium containing chloramphenicol (50 mg/L). The plasmids isolated from the grown clones were analyzed with restriction enzymes to obtain an RSFsacB plasmid. In order to construct an RSFsacBP$_{lac}$MCS vector, a DNA fragment containing the P$_{lacUV5}$ promoter was amplified by PCR using the oligonucleotides of SEQ ID NOS: 29 and 30 as primers and the pMW119-P$_{lac}$lacI plasmid as the template. The obtained fragment of 146 bp was digested with SacI and NotI, and ligated with the SacI-NotI large fragment of the RSFsacB plasmid. Then, by PCR using the oligonucleotides of SEQ ID NOS: 31 and 32 as primers, and the pKD46 plasmid (Datsenko, K. A., Wanner, B. L., 2000, Proc. Natl. Acad. Sci. USA, 97, 6640-6645) as the template, a DNA fragment of 2.3 kb containing the λRedαβγ genes and the transcription terminator tL3 was amplified. The obtained fragment was cloned into the RSFsacBP$_{lac}$MCS vector at the PvuI-NotI site. In this way, the RSFRed plasmid was designed.

In order to eliminate read-through transcription of the Red genes, a ρ-dependent transcription terminator from the rrnB operon of *Escherichia coli* was inserted at a position between the cat gene and the P$_{lacUV5}$ promoter. For this purpose, a DNA fragment containing the P$_{lacUV5}$ promoter and the TrrnB terminator was amplified by PCR using the oligonucleotides of SEQ ID NOS: 33 and 34 as primers and the chromosome of *Escherichia coli* BW3350 as the template. These obtained fragments were treated with KpnI and ligated. Then, the 0.5 kb fragment containing both P$_{lacUV5}$ sand TrrnB was amplified by PCR using the oligonucleotides of SEQ ID NOS: 35 and 36 as primers. The obtained DNA fragment was digested with EcoRI, blunt-ended by a treatment with DNA polymerase I Klenow fragment, digested with BamHI, and ligated with the Ecl136II-BamHI large fragment of the RSFsacBPlacMCS vector. The obtained plasmid was designated RSF-Red-TER.

Reference Example 3

Construction of pMW118-(λattL-Km$^r$-λattR) plasmid

A pMW118-(λattL-Km$^r$-λattR) plasmid was constructed from the pMW118-attL-Tc-attR plasmid by substituting the kanamycin resistance gene of the pUC4K plasmid for the tetracycline resistance marker gene. For this purpose, the EcoRI-HindIII large fragment of the pMW118-attL-Tc-attR plasmid was ligated with two fragments of the pUC4K plasmid, HindIII-PstI (676 bp) and EcoRI-HindIII (585 bp) fragments. pMW118-attL-Tc-attR serving as the basic structure was obtained by ligating the following four fragments.

Construction of the pMW118-attL-Tc-attR Plasmid

1) The BglII-EcoRI fragment (114 bp) which includes attL (SEQ ID NO: 37) was obtained by PCR amplification of the region corresponding to attL from the *Escherichia coli* W3350 (containing λ prophage) chromosome using the primers P1 and P2 (SEQ ID NOS: 35 and 36) (these primers contained the subsidiary recognition sites for BglII and EcoRI).

2) The PstI-HindIII fragment (182 bp) which includes attR (SEQ ID NO: 40) was obtained by PCR amplification of the region corresponding to attR from the *Escherichia coli* W3350 (containing λ prophage) chromosome using the primers P3 and P4 (SEQ ID NOS: 38 and 39) (these primers contained the subsidiary recognition sites for PstI and HindIII).

3) The BglII-HindIII large fragment (3916 bp) of pMW118-ter_rrnB. The plasmid pMW118-ter_rrnB was obtained by ligation of the following three DNA fragments:

The large DNA fragment (2359 bp) which includes the AatII-EcoRI fragment of pMW118 that was obtained by digesting pMW118 with EcoRI, treating with DNA polymerase I Klenow fragment, and then digesting with AatII;

The small AatII-BglII fragment (1194 bp) of pUC19 which includes the bla gene for ampicillin resistance ($Ap^R$) was obtained by PCR amplification of the corresponding region of the pUC19 plasmid using the primers P5 and P6 (SEQ ID NOS: 41 and 42) (these primers contained the subsidiary recognition sites for PstI, AatII and BglII);

The small BglII-PstI fragment (363 bp) of the transcription terminator ter_rrnB, which was obtained by PCR amplification of the corresponding region of the *Escherichia coli* MG1655 chromosome using the primers P7 and P8 (SEQ ID NOS: 43 and 44) (these primers contained the subsidiary recognition sites for PstI, BglII and PstI).

4) The small EcoRI-PstI fragment (1388 bp) (SEQ ID NO: 45) of pML-Tc-ter_thrL which includes the tetracycline resistance gene and the ter_thrL transcription terminator. The plasmid pML-Tc-ter_thrL was obtained by the following two steps:

the pML-ter_thrL plasmid was obtained by digesting the pML-MCS plasmid (Mashko, S. V. et al., 2001, Biotekhnologiya (in Russian), no. 5, 3-20) with XbaI and BamHI, followed by ligation of the large fragment (3342 bp) with the XbaI-BamHI fragment (68 bp) carrying ter_thrL terminator obtained by PCR amplification of the corresponding region of the *Escherichia coli* MG1655 chromosome using the primers P9 and P10 (SEQ ID NOS: 46 and 47) (these primers contained the subsidiary recognition sites for PstI, XbaI and BamHI);

the pML-Tc-ter_thrL plasmid was obtained by digesting the pML-ter_thrL plasmid with KpnI and XbaI, followed by treatment with Klenow fragment of DNA polymerase I and ligation with the small EcoRI-Van91I fragment (1317 bp) of pBR322 which includes the tetracycline resistance gene (pBR322 was digested with EcoRI and Van91I and then treated with DNA polymerase I Klenow fragment).

Reference Example 4

Construction of Plasmid RSF-int-xis for Eliminating an Antibiotic Resistance Gene RSF-int-xis was constructed to eliminate the antibiotic resistance gene from the plasmid used to disrupt the gene from the gene-disrupted strain. pMW-intxis-ts was used for the construction. pMW-intxis-ts carries the gene coding for the integrase (Int) of λ phage, the gene coding for excisionase (Xis), and has a temperature-sensitive replication origin (WO2007/037460, Japanese Patent Laid-open No. 2005-058827).

A DNA fragment which includes the intxis region was amplified by PCR using primer intxis_f (SEQ ID NO: 66), primer intxis_R (SEQ ID NO: 67), and pMW-intxis-ts as the template. The obtained DNA fragment was digested with NotI and PvuI, and ligated with the large fragment of the RSF-Red-TER plasmid which had been digested with NotI and PvuI. The obtained plasmid was designated RSF-int-xis.

EXPLANATION OF SEQUENCE LISTING

SEQ ID NO: 1: Primer for amplification of threonine promoter

SEQ ID NO: 2: Primer for amplification of threonine promoter

SEQ ID NO: 3: Threonine promoter gene fragment

SEQ ID NO: 4: Primer for amplification of pckA gene of *Actinobacillus succinogenes*

SEQ ID NO: 5: Primer for amplification of pckA gene of *Actinobacillus succinogenes*

SEQ ID NO: 6: Gene sequence of pckA of *Actinobacillus succinogenes* ATCC 55618 strain SEQ ID NO: 7: Amino acid sequence of pckA of *Actinobacillus succinogenes* ATCC 55618 strain SEQ ID NO: 8: Gene sequence of pckA of *Haemophilus influenzae* 86-028NP strain SEQ ID NO: 9: Amino acid sequence of pckA of *Haemophilus influenzae* 86-028NP strain SEQ ID NO: 10: Gene sequence of pckA of *Pasteurella multocida* subsp. *multocida* str. PM70 strain SEQ ID NO: 11: Amino acid sequence of pckA of *Pasteurella multocida* subsp. *multocida* str. PM70 strain SEQ ID NO: 12: Gene sequence of pckA of *Mannheimia succiniciproducens* MBEL55E strain SEQ ID NO: 13: Amino acid sequence of pckA of *Mannheimia succiniciproducens* MBEL55E strain SEQ ID NO: 14: Gene sequence of pckA of *Yersinia pseudotuberculosis* IP 32953 strain SEQ ID NO: 15: Amino acid sequence of pckA of *Yersinia pseudotuberculosis* IP 32953 strain SEQ ID NO: 16: Gene sequence of pckA of *Vibrio cholerae* 623-39

SEQ ID NO: 17: Amino acid sequence of pckA of *Vibrio cholerae* 623-39

SEQ ID NO: 18: Primer for deletion of adhE

SEQ ID NO: 19: Primer for deletion of adhE

SEQ ID NO: 20: Gene sequence of ldhA of *Enterobacter aerogenes* AJ110637

SEQ ID NO: 21: Gene sequence of adhE of *Enterobacter aerogenes* AJ110637

SEQ ID NO: 22: Nucleotide sequence of PC gene coding for pyruvate carboxylase of *Brevibacterium fluvum*

SEQ ID NO: 23: Amino acid sequence of pyruvate carboxylase of *Brevibacterium fluvum*

SEQ ID NO: 24: Consensus sequence of PEPCK

SEQ ID NO: 25: Primer for amplification of cat gene

SEQ ID NO: 26: Primer for amplification of cat gene

SEQ ID NO: 27: Primer for amplification of sacB gene

SEQ ID NO: 28: Primer for amplification of sacB gene

SEQ ID NO: 29: Primer for amplification of DNA fragment containing $P_{lacUV5}$ promoter SEQ ID NO: 30: Primer for amplification of DNA fragment containing $P_{lacUV5}$ promoter SEQ ID NO: 31: Primer for amplification of DNA fragment containing λRedαβγ genes and tL3

SEQ ID NO: 32: Primer for amplification of DNA fragment containing λRedαβγ genes and tL3

SEQ ID NO: 33: Primer for amplification of DNA fragment containing $P_{lacUV5}$ promoter and TrrnB SEQ ID NO: 34: Primer for amplification of DNA fragment containing P$_{lacUV5}$ promoter and TrrnB
SEQ ID NO: 35: Primer for amplification of attL
SEQ ID NO: 36: Primer for amplification of attL
SEQ ID NO: 37: Nucleotide sequence of attL
SEQ ID NO: 38: Primer for amplification of attR
SEQ ID NO: 39: Primer for amplification of attR
SEQ ID NO: 40: Nucleotide sequence of attR
SEQ ID NO: 41: Primer for amplification of DNA fragment containing bla gene
SEQ ID NO: 42: Primer for amplification of DNA fragment containing bla gene
SEQ ID NO: 43: Primer for amplification of DNA fragment containing ter_rrnB
SEQ ID NO: 44: Primer for amplification of DNA fragment containing ter_rrnB
SEQ ID NO: 45: Nucleotide sequence of DNA fragment containing ter_thrL terminator
SEQ ID NO: 46: Primer for amplification of DNA fragment containing ter_thrL terminator
SEQ ID NO: 47: Primer for amplification of DNA fragment containing ter_thrL terminator
SEQ ID NO: 48: Amino acid sequence of ldhA of *Enterobacter aerogenes* AJ110637
SEQ ID NO: 49: Amino acid sequence of adhE of *Enterobacter aerogenes* AJ110637
SEQ ID NO: 50: Gene sequence of pta of *Enterobacter aerogenes* AJ110637
SEQ ID NO: 51: Amino acid sequence of pta of *Enterobacter aerogenes* AJ110637
SEQ ID NO: 52: Gene sequence of aldC of *Enterobacter aerogenes* AJ110637
SEQ ID NO: 53: Amino acid sequence of aldC of *Enterobacter aerogenes* AJ110637
SEQ ID NO: 54: Gene sequence of pflB of *Enterobacter aerogenes* AJ110637
SEQ ID NO: 55: Amino acid sequence of pflB of *Enterobacter aerogenes* AJ110637
SEQ ID NO: 56: Primer for deletion of ldhA
SEQ ID NO: 57: Primer for deletion of ldhA
SEQ ID NO: 58: Primer for deletion of pta
SEQ ID NO: 59: Primer for deletion of pta
SEQ ID NO: 60: Primer for deletion of aldC
SEQ ID NO: 61: Primer for deletion of aldC
SEQ ID NO: 62: Primer for deletion of pflB
SEQ ID NO: 63: Primer for deletion of pflB
SEQ ID NO: 64: Gene sequence of pckA of *Selenomonas ruminantium* subsp. *lactilytica* TH1
SEQ ID NO: 65: Amino acid sequence of pckA of *Selenomonas ruminantium* subsp. *lactilytica* TH1
SEQ ID NO: 66: Nucleotide sequence of primer intxis_f for construction of RSF-int-xis
SEQ ID NO: 67: Nucleotide sequence of primer intxis_R for construction of RSF-int-xis

INDUSTRIAL APPLICABILITY

According to the method of the present invention, an organic acid can be quickly and highly efficiently produced. When the organic acid is succinic acid, the obtained succinic acid can be used for food additives, pharmaceuticals, cosmetics, and the like. Moreover, succinic acid-containing polymers can also be produced by performing a polymerization reaction using the obtained succinic acid as a raw material.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing an organic acid comprising:
A) allowing a substance to act on an organic raw material in a reaction mixture containing carbonate ions, bicarbonate ions, or carbon dioxide gas, wherein the substance is selected from the group consisting of:
  i) a bacterium belonging to the family Enterobacteriaceae which has an ability to produce an organic acid and has been modified so that the phosphoenolpyruvate carboxykinase activity is enhanced,
  ii) a product obtained by processing the bacterium of i), and
  iii) combinations thereof; and B) collecting the organic acid,
  wherein the bacterium belongs to a genus selected from the group consisting of *Enterobacter*, *Pantoea*, *Erwinia*, *Klebsiella*, and *Raoultella*;
  wherein the phosphoenolpyruvate carboxykinase is encoded by a pckA gene selected from the group consisting of:
  (a) a DNA comprising a nucleotide sequence selected from the group consisting of SEQ ID NO: 6, 8, 10, 12, 14, 16, and 64, and
  (b) a DNA which hybridizes with a nucleotide sequence complementary to a nucleotide sequence selected from the group consisting of SEQ ID NO: 6, 8, 10, 12, 14, 16, and 64 under stringent conditions comprising washing at 60° C. at a salt concentration of 0.1×SSC and 0.1% SDS, and said DNA codes for a protein having phosphoenolpyruvate carboxykinase activity; and wherein the bacterium has been modified by a method selected from the group consisting of:
  i) increasing the copy number of the pckA gene,
  ii) modifying an expression control sequence of the pckA gene, and
  iii) combinations thereof.

2. The method according to claim 1, wherein the the phosphoenolpyruvate carboxykinase is a protein selected from the group consisting of:
  A) a protein comprising an amino acid sequence selected from the group consisting of SEQ ID NO: 7, 9, 11, 13, 15, 17, 65, and 24, and
  B) a protein comprising an amino acid sequence which is at least 95% homologous to an amino acid sequence selected from the group consisting of SEQ ID NO: 7, 9, 11, 13, 15, 17, 65 and 24.

3. The method according to claim 1, wherein the bacterium has been further modified to decrease the activity of an enzyme selected from the group consisting of alcohol dehydrogenase, lactate dehydrogenase, phosphate acetyltransferase, α-acetolactate decarboxylase, pyruvate formate lyase, and combinations thereof.

4. The method according to claim 3, wherein the enzyme is alcohol dehydrogenase.

5. The method according to claim 3, wherein the enzymes are alcohol dehydrogenase and lactate dehydrogenase.

6. The method according to claim 3, wherein the enzymes are alcohol dehydrogenase, lactate dehydrogenase, and phosphate acetyltransferase.

7. The method according to claim 3, wherein the enzymes are alcohol dehydrogenase, lactate dehydrogenase, phosphate acetyltransferase, and α-acetolactate decarboxylase.

8. The method according to claim 3, wherein the enzymes are alcohol dehydrogenase, lactate dehydrogenase, phosphate acetyltransferase, α-acetolactate decarboxylase, and pyruvate formate lyase.

9. The method according to claim 1, wherein the bacterium has been further modified so that pyruvate carboxylase activity is enhanced.

10. The method according to claim 1, wherein the organic acid is succinic acid.

11. A method for producing a succinic acid-containing polymer comprising:
  A) producing succinic acid by the method according to claim 10, and
  B) polymerizing the succinic acid.

* * * * *

SEQUENCE LISTING

```
<160> NUMBER OF SEQ ID NOS: 67

<210> SEQ ID NO 1
<211> LENGTH: 24
<212> TYPE: DNA
<213> ORGANISM: Artificial Sequence
<220> FEATURE:
<223> OTHER INFORMATION: primer for thrLABC

<400> SEQUENCE: 1
tggtcgactg gttacaacaa cgcc                                           24

<210> SEQ ID NO 2
<211> LENGTH: 35
<212> TYPE: DNA
<213> ORGANISM: Artificial Sequence
<220> FEATURE:
<223> OTHER INFORMATION: primer for thrLABC

<400> SEQUENCE: 2
acgtcattcc tccttgtcgc ctatattggt taaag                               35

<210> SEQ ID NO 3
<211> LENGTH: 290
<212> TYPE: DNA
<213> ORGANISM: Escherichia coli

<400> SEQUENCE: 3
```

-continued

```
tggtcgactg gttacaacaa cgcctggggc ttttagagca acgagacacg gcaatgttgc      60
accgtttgct gcatgatatt gaaaaaaata tcaccaaata aaaacgcct tagtaagtat     120 ttttcagctt tcattctga ctgcaacggg caatatgtct ctgtgtggat taaaaaaaga    180
gtgtctgata gcagcttctg aactggttac ctgccgtgag taaattaaaa ttttattgac   240
ttaggtcact aaatacttta accaatatag gcgacaagga ggaatgacgt                290
```

```
<210> SEQ ID NO 4
<211> LENGTH: 40
<212> TYPE: DNA
<213> ORGANISM: Artificial Sequence
<220> FEATURE:
<223> OTHER INFORMATION: primer for A. succinogenes pckA

<400> SEQUENCE: 4
gacaaggagg aatgacgtat gactgactta aacaaactcg                          40
```

```
<210> SEQ ID NO 5
<211> LENGTH: 28
<212> TYPE: DNA
<213> ORGANISM: Artificial Sequence
<220> FEATURE:
<223> OTHER INFORMATION: primer for A. succinogenes pckA

<400> SEQUENCE: 5
acgcgtcgac ctcagcctta tttttcag                                       28
```

```
<210> SEQ ID NO 6
<211> LENGTH: 1713
<212> TYPE: DNA
<213> ORGANISM: Actinobacillus succinogenes
<220> FEATURE:
<221> NAME/KEY: CDS
<222> LOCATION: (19)..(1635)

<400> SEQUENCE: 6
gacaaggagg aatgacgt atg act gac tta aac aaa ctc gtt aaa gaa ctt     51
                    Met Thr Asp Leu Asn Lys Leu Val Lys Glu Leu
                     1               5                  10 aat gac tta ggg ctt acc gat gtt aag gaa att gtg tat aac ccg agt     99
Asn Asp Leu Gly Leu Thr Asp Val Lys Glu Ile Val Tyr Asn Pro Ser
             15                  20                  25 tat gaa caa ctt ttc gag gaa gaa acc aaa ccg ggt ttg gag ggt ttc    147
Tyr Glu Gln Leu Phe Glu Glu Glu Thr Lys Pro Gly Leu Glu Gly Phe
         30                  35                  40 gat aaa ggg acg tta acc acg ctt ggc gcg gtt gcc gtc gat acg ggg    195
Asp Lys Gly Thr Leu Thr Thr Leu Gly Ala Val Ala Val Asp Thr Gly
     45                  50                  55 att ttt acc ggt cgt tca ccg aaa gat aaa tat atc gtt tgc gat gaa    243
Ile Phe Thr Gly Arg Ser Pro Lys Asp Lys Tyr Ile Val Cys Asp Glu
 60                  65                  70                  75 act acg aaa gac acc gtt tgg tgg aac agc gaa gcg gcg aaa aac gat    291
Thr Thr Lys Asp Thr Val Trp Trp Asn Ser Glu Ala Ala Lys Asn Asp
                 80                  85                  90 aac aaa ccg atg acg caa gaa act tgg aaa agt ttg aga gaa tta gtg    339
Asn Lys Pro Met Thr Gln Glu Thr Trp Lys Ser Leu Arg Glu Leu Val
             95                 100                 105 gcg aaa caa ctt tcc ggt aaa cgt tta ttc gtg gta gaa ggt tac tgc    387
Ala Lys Gln Leu Ser Gly Lys Arg Leu Phe Val Val Glu Gly Tyr Cys
        110                 115                 120 ggc gcc agt gaa aaa cac cgt atc ggt gtg cgt atg gtt act gaa gtg    435
Gly Ala Ser Glu Lys His Arg Ile Gly Val Arg Met Val Thr Glu Val
```

```
                        125                 130                 135
gca tgg cag gcg cat ttt gtg aaa aac atg ttt atc cga ccg acc gat     483
Ala Trp Gln Ala His Phe Val Lys Asn Met Phe Ile Arg Pro Thr Asp
140                 145                 150                 155 gaa gag ttg aaa aat ttc aaa gcg gat ttt acc gtg tta aac ggt gct     531
Glu Glu Leu Lys Asn Phe Lys Ala Asp Phe Thr Val Leu Asn Gly Ala
                160                 165                 170 aaa tgt act aat ccg aac tgg aaa gaa caa ggt ttg aac agt gaa aac     579
Lys Cys Thr Asn Pro Asn Trp Lys Glu Gln Gly Leu Asn Ser Glu Asn
                    175                 180                 185 ttt gtc gct ttc aat att acc gaa ggt att cag ctt atc ggc ggt act     627
Phe Val Ala Phe Asn Ile Thr Glu Gly Ile Gln Leu Ile Gly Gly Thr
                190                 195                 200 tgg tac ggc ggt gaa atg aaa aaa ggt atg ttc tca atg atg aac tac     675
Trp Tyr Gly Gly Glu Met Lys Lys Gly Met Phe Ser Met Met Asn Tyr
205                 210                 215 ttc ctg ccg tta aaa ggt gtg gct tcc atg cac tgt tcc gcc aac gta     723
Phe Leu Pro Leu Lys Gly Val Ala Ser Met His Cys Ser Ala Asn Val
220                 225                 230                 235 ggt aaa gac ggt gac gtg gct att ttc ttc ggt tta tcc ggt acg ggt     771
Gly Lys Asp Gly Asp Val Ala Ile Phe Phe Gly Leu Ser Gly Thr Gly
                240                 245                 250 aaa aca acg ctt tcg acc gat cct aaa cgc caa tta atc ggt gat gac     819
Lys Thr Thr Leu Ser Thr Asp Pro Lys Arg Gln Leu Ile Gly Asp Asp
                    255                 260                 265 gaa cac ggt tgg gat gaa tcc ggc gta ttt aac ttt gaa ggc ggt tgt     867
Glu His Gly Trp Asp Glu Ser Gly Val Phe Asn Phe Glu Gly Gly Cys
                270                 275                 280 tac gcg aaa acc att aac tta tct caa gaa aac gaa ccg gat att tac     915
Tyr Ala Lys Thr Ile Asn Leu Ser Gln Glu Asn Glu Pro Asp Ile Tyr
285                 290                 295 ggc gca atc cgt cgt gac gca tta tta gaa aac gtc gtg gtt cgt gca     963
Gly Ala Ile Arg Arg Asp Ala Leu Leu Glu Asn Val Val Val Arg Ala
300                 305                 310                 315 gac ggt tcc gtt gac ttt gac gac ggt tca aaa aca gaa aat acc cgt    1011
Asp Gly Ser Val Asp Phe Asp Asp Gly Ser Lys Thr Glu Asn Thr Arg
                320                 325                 330 gtt tca tat ccg att tac cac atc gac aac atc gtt cgt ccg gta tcg    1059
Val Ser Tyr Pro Ile Tyr His Ile Asp Asn Ile Val Arg Pro Val Ser
                    335                 340                 345 aaa gcc ggt cat gca acc aaa gtg att ttc tta acc gcg gac gca ttc    1107
Lys Ala Gly His Ala Thr Lys Val Ile Phe Leu Thr Ala Asp Ala Phe
                350                 355                 360 ggc gta ttg ccg ccg gtt tca aaa ctg act ccg gaa caa acc gaa tac    1155
Gly Val Leu Pro Pro Val Ser Lys Leu Thr Pro Glu Gln Thr Glu Tyr
365                 370                 375 tac ttc tta tcc ggc ttt act gca aaa tta gcg ggt acg gaa cgc ggc    1203
Tyr Phe Leu Ser Gly Phe Thr Ala Lys Leu Ala Gly Thr Glu Arg Gly
380                 385                 390                 395 gta acc gaa ccg act ccg aca ttc tcg gcc tgt ttc ggt gcg gca ttc    1251
Val Thr Glu Pro Thr Pro Thr Phe Ser Ala Cys Phe Gly Ala Ala Phe
                400                 405                 410 tta agc ctg cat ccg att caa tat gcg gac gtg ttg gtc gaa cgc atg    1299
Leu Ser Leu His Pro Ile Gln Tyr Ala Asp Val Leu Val Glu Arg Met
                    415                 420                 425 aaa gcc tcc ggt gcg gaa gct tat ttg gtg aac acc ggt tgg aac ggc    1347
Lys Ala Ser Gly Ala Glu Ala Tyr Leu Val Asn Thr Gly Trp Asn Gly
                430                 435                 440 acg ggt aaa cgt att tca atc aaa gat acc cgc ggt att atc gat gcg    1395
Thr Gly Lys Arg Ile Ser Ile Lys Asp Thr Arg Gly Ile Ile Asp Ala
```

```
                    445                 450                 455
att ttg gac ggt tca atc gaa aaa gcg gaa atg ggc gaa ttg cca atc      1443
Ile Leu Asp Gly Ser Ile Glu Lys Ala Glu Met Gly Glu Leu Pro Ile
460                 465                 470                 475 ttt aat tta gcg att cct aaa gca tta ccg ggt gtt gat cct gct att      1491
Phe Asn Leu Ala Ile Pro Lys Ala Leu Pro Gly Val Asp Pro Ala Ile
                480                 485                 490 ttg gat ccg cgc gat act tac gca gac aaa gcg caa tgg caa gtt aaa      1539
Leu Asp Pro Arg Asp Thr Tyr Ala Asp Lys Ala Gln Trp Gln Val Lys
            495                 500                 505 gcg gaa gat ttg gca aac cgt ttc gtg aaa aac ttt gtg aaa tat acg      1587
Ala Glu Asp Leu Ala Asn Arg Phe Val Lys Asn Phe Val Lys Tyr Thr
        510                 515                 520 gcg aat ccg gaa gcg gct aaa tta gtt ggc gcc ggt cca aaa gca taa      1635
Ala Asn Pro Glu Ala Ala Lys Leu Val Gly Ala Gly Pro Lys Ala
    525                 530                 535 aactgtaaaa gcatagtatg tgcatgattc ggtaaactac cgaataaaat ctgaaaaata   1695
aggctgaggt cgacgcgt                                                  1713

<210> SEQ ID NO 7
<211> LENGTH: 538
<212> TYPE: PRT
<213> ORGANISM: Actinobacillus succinogenes

<400> SEQUENCE: 7

Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65              70                  75                  80

Val Trp Trp Asn Ser Glu Ala Ala Lys Asn Asp Asn Lys Pro Met Thr
            85                  90                  95

Gln Glu Thr Trp Lys Ser Leu Arg Glu Leu Val Ala Lys Gln Leu Ser
        100                 105                 110

Gly Lys Arg Leu Phe Val Val Glu Gly Tyr Cys Gly Ala Ser Glu Lys
    115                 120                 125

His Arg Ile Gly Val Arg Met Val Thr Glu Val Ala Trp Gln Ala His
130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
            165                 170                 175

Asn Trp Lys Glu Gln Gly Leu Asn Ser Glu Asn Phe Val Ala Phe Asn
        180                 185                 190

Ile Thr Glu Gly Ile Gln Leu Ile Gly Gly Thr Trp Tyr Gly Gly Glu
    195                 200                 205

Met Lys Lys Gly Met Phe Ser Met Met Asn Tyr Phe Leu Pro Leu Lys
210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
```

-continued

```
                245                 250                 255
Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
        275                 280                 285

Asn Leu Ser Gln Glu Asn Glu Pro Asp Ile Tyr Gly Ala Ile Arg Arg
    290                 295                 300

Asp Ala Leu Leu Glu Asn Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
            340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Glu Tyr Tyr Phe Leu Ser Gly
    370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
            500                 505                 510

Asn Arg Phe Val Lys Asn Phe Val Lys Tyr Thr Ala Asn Pro Glu Ala
        515                 520                 525

Ala Lys Leu Val Gly Ala Gly Pro Lys Ala
    530                 535

<210> SEQ ID NO 8
<211> LENGTH: 1617
<212> TYPE: DNA
<213> ORGANISM: Haemophilus influenzae
<220> FEATURE:
<221> NAME/KEY: CDS
<222> LOCATION: (1)..(1617)

<400> SEQUENCE: 8 atg aca gac tta aat aaa gtg gta aaa gaa ctt gaa gct ctt ggc att       48
Met Thr Asp Leu Asn Lys Val Val Lys Glu Leu Glu Ala Leu Gly Ile
1               5                   10                  15 tat gac gta aaa gaa gtt gtt tac aat cca agc tac gag caa ttg ttc       96
Tyr Asp Val Lys Glu Val Val Tyr Asn Pro Ser Tyr Glu Gln Leu Phe
            20                  25                  30 gaa gaa gaa act aaa cca ggc tta gaa ggc ttt gaa aaa ggt act tta      144
Glu Glu Glu Thr Lys Pro Gly Leu Glu Gly Phe Glu Lys Gly Thr Leu
        35                  40                  45 act acg act ggt gca gtg gca gta gat aca ggt atc ttc aca ggt cgt      192
Thr Thr Thr Gly Ala Val Ala Val Asp Thr Gly Ile Phe Thr Gly Arg
```

-continued

```
                Thr Thr Thr Gly Ala Val Ala Val Asp Thr Gly Ile Phe Thr Gly Arg
                    50              55                  60 tct cca aaa gat aaa tat atc gtg tta gat gaa aaa acc aaa gat act        240
Ser Pro Lys Asp Lys Tyr Ile Val Leu Asp Glu Lys Thr Lys Asp Thr
65              70                  75                  80 gtt tgg tgg aca tct gaa aca gca aaa aac gac aac aag cca atg aac        288
Val Trp Trp Thr Ser Glu Thr Ala Lys Asn Asp Asn Lys Pro Met Asn
                85                  90                  95 caa gct aca tgg caa agc tta aaa gac ttg gta acc aac caa ctt tct        336
Gln Ala Thr Trp Gln Ser Leu Lys Asp Leu Val Thr Asn Gln Leu Ser
            100                 105                 110 cgt aaa cgc tta ttt gta gtt gat ggt ttc tgt ggt gcg agc gaa cac        384
Arg Lys Arg Leu Phe Val Val Asp Gly Phe Cys Gly Ala Ser Glu His
        115                 120                 125 gac cgt att gca gta cgt atc gtc act gaa gta gcg tgg caa gca cat        432
Asp Arg Ile Ala Val Arg Ile Val Thr Glu Val Ala Trp Gln Ala His
130                 135                 140 ttt gta aaa aat atg ttt att cgc cca act gaa gaa caa ctc aaa aat        480
Phe Val Lys Asn Met Phe Ile Arg Pro Thr Glu Glu Gln Leu Lys Asn
145                 150                 155                 160 ttt gaa cca gat ttc gtt gta atg aac ggt tct aaa gta acc aat cca        528
Phe Glu Pro Asp Phe Val Val Met Asn Gly Ser Lys Val Thr Asn Pro
                165                 170                 175 aac tgg aaa gaa caa ggt tta aat tca gaa aac ttt gtt gct ttc aac        576
Asn Trp Lys Glu Gln Gly Leu Asn Ser Glu Asn Phe Val Ala Phe Asn
            180                 185                 190 ttg act gaa cgc att caa tta atc ggc ggt act tgg tac ggc ggc gaa        624
Leu Thr Glu Arg Ile Gln Leu Ile Gly Gly Thr Trp Tyr Gly Gly Glu
        195                 200                 205 atg aaa aaa ggt atg ttc tca atg atg aac tac ttc cta cct ctc aaa        672
Met Lys Lys Gly Met Phe Ser Met Met Asn Tyr Phe Leu Pro Leu Lys
210                 215                 220 ggt gtt ggt gca atg cac tgc tca gct aac gtt ggt aaa gat ggt gat        720
Gly Val Gly Ala Met His Cys Ser Ala Asn Val Gly Lys Asp Gly Asp
225                 230                 235                 240 gta gca atc ttc ttc ggc tta tct ggc aca ggt aaa aca acc ctt tca        768
Val Ala Ile Phe Phe Gly Leu Ser Gly Thr Gly Lys Thr Thr Leu Ser
                245                 250                 255 acg gat cca aaa cgt gaa tta atc ggt gac gat gaa cac ggt tgg gat        816
Thr Asp Pro Lys Arg Glu Leu Ile Gly Asp Asp Glu His Gly Trp Asp
            260                 265                 270 gat gtt ggt atc ttt aac ttt gaa ggt ggt tgt tat gcg aaa acc att        864
Asp Val Gly Ile Phe Asn Phe Glu Gly Gly Cys Tyr Ala Lys Thr Ile
        275                 280                 285 cat ctt tca gaa gaa aat gaa cca gat att tac cac gct atc cgt cgc        912
His Leu Ser Glu Glu Asn Glu Pro Asp Ile Tyr His Ala Ile Arg Arg
290                 295                 300 gac gca tta tta gaa aac gtg gtt gtt cgt tca gat ggt tct gtt gat        960
Asp Ala Leu Leu Glu Asn Val Val Val Arg Ser Asp Gly Ser Val Asp
305                 310                 315                 320 ttc gat gat ggt tca aaa aca gaa aat act cgc gtg tct tac cca att       1008
Phe Asp Asp Gly Ser Lys Thr Glu Asn Thr Arg Val Ser Tyr Pro Ile
                325                 330                 335 tat cac atc gat aac att gta aaa cca gtt tct cgt gca ggt cac gca       1056
Tyr His Ile Asp Asn Ile Val Lys Pro Val Ser Arg Ala Gly His Ala
            340                 345                 350 act aaa gtg att ttc tta act gca gat gcg ttt ggt gta tta cct cca       1104
Thr Lys Val Ile Phe Leu Thr Ala Asp Ala Phe Gly Val Leu Pro Pro
        355                 360                 365 gta tct aaa ttg aca cca gaa caa act aaa tac tac ttc tta tct ggt       1152
```

```
                Val Ser Lys Leu Thr Pro Glu Gln Thr Lys Tyr Tyr Phe Leu Ser Gly
                    370                 375                 380 ttc aca gcg aaa tta gca ggg act gaa cgt ggt att act gaa cca acg          1200
Phe Thr Ala Lys Leu Ala Gly Thr Glu Arg Gly Ile Thr Glu Pro Thr
385                 390                 395                 400 cca act ttc tca gca tgt ttc ggt gca gca ttt tta acg ctt cat cca          1248
Pro Thr Phe Ser Ala Cys Phe Gly Ala Ala Phe Leu Thr Leu His Pro
                405                 410                 415 act caa tat gca gaa gtg tta gta aaa cgt atg caa gca ggt gct              1296
Thr Gln Tyr Ala Glu Val Leu Val Lys Arg Met Gln Ala Gly Ala
            420                 425                 430 gaa gct tac tta gtg aat act ggt tgg aat ggc aca ggc aaa cgt atc          1344
Glu Ala Tyr Leu Val Asn Thr Gly Trp Asn Gly Thr Gly Lys Arg Ile
                435                 440                 445 tca atc aaa gat act cgc gga atc att gat gca atc tta gat ggc tca          1392
Ser Ile Lys Asp Thr Arg Gly Ile Ile Asp Ala Ile Leu Asp Gly Ser
    450                 455                 460 att gaa aaa gct gaa atg ggc gaa ttg cca atc ttc aac tta gca att          1440
Ile Glu Lys Ala Glu Met Gly Glu Leu Pro Ile Phe Asn Leu Ala Ile
465                 470                 475                 480 cct aaa gca tta cca ggt gta gat tct gca atc tta gat cct cgc gat          1488
Pro Lys Ala Leu Pro Gly Val Asp Ser Ala Ile Leu Asp Pro Arg Asp
                485                 490                 495 act tac gca gat aaa gca caa tgg caa tca aaa gct gaa gac tta gca          1536
Thr Tyr Ala Asp Lys Ala Gln Trp Gln Ser Lys Ala Glu Asp Leu Ala
                500                 505                 510 ggt cgt ttt gtg aaa aac ttt gtt aaa tat gca act aac gaa gaa ggc          1584
Gly Arg Phe Val Lys Asn Phe Val Lys Tyr Ala Thr Asn Glu Glu Gly
            515                 520                 525 aaa gct tta att gca gct ggt cct aaa gct taa                              1617
Lys Ala Leu Ile Ala Ala Gly Pro Lys Ala
            530                 535
```

<210> SEQ ID NO 9
<211> LENGTH: 538
<212> TYPE: PRT
<213> ORGANISM: Haemophilus influenzae

<400> SEQUENCE: 9

```
Met Thr Asp Leu Asn Lys Val Val Lys Glu Leu Glu Ala Leu Gly Ile
1               5                   10                  15

Tyr Asp Val Lys Glu Val Val Tyr Asn Pro Ser Tyr Glu Gln Leu Phe
            20                  25                  30

Glu Glu Glu Thr Lys Pro Gly Leu Glu Gly Phe Glu Lys Gly Thr Leu
        35                  40                  45

Thr Thr Thr Gly Ala Val Ala Val Asp Thr Gly Ile Phe Thr Gly Arg
    50                  55                  60

Ser Pro Lys Asp Lys Tyr Ile Val Leu Asp Glu Lys Thr Lys Asp Thr
65                  70                  75                  80

Val Trp Trp Thr Ser Glu Thr Ala Lys Asn Asp Asn Lys Pro Met Asn
                85                  90                  95

Gln Ala Thr Trp Gln Ser Leu Lys Asp Leu Val Thr Asn Gln Leu Ser
            100                 105                 110

Arg Lys Arg Leu Phe Val Val Asp Gly Phe Cys Gly Ala Ser Glu His
        115                 120                 125

Asp Arg Ile Ala Val Arg Ile Val Thr Glu Val Ala Trp Gln Ala His
    130                 135                 140

Phe Val Lys Asn Met Phe Ile Arg Pro Thr Glu Glu Gln Leu Lys Asn
145                 150                 155                 160
```

Phe Glu Pro Asp Phe Val Val Met Asn Gly Ser Lys Val Thr Asn Pro
                165                 170                 175

Asn Trp Lys Glu Gln Gly Leu Asn Ser Glu Asn Phe Val Ala Phe Asn
            180                 185                 190

Leu Thr Glu Arg Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
    210                 215                 220

Gly Val Gly Ala Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Glu Leu Ile Gly Asp Asp Glu His Gly Trp Asp
            260                 265                 270

Asp Val Gly Ile Phe Asn Phe Glu Gly Gly Cys Tyr Ala Lys Thr Ile
        275                 280                 285

His Leu Ser Glu Glu Asn Glu Pro Asp Ile Tyr His Ala Ile Arg Arg
    290                 295                 300

Asp Ala Leu Leu Glu Asn Val Val Val Arg Ser Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Lys Pro Val Ser Arg Ala Gly His Ala
            340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Lys Tyr Tyr Phe Leu Ser Gly
    370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Ala Ala Phe Leu Thr Leu His Pro
                405                 410                 415

Thr Gln Tyr Ala Glu Val Leu Val Lys Arg Met Gln Ala Ala Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Ser Ala Ile Leu Asp Pro Arg Asp
                485                 490                 495

Thr Tyr Ala Asp Lys Ala Gln Trp Gln Ser Lys Ala Glu Asp Leu Ala
            500                 505                 510

Gly Arg Phe Val Lys Asn Phe Val Lys Tyr Ala Thr Asn Glu Glu Gly
        515                 520                 525

Lys Ala Leu Ile Ala Ala Gly Pro Lys Ala
    530                 535

<210> SEQ ID NO 10
<211> LENGTH: 1617
<212> TYPE: DNA
<213> ORGANISM: Pasteurella multocida
<220> FEATURE:
<221> NAME/KEY: CDS

<222> LOCATION: (1)..(1617)

<400> SEQUENCE: 10

| | | | | | | | | | | | | | | | | |
|---|---|---|---|---|---|---|---|---|---|---|---|---|---|---|---|---|
| atg | act | gac | tta | aat | aaa | gta | atc | aat | gaa | ctt | ggt | gca | ctt | ggt | att | 48 |
| Met | Thr | Asp | Leu | Asn | Lys | Val | Ile | Asn | Glu | Leu | Gly | Ala | Leu | Gly | Ile | |
| 1 | | | | 5 | | | | | 10 | | | | | 15 | | |

| cat | gat | gta | aaa | gaa | atc | gtt | tat | aac | cca | agt | tat | gag | caa | ttg | ttc | 96 |
|---|---|---|---|---|---|---|---|---|---|---|---|---|---|---|---|---|
| His | Asp | Val | Lys | Glu | Ile | Val | Tyr | Asn | Pro | Ser | Tyr | Glu | Gln | Leu | Phe | |
| | | | 20 | | | | | 25 | | | | | 30 | | | |

| gaa | gag | gaa | acc | aaa | cca | ggt | tta | gaa | ggt | tac | gaa | aaa | ggt | atc | gtg | 144 |
|---|---|---|---|---|---|---|---|---|---|---|---|---|---|---|---|---|
| Glu | Glu | Glu | Thr | Lys | Pro | Gly | Leu | Glu | Gly | Tyr | Glu | Lys | Gly | Ile | Val | |
| | | 35 | | | | | 40 | | | | | 45 | | | | |

| aca | caa | tca | ggc | gcg | gtg | gcg | gtt | gat | acc | ggt | atc | ttt | aca | ggt | cgt | 192 |
|---|---|---|---|---|---|---|---|---|---|---|---|---|---|---|---|---|
| Thr | Gln | Ser | Gly | Ala | Val | Ala | Val | Asp | Thr | Gly | Ile | Phe | Thr | Gly | Arg | |
| | 50 | | | | | 55 | | | | | 60 | | | | | |

| tcg | cca | aaa | gat | aaa | tac | att | gtg | ctt | gat | gac | aaa | acc | aaa | gac | act | 240 |
|---|---|---|---|---|---|---|---|---|---|---|---|---|---|---|---|---|
| Ser | Pro | Lys | Asp | Lys | Tyr | Ile | Val | Leu | Asp | Asp | Lys | Thr | Lys | Asp | Thr | |
| 65 | | | | | 70 | | | | | 75 | | | | | 80 | |

| gtt | tgg | tgg | aca | agc | gat | gcg | gcg | aaa | aac | gat | aac | aaa | cca | atg | aca | 288 |
|---|---|---|---|---|---|---|---|---|---|---|---|---|---|---|---|---|
| Val | Trp | Trp | Thr | Ser | Asp | Ala | Ala | Lys | Asn | Asp | Asn | Lys | Pro | Met | Thr | |
| | | | | 85 | | | | | 90 | | | | | 95 | | |

| caa | gat | acg | tgg | aaa | agc | tta | aaa | ggc | tta | gtg | aca | gaa | caa | ctt | tct | 336 |
|---|---|---|---|---|---|---|---|---|---|---|---|---|---|---|---|---|
| Gln | Asp | Thr | Trp | Lys | Ser | Leu | Lys | Gly | Leu | Val | Thr | Glu | Gln | Leu | Ser | |
| | | | 100 | | | | | 105 | | | | | 110 | | | |

| ggc | aaa | cgt | tta | ttt | gtg | atc | gac | gca | ttc | tgt | ggt | gca | aac | gct | gac | 384 |
|---|---|---|---|---|---|---|---|---|---|---|---|---|---|---|---|---|
| Gly | Lys | Arg | Leu | Phe | Val | Ile | Asp | Ala | Phe | Cys | Gly | Ala | Asn | Ala | Asp | |
| | | 115 | | | | | 120 | | | | | 125 | | | | |

| acc | cgt | tta | tca | gtg | cgt | atc | gtg | aca | gaa | gta | gca | tgg | caa | gca | cac | 432 |
|---|---|---|---|---|---|---|---|---|---|---|---|---|---|---|---|---|
| Thr | Arg | Leu | Ser | Val | Arg | Ile | Val | Thr | Glu | Val | Ala | Trp | Gln | Ala | His | |
| | 130 | | | | | 135 | | | | | 140 | | | | | |

| ttt | gtg | aaa | aac | atg | ttc | att | cgt | cca | aca | gaa | gca | gaa | tta | gtt | ggc | 480 |
|---|---|---|---|---|---|---|---|---|---|---|---|---|---|---|---|---|
| Phe | Val | Lys | Asn | Met | Phe | Ile | Arg | Pro | Thr | Glu | Ala | Glu | Leu | Val | Gly | |
| 145 | | | | | 150 | | | | | 155 | | | | | 160 | |

| ttc | aaa | cca | gat | ttc | gta | gta | atg | aac | ggt | tct | aaa | gta | acc | aac | ccg | 528 |
|---|---|---|---|---|---|---|---|---|---|---|---|---|---|---|---|---|
| Phe | Lys | Pro | Asp | Phe | Val | Val | Met | Asn | Gly | Ser | Lys | Val | Thr | Asn | Pro | |
| | | | | 165 | | | | | 170 | | | | | 175 | | |

| aac | tgg | aaa | gaa | caa | ggt | cta | aat | tct | gaa | aac | ttt | gtg | gca | ttt | aac | 576 |
|---|---|---|---|---|---|---|---|---|---|---|---|---|---|---|---|---|
| Asn | Trp | Lys | Glu | Gln | Gly | Leu | Asn | Ser | Glu | Asn | Phe | Val | Ala | Phe | Asn | |
| | | | 180 | | | | | 185 | | | | | 190 | | | |

| tta | act | gaa | ggc | gtg | caa | tta | atc | ggt | ggt | act | tgg | tac | ggc | ggt | gaa | 624 |
|---|---|---|---|---|---|---|---|---|---|---|---|---|---|---|---|---|
| Leu | Thr | Glu | Gly | Val | Gln | Leu | Ile | Gly | Gly | Thr | Trp | Tyr | Gly | Gly | Glu | |
| | | 195 | | | | | 200 | | | | | 205 | | | | |

| atg | aaa | aaa | ggt | atg | ttc | tca | atg | atg | aac | tac | ttc | tta | cca | tta | aaa | 672 |
|---|---|---|---|---|---|---|---|---|---|---|---|---|---|---|---|---|
| Met | Lys | Lys | Gly | Met | Phe | Ser | Met | Met | Asn | Tyr | Phe | Leu | Pro | Leu | Lys | |
| | 210 | | | | | 215 | | | | | 220 | | | | | |

| ggc | atc | gca | tct | atg | cac | tgt | tca | gcc | aac | gtg | ggt | gaa | aaa | ggc | gac | 720 |
|---|---|---|---|---|---|---|---|---|---|---|---|---|---|---|---|---|
| Gly | Ile | Ala | Ser | Met | His | Cys | Ser | Ala | Asn | Val | Gly | Glu | Lys | Gly | Asp | |
| 225 | | | | | 230 | | | | | 235 | | | | | 240 | |

| gtt | gct | gtg | ttc | ttc | ggt | tta | tca | ggt | aca | ggt | aaa | acc | acc | ctt | tca | 768 |
|---|---|---|---|---|---|---|---|---|---|---|---|---|---|---|---|---|
| Val | Ala | Val | Phe | Phe | Gly | Leu | Ser | Gly | Thr | Gly | Lys | Thr | Thr | Leu | Ser | |
| | | | | 245 | | | | | 250 | | | | | 255 | | |

| aca | gat | cca | aaa | cgt | caa | tta | atc | ggt | gac | gat | gag | cac | ggt | tgg | gat | 816 |
|---|---|---|---|---|---|---|---|---|---|---|---|---|---|---|---|---|
| Thr | Asp | Pro | Lys | Arg | Gln | Leu | Ile | Gly | Asp | Asp | Glu | His | Gly | Trp | Asp | |
| | | | 260 | | | | | 265 | | | | | 270 | | | |

| gat | gat | ggc | gta | ttc | aac | tac | gaa | ggt | ggt | tgc | tat | gcg | aaa | acg | atc | 864 |
|---|---|---|---|---|---|---|---|---|---|---|---|---|---|---|---|---|
| Asp | Asp | Gly | Val | Phe | Asn | Tyr | Glu | Gly | Gly | Cys | Tyr | Ala | Lys | Thr | Ile | |
| | | 275 | | | | | 280 | | | | | 285 | | | | |

| aaa | ctg | tct | cca | gaa | aac | gaa | cca | gat | atc | tat | aaa | gcc | atc | aaa | cgt | 912 |
|---|---|---|---|---|---|---|---|---|---|---|---|---|---|---|---|---|
| Lys | Leu | Ser | Pro | Glu | Asn | Glu | Pro | Asp | Ile | Tyr | Lys | Ala | Ile | Lys | Arg | |
| | 290 | | | | | 295 | | | | | 300 | | | | | |

```
gat gcc tta tta gaa aac gtt gta gta cgt gca gat ggt tca gtg gat    960
Asp Ala Leu Leu Glu Asn Val Val Val Arg Ala Asp Gly Ser Val Asp
305                 310                 315                 320 tac gat gat ggt tca aaa aca gaa aac acc cgt gtt tct tac cca att   1008
Tyr Asp Asp Gly Ser Lys Thr Glu Asn Thr Arg Val Ser Tyr Pro Ile
                325                 330                 335 tac cac atc gac aac atc gta aca ccg gta tca aaa gca ggt cat gcg   1056
Tyr His Ile Asp Asn Ile Val Thr Pro Val Ser Lys Ala Gly His Ala
            340                 345                 350 aaa aaa gtg atc ttc tta act gcg gac gca ttc ggt gtg tta cca cca   1104
Lys Lys Val Ile Phe Leu Thr Ala Asp Ala Phe Gly Val Leu Pro Pro
        355                 360                 365 gta tct aaa tta acg cca gaa caa act aaa tac tac ttc tta tct ggt   1152
Val Ser Lys Leu Thr Pro Glu Gln Thr Lys Tyr Tyr Phe Leu Ser Gly
    370                 375                 380 ttc acc gcg aaa tta gcc ggt act gag cgt ggt atc aca gaa cca aca   1200
Phe Thr Ala Lys Leu Ala Gly Thr Glu Arg Gly Ile Thr Glu Pro Thr
385                 390                 395                 400 cca acg ttc tct gca tgt ttc ggt gca gcg ttc tta tca ctt cac cca   1248
Pro Thr Phe Ser Ala Cys Phe Gly Ala Ala Phe Leu Ser Leu His Pro
                405                 410                 415 aca caa tat gcg gaa gtg tta gtg aaa cgt atg gaa gca gcg ggt gcg   1296
Thr Gln Tyr Ala Glu Val Leu Val Lys Arg Met Glu Ala Ala Gly Ala
            420                 425                 430 gaa gct tac tta gtg aac aca ggt tgg aac ggt aca ggt aaa cgt atc   1344
Glu Ala Tyr Leu Val Asn Thr Gly Trp Asn Gly Thr Gly Lys Arg Ile
        435                 440                 445 tca atc aaa gat acg cgc ggt atc atc gat gca atc tta gac ggt tca   1392
Ser Ile Lys Asp Thr Arg Gly Ile Ile Asp Ala Ile Leu Asp Gly Ser
    450                 455                 460 atc gaa aaa gca gaa atg ggc aaa tta cca atc ttt gat tta gcg atc   1440
Ile Glu Lys Ala Glu Met Gly Lys Leu Pro Ile Phe Asp Leu Ala Ile
465                 470                 475                 480 cca act gca tta cca ggt gtt gac cct gca atc tta gat cca cgt gat   1488
Pro Thr Ala Leu Pro Gly Val Asp Pro Ala Ile Leu Asp Pro Arg Asp
                485                 490                 495 act tat gca gac aaa gca caa tgg caa gcg aaa gca gaa gac tta gct   1536
Thr Tyr Ala Asp Lys Ala Gln Trp Gln Ala Lys Ala Glu Asp Leu Ala
            500                 505                 510 ggt cgt ttc gtg aaa aac ttc gaa aaa tac acc act aac gat gaa ggt   1584
Gly Arg Phe Val Lys Asn Phe Glu Lys Tyr Thr Thr Asn Asp Glu Gly
        515                 520                 525 aaa gca tta gtg gca gca ggt cca aaa gcg taa                       1617
Lys Ala Leu Val Ala Ala Gly Pro Lys Ala
    530                 535

<210> SEQ ID NO 11
<211> LENGTH: 538
<212> TYPE: PRT
<213> ORGANISM: Pasteurella multocida

<400> SEQUENCE: 11

Met Thr Asp Leu Asn Lys Val Ile Asn Glu Leu Gly Ala Leu Gly Ile
1               5                   10                  15

His Asp Val Lys Glu Ile Val Tyr Asn Pro Ser Tyr Glu Gln Leu Phe
            20                  25                  30

Glu Glu Glu Thr Lys Pro Gly Leu Gly Tyr Glu Lys Gly Ile Val
        35                  40                  45

Thr Gln Ser Gly Ala Val Ala Val Asp Thr Gly Ile Phe Thr Gly Arg
    50                  55                  60
```

```
Ser Pro Lys Asp Lys Tyr Ile Val Leu Asp Asp Lys Thr Lys Asp Thr
 65                  70                  75                  80

Val Trp Trp Thr Ser Asp Ala Ala Lys Asn Asp Asn Lys Pro Met Thr
                 85                  90                  95

Gln Asp Thr Trp Lys Ser Leu Lys Gly Leu Val Thr Glu Gln Leu Ser
            100                 105                 110

Gly Lys Arg Leu Phe Val Ile Asp Ala Phe Cys Gly Ala Asn Ala Asp
        115                 120                 125

Thr Arg Leu Ser Val Arg Ile Val Thr Glu Val Ala Trp Gln Ala His
130                 135                 140

Phe Val Lys Asn Met Phe Ile Arg Pro Thr Glu Ala Glu Leu Val Gly
145                 150                 155                 160

Phe Lys Pro Asp Phe Val Met Asn Gly Ser Lys Val Thr Asn Pro
                165                 170                 175

Asn Trp Lys Glu Gln Gly Leu Asn Ser Glu Asn Phe Val Ala Phe Asn
            180                 185                 190

Leu Thr Glu Gly Val Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
210                 215                 220

Gly Ile Ala Ser Met His Cys Ser Ala Asn Val Gly Glu Lys Gly Asp
225                 230                 235                 240

Val Ala Val Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Asp Asp Gly Val Phe Asn Tyr Glu Gly Gly Cys Tyr Ala Lys Thr Ile
        275                 280                 285

Lys Leu Ser Pro Glu Asn Glu Pro Asp Ile Tyr Lys Ala Ile Lys Arg
290                 295                 300

Asp Ala Leu Leu Glu Asn Val Val Arg Ala Asp Gly Ser Val Asp
305                 310                 315                 320

Tyr Asp Asp Gly Ser Lys Thr Glu Asn Thr Arg Val Ser Tyr Pro Ile
                325                 330                 335

Tyr His Ile Asp Asn Ile Val Thr Pro Val Ser Lys Ala Gly His Ala
            340                 345                 350

Lys Lys Val Ile Phe Leu Thr Ala Asp Ala Phe Gly Val Leu Pro Pro
        355                 360                 365

Val Ser Lys Leu Thr Pro Glu Gln Thr Lys Tyr Tyr Phe Leu Ser Gly
370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Ala Ala Phe Leu Ser Leu His Pro
                405                 410                 415

Thr Gln Tyr Ala Glu Val Leu Val Lys Arg Met Glu Ala Ala Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
450                 455                 460

Ile Glu Lys Ala Glu Met Gly Lys Leu Pro Ile Phe Asp Leu Ala Ile
465                 470                 475                 480

Pro Thr Ala Leu Pro Gly Val Asp Pro Ala Ile Leu Asp Pro Arg Asp
                485                 490                 495
```

```
Thr Tyr Ala Asp Lys Ala Gln Trp Gln Ala Lys Ala Glu Asp Leu Ala
            500                 505                 510
Gly Arg Phe Val Lys Asn Phe Glu Lys Tyr Thr Thr Asn Asp Glu Gly
        515                 520                 525
Lys Ala Leu Val Ala Ala Gly Pro Lys Ala
    530                 535

<210> SEQ ID NO 12
<211> LENGTH: 1617
<212> TYPE: DNA
<213> ORGANISM: Mannheimia succiniciproducens
<220> FEATURE:
<221> NAME/KEY: CDS
<222> LOCATION: (1)..(1617)

<400> SEQUENCE: 12 atg aca gat ctt aat caa tta act caa gaa ctt ggt gct tta ggt att      48
Met Thr Asp Leu Asn Gln Leu Thr Gln Glu Leu Gly Ala Leu Gly Ile
1               5                   10                  15 cat gat gta caa gaa gtt gtg tat aac ccg agc tat gaa ctt ctt ttt      96
His Asp Val Gln Glu Val Val Tyr Asn Pro Ser Tyr Glu Leu Leu Phe
            20                  25                  30 gcg gaa gaa acc aaa cca ggt tta gaa ggt tat gaa aaa ggt act gtg     144
Ala Glu Glu Thr Lys Pro Gly Leu Glu Gly Tyr Glu Lys Gly Thr Val
        35                  40                  45 act aat caa gga gcg gtt gct gta aat acc ggt att ttc acc ggt cgt     192
Thr Asn Gln Gly Ala Val Ala Val Asn Thr Gly Ile Phe Thr Gly Arg
    50                  55                  60 tct ccg aaa gat aaa tat atc gtt tta gac gac aaa act aaa gat acc     240
Ser Pro Lys Asp Lys Tyr Ile Val Leu Asp Asp Lys Thr Lys Asp Thr
65                  70                  75                  80 gta tgg tgg acc agc gaa aaa gtt aaa aac gat aac aaa cca atg agc     288
Val Trp Trp Thr Ser Glu Lys Val Lys Asn Asp Asn Lys Pro Met Ser
                85                  90                  95 caa gat acc tgg aac agt ttg aaa ggt tta gtt gcc gat caa ctt tcc     336
Gln Asp Thr Trp Asn Ser Leu Lys Gly Leu Val Ala Asp Gln Leu Ser
            100                 105                 110 ggt aaa cgt tta ttt gtt gtt gac gca ttc tgc ggc gcg aat aaa gat     384
Gly Lys Arg Leu Phe Val Val Asp Ala Phe Cys Gly Ala Asn Lys Asp
        115                 120                 125 acg cgt tta gct gtt cgt gtg gtt act gaa gtt gca tgg cag gcg cat     432
Thr Arg Leu Ala Val Arg Val Val Thr Glu Val Ala Trp Gln Ala His
    130                 135                 140 ttt gta aca aat atg ttt atc cgc cct tca gcg gaa gaa tta aaa ggt     480
Phe Val Thr Asn Met Phe Ile Arg Pro Ser Ala Glu Glu Leu Lys Gly
145                 150                 155                 160 ttc aaa cct gat ttc gtg gta atg aac ggt gca aaa tgt aca aat cct     528
Phe Lys Pro Asp Phe Val Val Met Asn Gly Ala Lys Cys Thr Asn Pro
                165                 170                 175 aac tgg aaa gaa caa ggg tta aat tcc gaa aac ttc gtt gcg ttc aac     576
Asn Trp Lys Glu Gln Gly Leu Asn Ser Glu Asn Phe Val Ala Phe Asn
            180                 185                 190 att aca gaa ggc gtt caa tta atc ggc ggt act tgg tac ggt ggt gaa     624
Ile Thr Glu Gly Val Gln Leu Ile Gly Gly Thr Trp Tyr Gly Gly Glu
        195                 200                 205 atg aaa aaa ggt atg ttc tca atg atg aac tac ttc tta ccg ctt cgt     672
Met Lys Lys Gly Met Phe Ser Met Met Asn Tyr Phe Leu Pro Leu Arg
    210                 215                 220 ggt att gca tca atg cac tgt tcc gca aac gtt ggt aaa gac ggc gat     720
Gly Ile Ala Ser Met His Cys Ser Ala Asn Val Gly Lys Asp Gly Asp
225                 230                 235                 240
```

```
acc gca att ttc ttc ggt ttg tca ggc aca ggt aaa acg aca tta tca       768
Thr Ala Ile Phe Phe Gly Leu Ser Gly Thr Gly Lys Thr Thr Leu Ser
            245                 250                 255 aca gat cct aaa cgt caa cta atc ggt gat gac gaa cac ggt tgg gac       816
Thr Asp Pro Lys Arg Gln Leu Ile Gly Asp Asp Glu His Gly Trp Asp
        260                 265                 270 gat gaa ggc gta ttt aac ttc gaa ggt ggt tgc tac gcg aaa acc att       864
Asp Glu Gly Val Phe Asn Phe Glu Gly Gly Cys Tyr Ala Lys Thr Ile
    275                 280                 285 aac tta tcc gct gaa aac gag ccg gat atc tat ggc gct atc aaa cgt       912
Asn Leu Ser Ala Glu Asn Glu Pro Asp Ile Tyr Gly Ala Ile Lys Arg
290                 295                 300 gac gca tta ttg gaa aac gtg gtt gtt tta gat aac ggt gac gtt gac       960
Asp Ala Leu Leu Glu Asn Val Val Val Leu Asp Asn Gly Asp Val Asp
305                 310                 315                 320 tat gca gac ggt tcc aaa aca gaa aat aca cgt gtt tct tat ccg att      1008
Tyr Ala Asp Gly Ser Lys Thr Glu Asn Thr Arg Val Ser Tyr Pro Ile
                325                 330                 335 tat cac att caa aat atc gtt aaa cct gtt tct aaa gct ggt ccg gca      1056
Tyr His Ile Gln Asn Ile Val Lys Pro Val Ser Lys Ala Gly Pro Ala
            340                 345                 350 act aaa gtt atc ttc ttg tct gcc gat gca ttc ggt gta tta ccg ccg      1104
Thr Lys Val Ile Phe Leu Ser Ala Asp Ala Phe Gly Val Leu Pro Pro
        355                 360                 365 gtg tct aaa tta act ccg gaa caa acc aaa tac tat ttc tta tcc ggt      1152
Val Ser Lys Leu Thr Pro Glu Gln Thr Lys Tyr Tyr Phe Leu Ser Gly
    370                 375                 380 ttc act gcg aaa tta gcg ggt acg gaa cgc ggt att aca gag cct aca      1200
Phe Thr Ala Lys Leu Ala Gly Thr Glu Arg Gly Ile Thr Glu Pro Thr
385                 390                 395                 400 cca aca ttc tct gca tgt ttt ggt gcg gct ttt tta agc ttg cat ccg      1248
Pro Thr Phe Ser Ala Cys Phe Gly Ala Ala Phe Leu Ser Leu His Pro
                405                 410                 415 aca caa tat gcc gaa gtg tta gta aaa cgt atg caa gaa tca ggt gcg      1296
Thr Gln Tyr Ala Glu Val Leu Val Lys Arg Met Gln Glu Ser Gly Ala
            420                 425                 430 gaa gcg tat ctt gtt aat aca ggt tgg aac ggt acc ggc aaa cgt atc      1344
Glu Ala Tyr Leu Val Asn Thr Gly Trp Asn Gly Thr Gly Lys Arg Ile
        435                 440                 445 tca att aaa gat acc cgt ggt att att gat gca att tta gac ggc tca      1392
Ser Ile Lys Asp Thr Arg Gly Ile Ile Asp Ala Ile Leu Asp Gly Ser
    450                 455                 460 att gat aaa gcg gaa atg ggc tca tta cca atc ttc gat ttc tca att      1440
Ile Asp Lys Ala Glu Met Gly Ser Leu Pro Ile Phe Asp Phe Ser Ile
465                 470                 475                 480 cct aaa gca tta cct ggt gtt aac cct gca atc tta gat ccg cgc gat      1488
Pro Lys Ala Leu Pro Gly Val Asn Pro Ala Ile Leu Asp Pro Arg Asp
                485                 490                 495 act tat gcg gat aaa gcg caa tgg gaa gaa aaa gct caa gat ctt gca      1536
Thr Tyr Ala Asp Lys Ala Gln Trp Glu Glu Lys Ala Gln Asp Leu Ala
            500                 505                 510 ggt cgc ttt gtg aaa aac ttt gaa aaa tat acc ggt acg gcg gaa ggt      1584
Gly Arg Phe Val Lys Asn Phe Glu Lys Tyr Thr Gly Thr Ala Glu Gly
        515                 520                 525 cag gca tta gtt gct gcc ggt cct aaa gca taa                          1617
Gln Ala Leu Val Ala Ala Gly Pro Lys Ala
    530                 535

<210> SEQ ID NO 13
<211> LENGTH: 538
```

<212> TYPE: PRT
<213> ORGANISM: Mannheimia succiniciproducens

<400> SEQUENCE: 13

```
Met Thr Asp Leu Asn Gln Leu Thr Gln Glu Leu Gly Ala Leu Gly Ile
1               5                   10                  15

His Asp Val Gln Glu Val Val Tyr Asn Pro Ser Tyr Glu Leu Leu Phe
            20                  25                  30

Ala Glu Glu Thr Lys Pro Gly Leu Glu Gly Tyr Glu Lys Gly Thr Val
        35                  40                  45

Thr Asn Gln Gly Ala Val Ala Val Asn Thr Gly Ile Phe Thr Gly Arg
    50                  55                  60

Ser Pro Lys Asp Lys Tyr Ile Val Leu Asp Asp Lys Thr Lys Asp Thr
65                  70                  75                  80

Val Trp Trp Thr Ser Glu Lys Val Lys Asn Asp Asn Lys Pro Met Ser
                85                  90                  95

Gln Asp Thr Trp Asn Ser Leu Lys Gly Leu Val Ala Gln Leu Ser
            100                 105                 110

Gly Lys Arg Leu Phe Val Val Asp Ala Phe Cys Gly Ala Asn Lys Asp
        115                 120                 125

Thr Arg Leu Ala Val Arg Val Val Thr Glu Val Ala Trp Gln Ala His
    130                 135                 140

Phe Val Thr Asn Met Phe Ile Arg Pro Ser Ala Glu Glu Leu Lys Gly
145                 150                 155                 160

Phe Lys Pro Asp Phe Val Val Met Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Val Gln Leu Ile Gly Gly Thr Trp Tyr Gly Gly Glu
        195                 200                 205

Met Lys Lys Gly Met Phe Ser Met Met Asn Tyr Phe Leu Pro Leu Arg
    210                 215                 220

Gly Ile Ala Ser Met His Cys Ser Ala Asn Val Gly Lys Asp Gly Asp
225                 230                 235                 240

Thr Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Asp Glu Gly Val Phe Asn Phe Glu Gly Gly Cys Tyr Ala Lys Thr Ile
        275                 280                 285

Asn Leu Ser Ala Glu Asn Glu Pro Asp Ile Tyr Gly Ala Ile Lys Arg
    290                 295                 300

Asp Ala Leu Leu Glu Asn Val Val Leu Asp Asn Gly Asp Val Asp
305                 310                 315                 320

Tyr Ala Asp Gly Ser Lys Thr Glu Asn Thr Arg Val Ser Tyr Pro Ile
                325                 330                 335

Tyr His Ile Gln Asn Ile Val Lys Pro Val Ser Lys Ala Gly Pro Ala
            340                 345                 350

Thr Lys Val Ile Phe Leu Ser Ala Asp Ala Phe Gly Val Leu Pro Pro
        355                 360                 365

Val Ser Lys Leu Thr Pro Glu Gln Thr Lys Tyr Tyr Phe Leu Ser Gly
    370                 375                 380

Phe Thr Ala Lys Leu Ala Gly Thr Glu Arg Gly Ile Thr Glu Pro Thr
385                 390                 395                 400
```

```
Pro Thr Phe Ser Ala Cys Phe Gly Ala Ala Phe Leu Ser Leu His Pro
            405                 410                 415

Thr Gln Tyr Ala Glu Val Leu Val Lys Arg Met Gln Glu Ser Gly Ala
        420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
    450                 455                 460

Ile Asp Lys Ala Glu Met Gly Ser Leu Pro Ile Phe Asp Phe Ser Ile
465                 470                 475                 480

Pro Lys Ala Leu Pro Gly Val Asn Pro Ala Ile Leu Asp Pro Arg Asp
                485                 490                 495

Thr Tyr Ala Asp Lys Ala Gln Trp Glu Glu Lys Ala Gln Asp Leu Ala
            500                 505                 510

Gly Arg Phe Val Lys Asn Phe Glu Lys Tyr Thr Gly Thr Ala Glu Gly
        515                 520                 525

Gln Ala Leu Val Ala Ala Gly Pro Lys Ala
        530                 535

<210> SEQ ID NO 14
<211> LENGTH: 1620
<212> TYPE: DNA
<213> ORGANISM: Yersinia pseudotuberculosis
<220> FEATURE:
<221> NAME/KEY: CDS
<222> LOCATION: (1)..(1620)

<400> SEQUENCE: 14 atg agt gtt aaa gga att acc ccg cag gag ctc gcc gcc tat ggc atc      48
Met Ser Val Lys Gly Ile Thr Pro Gln Glu Leu Ala Ala Tyr Gly Ile
1               5                   10                  15 cat aac gtc agc gag att gtt tac aac cca agc tat gat tta ctg ttt      96
His Asn Val Ser Glu Ile Val Tyr Asn Pro Ser Tyr Asp Leu Leu Phe
            20                  25                  30 gaa gaa gag acc aaa ccc acg ttg gaa gga tac gaa cgt ggc aca ctg     144
Glu Glu Glu Thr Lys Pro Thr Leu Glu Gly Tyr Glu Arg Gly Thr Leu
        35                  40                  45 acg act acc ggc gca ata gcg gta gat acc ggt att ttt acc ggg cgt     192
Thr Thr Thr Gly Ala Ile Ala Val Asp Thr Gly Ile Phe Thr Gly Arg
    50                  55                  60 tca ccc aaa gat aaa tat att gtc cgc gat gct atc act cag gat acc     240
Ser Pro Lys Asp Lys Tyr Ile Val Arg Asp Ala Ile Thr Gln Asp Thr
65                  70                  75                  80 gtg tgg tgg gcc gat cag ggc aaa ggt aaa aat gat aat aag cct ctg     288
Val Trp Trp Ala Asp Gln Gly Lys Gly Lys Asn Asp Asn Lys Pro Leu
                85                  90                  95 agc caa gag atc tgg agc cat ttg aaa ggt ctg gtg acg gaa caa ctc     336
Ser Gln Glu Ile Trp Ser His Leu Lys Gly Leu Val Thr Glu Gln Leu
            100                 105                 110 tct ggc aaa cgc ctc ttt gtt gtc gat aca ttc tgc ggt gct aat gcg     384
Ser Gly Lys Arg Leu Phe Val Val Asp Thr Phe Cys Gly Ala Asn Ala
        115                 120                 125 gat acc cgc ctg caa gtc cgc ttt atc aca gaa gtc gct tgg cag gca     432
Asp Thr Arg Leu Gln Val Arg Phe Ile Thr Glu Val Ala Trp Gln Ala
    130                 135                 140 cac ttc gtc aaa aat atg ttt atc cgt cca tca gat gaa gaa ctg gct     480
His Phe Val Lys Asn Met Phe Ile Arg Pro Ser Asp Glu Glu Leu Ala
145                 150                 155                 160 cgg ttt gaa cct gac ttt atc gtg atg aac ggt gcc aaa tgc act aac     528
Arg Phe Glu Pro Asp Phe Ile Val Met Asn Gly Ala Lys Cys Thr Asn
```

```
                165                 170                 175
cca caa tgg aaa gag cag ggc ctg aat tca gaa aac ttt gtc gcc ttt       576
Pro Gln Trp Lys Glu Gln Gly Leu Asn Ser Glu Asn Phe Val Ala Phe
            180                 185                 190 aat ctg aca gaa cgt atg cag ttg att ggt ggc acg tgg tat ggc ggc       624
Asn Leu Thr Glu Arg Met Gln Leu Ile Gly Gly Thr Trp Tyr Gly Gly
                195                 200                 205 gaa atg aag aaa ggg atg ttc tca atg atg aac tac ctg ctg cca ctg       672
Glu Met Lys Lys Gly Met Phe Ser Met Met Asn Tyr Leu Leu Pro Leu
    210                 215                 220 aaa ggc att gct tca atg cat tgt tca gct aac gtc ggc gaa aaa ggc       720
Lys Gly Ile Ala Ser Met His Cys Ser Ala Asn Val Gly Glu Lys Gly
225                 230                 235                 240 gat gtt gcc atc ttc ttc ggt ctg tcg ggt acc ggt aaa acc act tta       768
Asp Val Ala Ile Phe Phe Gly Leu Ser Gly Thr Gly Lys Thr Thr Leu
                245                 250                 255 tct acc gat cca aaa cgc aag ttg atc ggt gat gat gaa cat ggc tgg       816
Ser Thr Asp Pro Lys Arg Lys Leu Ile Gly Asp Asp Glu His Gly Trp
            260                 265                 270 gat gat gat ggc gtc ttt aac ttc gag ggg ggg tgc tac gct aaa acc       864
Asp Asp Asp Gly Val Phe Asn Phe Glu Gly Gly Cys Tyr Ala Lys Thr
                275                 280                 285 atc aag tta tct gaa gaa gca gag cca gat att tac cac gcc att aaa       912
Ile Lys Leu Ser Glu Glu Ala Glu Pro Asp Ile Tyr His Ala Ile Lys
    290                 295                 300 cgc gac gcc ttg ctg gaa aac gtg gtg gtg cta gca gac ggt acc gtt       960
Arg Asp Ala Leu Leu Glu Asn Val Val Val Leu Ala Asp Gly Thr Val
305                 310                 315                 320 gat ttt aat gac ggt tct aaa act gaa aac acc cgt gtc tct tat ccg      1008
Asp Phe Asn Asp Gly Ser Lys Thr Glu Asn Thr Arg Val Ser Tyr Pro
                325                 330                 335 att tac cac att gat aac att gtt aaa ccg gtg tcc aaa gca ggc cat      1056
Ile Tyr His Ile Asp Asn Ile Val Lys Pro Val Ser Lys Ala Gly His
            340                 345                 350 gcg acc aag gtt atc ttc ctg act gcc gat gcc ttt ggt gtg ctc ccc      1104
Ala Thr Lys Val Ile Phe Leu Thr Ala Asp Ala Phe Gly Val Leu Pro
                355                 360                 365 cca gta tct cgt ctg acc gca aac cag acg caa tat cac ttc ctc tct      1152
Pro Val Ser Arg Leu Thr Ala Asn Gln Thr Gln Tyr His Phe Leu Ser
    370                 375                 380 ggc ttt act gcc aaa ctg gca ggg aca gag cgt ggc gtc acg gag cca      1200
Gly Phe Thr Ala Lys Leu Ala Gly Thr Glu Arg Gly Val Thr Glu Pro
385                 390                 395                 400 aca cca acc ttc tct gct tgc ttt ggt gcg gcc ttc ctg tct ctg cac      1248
Thr Pro Thr Phe Ser Ala Cys Phe Gly Ala Ala Phe Leu Ser Leu His
                405                 410                 415 cca acg cag tac gct gaa gtg ctg gtt aag cgt atg caa gcg gtt ggc      1296
Pro Thr Gln Tyr Ala Glu Val Leu Val Lys Arg Met Gln Ala Val Gly
            420                 425                 430 gca caa gcc tat ctg gtc aat acc ggt tgg aac ggg aca ggt aag cgt      1344
Ala Gln Ala Tyr Leu Val Asn Thr Gly Trp Asn Gly Thr Gly Lys Arg
                435                 440                 445 att tcc atc aag gat acc cgc gcc att att gac gca atc cta aac ggg      1392
Ile Ser Ile Lys Asp Thr Arg Ala Ile Ile Asp Ala Ile Leu Asn Gly
    450                 455                 460 gag att gat aag gca gaa acc ttt acg ctg cca atc ttt gat ctg gca      1440
Glu Ile Asp Lys Ala Glu Thr Phe Thr Leu Pro Ile Phe Asp Leu Ala
465                 470                 475                 480 gtc cct atg gcg tta ccc ggt gtg aat ccc gat atc ctc gat cct cgc      1488
Val Pro Met Ala Leu Pro Gly Val Asn Pro Asp Ile Leu Asp Pro Arg
```

```
                              485                 490                 495
gac acc tac gcc gat aaa gcg caa tgg caa gag aaa gcc gaa gat ttg      1536
Asp Thr Tyr Ala Asp Lys Ala Gln Trp Gln Glu Lys Ala Glu Asp Leu
            500                 505                 510 gcg aaa cgc ttt gcg act aac ttt gat aaa tac act gat acc cct gcg      1584
Ala Lys Arg Phe Ala Thr Asn Phe Asp Lys Tyr Thr Asp Thr Pro Ala
        515                 520                 525 ggg gcc gcg ttg gtt agc gcg ggg cca aag atc taa                      1620
Gly Ala Ala Leu Val Ser Ala Gly Pro Lys Ile
    530                 535

<210> SEQ ID NO 15
<211> LENGTH: 539
<212> TYPE: PRT
<213> ORGANISM: Yersinia pseudotuberculosis

<400> SEQUENCE: 15

Met Ser Val Lys Gly Ile Thr Pro Gln Glu Leu Ala Ala Tyr Gly Ile
1               5                   10                  15

His Asn Val Ser Glu Ile Val Tyr Asn Pro Ser Tyr Asp Leu Leu Phe
            20                  25                  30

Glu Glu Glu Thr Lys Pro Thr Leu Glu Gly Tyr Glu Arg Gly Thr Leu
        35                  40                  45

Thr Thr Thr Gly Ala Ile Ala Val Asp Thr Gly Ile Phe Thr Gly Arg
    50                  55                  60

Ser Pro Lys Asp Lys Tyr Ile Val Arg Asp Ala Ile Thr Gln Asp Thr
65                  70                  75                  80

Val Trp Trp Ala Asp Gln Gly Lys Gly Lys Asn Asp Asn Lys Pro Leu
                85                  90                  95

Ser Gln Glu Ile Trp Ser His Leu Lys Gly Leu Val Thr Glu Gln Leu
            100                 105                 110

Ser Gly Lys Arg Leu Phe Val Val Asp Thr Phe Cys Gly Ala Asn Ala
        115                 120                 125

Asp Thr Arg Leu Gln Val Arg Phe Ile Thr Glu Val Ala Trp Gln Ala
    130                 135                 140

His Phe Val Lys Asn Met Phe Ile Arg Pro Ser Asp Glu Glu Leu Ala
145                 150                 155                 160

Arg Phe Glu Pro Asp Phe Ile Val Met Asn Gly Ala Lys Cys Thr Asn
                165                 170                 175

Pro Gln Trp Lys Glu Gln Gly Leu Asn Ser Glu Asn Phe Val Ala Phe
            180                 185                 190

Asn Leu Thr Glu Arg Met Gln Leu Ile Gly Gly Thr Trp Tyr Gly Gly
        195                 200                 205

Glu Met Lys Lys Gly Met Phe Ser Met Met Asn Tyr Leu Leu Pro Leu
    210                 215                 220

Lys Gly Ile Ala Ser Met His Cys Ser Ala Asn Val Gly Glu Lys Gly
225                 230                 235                 240

Asp Val Ala Ile Phe Phe Gly Leu Ser Gly Thr Gly Lys Thr Thr Leu
                245                 250                 255

Ser Thr Asp Pro Lys Arg Lys Leu Ile Gly Asp Asp Glu His Gly Trp
            260                 265                 270

Asp Asp Asp Gly Val Phe Asn Phe Glu Gly Gly Cys Tyr Ala Lys Thr
        275                 280                 285

Ile Lys Leu Ser Glu Glu Ala Glu Pro Asp Ile Tyr His Ala Ile Lys
    290                 295                 300

Arg Asp Ala Leu Leu Glu Asn Val Val Val Leu Ala Asp Gly Thr Val
```

```
                305                 310                 315                 320
Asp Phe Asn Asp Gly Ser Lys Thr Glu Asn Thr Arg Val Ser Tyr Pro
            325                 330                 335

Ile Tyr His Ile Asp Asn Ile Val Lys Pro Val Ser Lys Ala Gly His
            340                 345                 350

Ala Thr Lys Val Ile Phe Leu Thr Ala Asp Ala Phe Gly Val Leu Pro
            355                 360                 365

Pro Val Ser Arg Leu Thr Ala Asn Gln Thr Gln Tyr His Phe Leu Ser
370                 375                 380

Gly Phe Thr Ala Lys Leu Ala Gly Thr Glu Arg Gly Val Thr Glu Pro
385                 390                 395                 400

Thr Pro Thr Phe Ser Ala Cys Phe Gly Ala Ala Phe Leu Ser Leu His
                405                 410                 415

Pro Thr Gln Tyr Ala Glu Val Leu Val Lys Arg Met Gln Ala Val Gly
            420                 425                 430

Ala Gln Ala Tyr Leu Val Asn Thr Gly Trp Asn Gly Thr Gly Lys Arg
            435                 440                 445

Ile Ser Ile Lys Asp Thr Arg Ala Ile Asp Ala Ile Leu Asn Gly
450                 455                 460

Glu Ile Asp Lys Ala Glu Thr Phe Thr Leu Pro Ile Phe Asp Leu Ala
465                 470                 475                 480

Val Pro Met Ala Leu Pro Gly Val Asn Pro Asp Ile Leu Asp Pro Arg
                485                 490                 495

Asp Thr Tyr Ala Asp Lys Ala Gln Trp Gln Glu Lys Ala Glu Asp Leu
            500                 505                 510

Ala Lys Arg Phe Ala Thr Asn Phe Asp Lys Tyr Thr Asp Thr Pro Ala
            515                 520                 525

Gly Ala Ala Leu Val Ser Ala Gly Pro Lys Ile
            530                 535

<210> SEQ ID NO 16
<211> LENGTH: 1629
<212> TYPE: DNA
<213> ORGANISM: Vibrio cholerae
<220> FEATURE:
<221> NAME/KEY: CDS
<222> LOCATION: (1)..(1629)

<400> SEQUENCE: 16 atg acc gtt atg gaa cat act aag gct gca caa atc gac cta gcc caa      48
Met Thr Val Met Glu His Thr Lys Ala Ala Gln Ile Asp Leu Ala Gln
1               5                   10                  15 tat ggg atc acc ggc gta act gaa ctg gtt cgt aac ccg agc tat gaa      96
Tyr Gly Ile Thr Gly Val Thr Glu Leu Val Arg Asn Pro Ser Tyr Glu
            20                  25                  30 atg tta ttt gcc gaa gaa acc cgt tca gat ctc gaa ggt tat gaa cgt     144
Met Leu Phe Ala Glu Glu Thr Arg Ser Asp Leu Glu Gly Tyr Glu Arg
        35                  40                  45 ggt gtg gtg act gaa ttg ggt gct gtt gcg gtt gat act ggc atc ttc     192
Gly Val Val Thr Glu Leu Gly Ala Val Ala Val Asp Thr Gly Ile Phe
    50                  55                  60 act ggc cgc tca cca aaa gat aag ttt atc gtt aaa gat gat acc act     240
Thr Gly Arg Ser Pro Lys Asp Lys Phe Ile Val Lys Asp Asp Thr Thr
65                  70                  75                  80 cgc gat acg ctg tgg tgg acg tca gac aaa gcg aaa aac gac aac aaa     288
Arg Asp Thr Leu Trp Trp Thr Ser Asp Lys Ala Lys Asn Asp Asn Lys
                85                  90                  95 ccg atc aat caa gaa gtg tgg aat gac ctg aaa gcc ttg gtg acc aag     336
```

```
                Pro Ile Asn Gln Glu Val Trp Asn Asp Leu Lys Ala Leu Val Thr Lys
                                100                 105                 110 cag ctt tct ggt aaa cgc gta ttt gtg ctc gat ggc tac tgt ggt gcc      384
Gln Leu Ser Gly Lys Arg Val Phe Val Leu Asp Gly Tyr Cys Gly Ala
            115                 120                 125 aac gcc gat act cgc tta agt gtt cgc ttc atc acc gaa gta gca tgg      432
Asn Ala Asp Thr Arg Leu Ser Val Arg Phe Ile Thr Glu Val Ala Trp
        130                 135                 140 caa gca cac ttt gtg aaa aac atg ttc att cgt cca agc gaa gaa gag      480
Gln Ala His Phe Val Lys Asn Met Phe Ile Arg Pro Ser Glu Glu Glu
145                 150                 155                 160 ctg gca cac ttt aaa cca gac ttt gtc gta atg aac ggc gca aaa tgt      528
Leu Ala His Phe Lys Pro Asp Phe Val Val Met Asn Gly Ala Lys Cys
                165                 170                 175 acc aat gcg aag tgg aaa gag cac ggt ctg aac tca gaa aac ttc act      576
Thr Asn Ala Lys Trp Lys Glu His Gly Leu Asn Ser Glu Asn Phe Thr
            180                 185                 190 gtg ttt aac ctg acc gag cgc atg cag ctc atc ggc ggt act tgg tac      624
Val Phe Asn Leu Thr Glu Arg Met Gln Leu Ile Gly Gly Thr Trp Tyr
        195                 200                 205 ggc ggt gag atg aaa aaa ggt atg ttc gcg atg atg aac tac ttc ctg      672
Gly Gly Glu Met Lys Lys Gly Met Phe Ala Met Met Asn Tyr Phe Leu
    210                 215                 220 ccg cta caa ggc att gcc tct atg cac tgc tct gcc aac atg ggt aaa      720
Pro Leu Gln Gly Ile Ala Ser Met His Cys Ser Ala Asn Met Gly Lys
225                 230                 235                 240 gcg ggc gat gtc gcc atc ttc ttc ggt ctt tct ggt acg ggt aaa acc      768
Ala Gly Asp Val Ala Ile Phe Phe Gly Leu Ser Gly Thr Gly Lys Thr
                245                 250                 255 acc cta tcc acc gat cca aaa cgt gcg tta att ggt gac gat gag cac      816
Thr Leu Ser Thr Asp Pro Lys Arg Ala Leu Ile Gly Asp Asp Glu His
            260                 265                 270 ggc tgg gat gat gat ggc gtg ttc aac ttt gaa ggc ggc tgc tac gcg      864
Gly Trp Asp Asp Asp Gly Val Phe Asn Phe Glu Gly Gly Cys Tyr Ala
        275                 280                 285 aaa acc atc aag ctg tct aaa gaa gca gag ccg gat atc tat aac gcg      912
Lys Thr Ile Lys Leu Ser Lys Glu Ala Glu Pro Asp Ile Tyr Asn Ala
    290                 295                 300 atc cgc cgt gat gct cta ctg gaa aac gtc acg gtt cgt agt gat ggt      960
Ile Arg Arg Asp Ala Leu Leu Glu Asn Val Thr Val Arg Ser Asp Gly
305                 310                 315                 320 tcg att gat ttt gat gat ggt tca aaa acc gag aac acc cgt gtt tct     1008
Ser Ile Asp Phe Asp Asp Gly Ser Lys Thr Glu Asn Thr Arg Val Ser
                325                 330                 335 tac cct att tat cac atc gac aac atc gta aaa ccc gtt tcc aaa ggc     1056
Tyr Pro Ile Tyr His Ile Asp Asn Ile Val Lys Pro Val Ser Lys Gly
            340                 345                 350 ggt cat gcg act aag gtg atc ttc ctg tct gcc gat gcg ttt ggc gta     1104
Gly His Ala Thr Lys Val Ile Phe Leu Ser Ala Asp Ala Phe Gly Val
        355                 360                 365 ttg cct cca gtt tca aaa ctg acg cca gag caa acc aag tac cac ttc     1152
Leu Pro Pro Val Ser Lys Leu Thr Pro Glu Gln Thr Lys Tyr His Phe
370                 375                 380 ttg tct ggc ttt acg gct aaa ctg gca ggt act gag cgt ggc att act     1200
Leu Ser Gly Phe Thr Ala Lys Leu Ala Gly Thr Glu Arg Gly Ile Thr
385                 390                 395                 400 gaa cct acc cca acc ttc tcc gcc tgt ttt ggc gca gcg ttc ctc act     1248
Glu Pro Thr Pro Thr Phe Ser Ala Cys Phe Gly Ala Ala Phe Leu Thr
                405                 410                 415 ctg cac cca act cag tat gca gaa gtg ctg gta aaa cgt atg gaa gca     1296
```

```
Leu His Pro Thr Gln Tyr Ala Glu Val Leu Val Lys Arg Met Glu Ala
            420                 425                 430 gcg ggc gcc gaa gcc tat ctg gtt aac aca ggt tgg aac ggc agc ggt      1344
Ala Gly Ala Glu Ala Tyr Leu Val Asn Thr Gly Trp Asn Gly Ser Gly
            435                 440                 445 aag cgc atc tca att aaa gat acg cgc ggt att atc gat gcg att ttg      1392
Lys Arg Ile Ser Ile Lys Asp Thr Arg Gly Ile Ile Asp Ala Ile Leu
            450                 455                 460 gat ggt tcg atc gaa aaa gcg gaa acc aaa cag atc cca atc ttt aat      1440
Asp Gly Ser Ile Glu Lys Ala Glu Thr Lys Gln Ile Pro Ile Phe Asn
465                 470                 475                 480 ctg caa gtg ccc acc gca ctg ccc ggc gtc gat cct atg atc ctc gac      1488
Leu Gln Val Pro Thr Ala Leu Pro Gly Val Asp Pro Met Ile Leu Asp
                        485                 490                 495 cca cgt gat act tat gtt gac cca ctg cag tgg gaa agc aaa gcc aaa      1536
Pro Arg Asp Thr Tyr Val Asp Pro Leu Gln Trp Glu Ser Lys Ala Lys
                500                 505                 510 gac ttg gca acg cgc ttc atc aac aac ttc gac aag tac acg gat aac      1584
Asp Leu Ala Thr Arg Phe Ile Asn Asn Phe Asp Lys Tyr Thr Asp Asn
            515                 520                 525 gcc gaa ggt aaa gca ctg gtt gcc gcg ggt cca aag ctc gac taa          1629
Ala Glu Gly Lys Ala Leu Val Ala Ala Gly Pro Lys Leu Asp
            530                 535                 540

<210> SEQ ID NO 17
<211> LENGTH: 542
<212> TYPE: PRT
<213> ORGANISM: Vibrio cholerae

<400> SEQUENCE: 17

Met Thr Val Met Glu His Thr Lys Ala Ala Gln Ile Asp Leu Ala Gln
1               5                   10                  15

Tyr Gly Ile Thr Gly Val Thr Glu Leu Val Arg Asn Pro Ser Tyr Glu
            20                  25                  30

Met Leu Phe Ala Glu Glu Thr Arg Ser Asp Leu Glu Gly Tyr Glu Arg
        35                  40                  45

Gly Val Val Thr Glu Leu Gly Ala Val Ala Val Asp Thr Gly Ile Phe
    50                  55                  60

Thr Gly Arg Ser Pro Lys Asp Lys Phe Ile Val Lys Asp Asp Thr Thr
65                  70                  75                  80

Arg Asp Thr Leu Trp Trp Thr Ser Asp Lys Ala Lys Asn Asp Asn Lys
                85                  90                  95

Pro Ile Asn Gln Glu Val Trp Asn Asp Leu Lys Ala Leu Val Thr Lys
            100                 105                 110

Gln Leu Ser Gly Lys Arg Val Phe Val Leu Asp Gly Tyr Cys Gly Ala
        115                 120                 125

Asn Ala Asp Thr Arg Leu Ser Val Arg Phe Ile Thr Glu Val Ala Trp
    130                 135                 140

Gln Ala His Phe Val Lys Asn Met Phe Ile Arg Pro Ser Glu Glu Glu
145                 150                 155                 160

Leu Ala His Phe Lys Pro Asp Phe Val Val Met Asn Gly Ala Lys Cys
                165                 170                 175

Thr Asn Ala Lys Trp Lys Glu His Gly Leu Asn Ser Glu Asn Phe Thr
            180                 185                 190

Val Phe Asn Leu Thr Glu Arg Met Gln Leu Ile Gly Gly Thr Trp Tyr
        195                 200                 205

Gly Gly Glu Met Lys Lys Gly Met Phe Ala Met Met Asn Tyr Phe Leu
    210                 215                 220
```

Pro Leu Gln Gly Ile Ala Ser Met His Cys Ser Ala Asn Met Gly Lys
225                 230                 235                 240

Ala Gly Asp Val Ala Ile Phe Phe Gly Leu Ser Gly Thr Gly Lys Thr
            245                 250                 255

Thr Leu Ser Thr Asp Pro Lys Arg Ala Leu Ile Gly Asp Asp Glu His
        260                 265                 270

Gly Trp Asp Asp Asp Gly Val Phe Asn Phe Glu Gly Gly Cys Tyr Ala
    275                 280                 285

Lys Thr Ile Lys Leu Ser Lys Glu Ala Glu Pro Asp Ile Tyr Asn Ala
290                 295                 300

Ile Arg Arg Asp Ala Leu Leu Glu Asn Val Thr Val Arg Ser Asp Gly
305                 310                 315                 320

Ser Ile Asp Phe Asp Asp Gly Ser Lys Thr Glu Asn Thr Arg Val Ser
                325                 330                 335

Tyr Pro Ile Tyr His Ile Asp Asn Ile Val Lys Pro Val Ser Lys Gly
            340                 345                 350

Gly His Ala Thr Lys Val Ile Phe Leu Ser Ala Asp Ala Phe Gly Val
        355                 360                 365

Leu Pro Pro Val Ser Lys Leu Thr Pro Glu Gln Thr Lys Tyr His Phe
370                 375                 380

Leu Ser Gly Phe Thr Ala Lys Leu Ala Gly Thr Glu Arg Gly Ile Thr
385                 390                 395                 400

Glu Pro Thr Pro Thr Phe Ser Ala Cys Phe Gly Ala Ala Phe Leu Thr
                405                 410                 415

Leu His Pro Thr Gln Tyr Ala Glu Val Leu Val Lys Arg Met Glu Ala
            420                 425                 430

Ala Gly Ala Glu Ala Tyr Leu Val Asn Thr Gly Trp Asn Gly Ser Gly
        435                 440                 445

Lys Arg Ile Ser Ile Lys Asp Thr Arg Gly Ile Ile Asp Ala Ile Leu
450                 455                 460

Asp Gly Ser Ile Glu Lys Ala Glu Thr Lys Gln Ile Pro Ile Phe Asn
465                 470                 475                 480

Leu Gln Val Pro Thr Ala Leu Pro Gly Val Asp Pro Met Ile Leu Asp
                485                 490                 495

Pro Arg Asp Thr Tyr Val Asp Pro Leu Gln Trp Glu Ser Lys Ala Lys
            500                 505                 510

Asp Leu Ala Thr Arg Phe Ile Asn Asn Phe Asp Lys Tyr Thr Asp Asn
        515                 520                 525

Ala Glu Gly Lys Ala Leu Val Ala Ala Gly Pro Lys Leu Asp
530                 535                 540

<210> SEQ ID NO 18
<211> LENGTH: 89
<212> TYPE: DNA
<213> ORGANISM: Artificial Sequence
<220> FEATURE:
<223> OTHER INFORMATION: primer for deleting adhE

<400> SEQUENCE: 18
caagttgata agatcttccg tgccgccgct ctggccgctg cagatgctcg aatccctctc    60
tgaagcctgc ttttttatac taagttggc                                     89

<210> SEQ ID NO 19
<211> LENGTH: 89
<212> TYPE: DNA
<213> ORGANISM: Artificial Sequence
<220> FEATURE:
<223> OTHER INFORMATION: primer for deleting adhE

<400> SEQUENCE: 19
acgtgagcca ggaaatcagc ttcctgaacg ccggcttcgc gaatagattt cggaataccc    60
gctcaagtta gtataaaaaa gctgaacga                                      89

<210> SEQ ID NO 20
<211> LENGTH: 1261
<212> TYPE: DNA
<213> ORGANISM: Enterobacter aerogenes
<220> FEATURE:
<221> NAME/KEY: CDS
<222> LOCATION: (147)..(1136)

<400> SEQUENCE: 20
aacgtattgt cttttaaaga gatttcttaa gactgcgata tgctctagaa ttaatatcat    60
aacctgatga ttaaactaat ttttaatatc tgtaagatta ttttaattat gctaccgtga   120
cggtattatc actagaggaa agcctt atg aaa atc gct gtt tat agt acc aag   173
                              Met Lys Ile Ala Val Tyr Ser Thr Lys
                              1               5 cag tac gat aaa aag tat ctg cag cat gtt aac gac gca tac ggc ttt    221
Gln Tyr Asp Lys Lys Tyr Leu Gln His Val Asn Asp Ala Tyr Gly Phe
 10              15                  20                  25 gaa ctg gaa ttt ttc gac ttc ctg ctg acc gaa aag acc gcg aaa acg    269
Glu Leu Glu Phe Phe Asp Phe Leu Leu Thr Glu Lys Thr Ala Lys Thr
                 30                  35                  40 gcc aac ggc tgt gaa gcg gta tgt atc ttc gtt aac gac gac ggc agc    317
Ala Asn Gly Cys Glu Ala Val Cys Ile Phe Val Asn Asp Asp Gly Ser
             45                  50                  55 cgc ccg gtg ctg gaa gag cta aaa gcc cac ggc gtg aaa tac atc gca    365
Arg Pro Val Leu Glu Glu Leu Lys Ala His Gly Val Lys Tyr Ile Ala
 60                  65                  70 cta cgc tgc gcc ggc ttt aac aac gtc gat ctt gat gcg gct aaa gag    413
Leu Arg Cys Ala Gly Phe Asn Asn Val Asp Leu Asp Ala Ala Lys Glu
 75                  80                  85 ctg ggc ctg cgc gtc gtg cgc gtc ccg gcc tac tcg ccg gaa gcc gtt    461
Leu Gly Leu Arg Val Val Arg Val Pro Ala Tyr Ser Pro Glu Ala Val
 90                  95                 100                 105 gct gaa cac gcc atc ggt atg atg atg tcg ttg aac cgt cgc att cac    509
Ala Glu His Ala Ile Gly Met Met Met Ser Leu Asn Arg Arg Ile His
                110                 115                 120 cgc gcc tat cag cgt acc cgc gat gcc aac ttc tcg ctg gaa ggg ctg    557
Arg Ala Tyr Gln Arg Thr Arg Asp Ala Asn Phe Ser Leu Glu Gly Leu
            125                 130                 135 acc ggc ttc acg atg tac ggc aaa acc gca ggg gtg atc ggc acc ggt    605
Thr Gly Phe Thr Met Tyr Gly Lys Thr Ala Gly Val Ile Gly Thr Gly
        140                 145                 150 aaa atc ggc gtc gcg acg ctg cgg atc ctc aaa ggt ttc ggt atg cgc    653
Lys Ile Gly Val Ala Thr Leu Arg Ile Leu Lys Gly Phe Gly Met Arg
    155                 160                 165 ctg ctg gcg ttt gat ccc tac ccg agc gcg gcg ctg gat ctc ggc        701
Leu Leu Ala Phe Asp Pro Tyr Pro Ser Ala Ala Ala Leu Asp Leu Gly
170                 175                 180                 185 gtt gaa tat gtc gac ctg ccg acg ctg tac gcg cag tcc gac gtc atc    749
Val Glu Tyr Val Asp Leu Pro Thr Leu Tyr Ala Gln Ser Asp Val Ile
                190                 195                 200 tcc ctg cac tgc ccg ctt acc aac gaa aac tat cac ctg ctc aac cag    797
Ser Leu His Cys Pro Leu Thr Asn Glu Asn Tyr His Leu Leu Asn Gln
            205                 210                 215

```
gcg gca ttc gat cag atg aaa gac ggc gtg atg gtc att aat acc agc    845
Ala Ala Phe Asp Gln Met Lys Asp Gly Val Met Val Ile Asn Thr Ser
        220                 225                 230 cgc ggc gcg cta ata gat tca caa gcg gct atc gac gcg ctg aag cat    893
Arg Gly Ala Leu Ile Asp Ser Gln Ala Ala Ile Asp Ala Leu Lys His
    235                 240                 245 cag aaa atc ggc gca ctg gga atg gac gtg tat gaa aat gaa cgc gat    941
Gln Lys Ile Gly Ala Leu Gly Met Asp Val Tyr Glu Asn Glu Arg Asp
250                 255                 260                 265 ctg ttc ttt gaa gat aaa tcg aat gat gtc atc cag gat gac gtg ttc    989
Leu Phe Phe Glu Asp Lys Ser Asn Asp Val Ile Gln Asp Asp Val Phe
                270                 275                 280 cgc cgg ctc tcc gcc tgc cac aac gtc ctg ttt acc ggg cac cag gca   1037
Arg Arg Leu Ser Ala Cys His Asn Val Leu Phe Thr Gly His Gln Ala
            285                 290                 295 ttc ctg acg gct gag gcg ctg atc ggt att tcc gag aca acg ctt ggc   1085
Phe Leu Thr Ala Glu Ala Leu Ile Gly Ile Ser Glu Thr Thr Leu Gly
        300                 305                 310 aat ctg cag cag gta gct aag ggc gaa acc tgc ccg aac gcg ctg gtc   1133
Asn Leu Gln Gln Val Ala Lys Gly Glu Thr Cys Pro Asn Ala Leu Val
    315                 320                 325 taa gcttctttcc cctttgtgc tcccgctaa cggggggcac attcagacaa          1186
tccccacaga tcctgcctgc attacagtta cactgttttt cgttttattg atatgacaaa 1246 tgttttggag tacga                                                  1261

<210> SEQ ID NO 21
<211> LENGTH: 3348
<212> TYPE: DNA
<213> ORGANISM: Enterobacter aerogenes
<220> FEATURE:
<221> NAME/KEY: CDS
<222> LOCATION: (301)..(3048)

<400> SEQUENCE: 21
atcattaacc ttgacttgac tggttaatta ttgacctgct gaaaggtatc agcatcgcca    60
aatattgatc caaatcacgt aattaatact cagaagtgag taatcttggc tacatcaaca   120
gagtgaaagg ccgaagtacc tgagtgcgta gtgagacaaa gcttttttag taaatcagtg   180
ggttcaaagc gttagaaatc tttacgttaa catttacatg caagctgtta acagcctgtc   240
tataatgtcg aatcgagcta ctgttttact aaaaaagttt aacattatca ggagagcatt   300 atg gct gtt act aat gtc gct gaa ctt aac gca ctt gta gag cgc gta    348
Met Ala Val Thr Asn Val Ala Glu Leu Asn Ala Leu Val Glu Arg Val
1               5                  10                  15 aaa aaa gcc cag cgt gaa tat gcc agt ttc act caa gaa caa gtt gat    396
Lys Lys Ala Gln Arg Glu Tyr Ala Ser Phe Thr Gln Glu Gln Val Asp
            20                  25                  30 aag atc ttc cgt gcc gcc gct ctg gcc gct gca gat gct cga atc cct    444
Lys Ile Phe Arg Ala Ala Ala Leu Ala Ala Ala Asp Ala Arg Ile Pro
        35                  40                  45 ctc gct aaa atg gct gtt gcc gaa tcc ggc atg ggt att att gaa gat    492
Leu Ala Lys Met Ala Val Ala Glu Ser Gly Met Gly Ile Ile Glu Asp
    50                  55                  60 aaa gtg atc aaa aac cac ttc gct tcc gaa tat atc tac aac gcc tat    540
Lys Val Ile Lys Asn His Phe Ala Ser Glu Tyr Ile Tyr Asn Ala Tyr
65                  70                  75                  80 aaa gat gaa aag acc tgt ggc gtc ctg tct gaa gac gac act ttc ggt    588
Lys Asp Glu Lys Thr Cys Gly Val Leu Ser Glu Asp Asp Thr Phe Gly
                85                  90                  95 acc atc acc att gct gag cca atc ggt att att tgc ggt atc gtc ccg    636
```

```
                Thr Ile Thr Ile Ala Glu Pro Ile Gly Ile Ile Cys Gly Ile Val Pro
                                100                 105                 110 act acc aac ccg act tct act gct atc ttc aaa tcg ctg atc agc ctg      684
Thr Thr Asn Pro Thr Ser Thr Ala Ile Phe Lys Ser Leu Ile Ser Leu
            115                 120                 125 aag acg cgt aac gcc atc atc ttc tct ccg cac ccg cgt gct aaa gac      732
Lys Thr Arg Asn Ala Ile Ile Phe Ser Pro His Pro Arg Ala Lys Asp
        130                 135                 140 gcg act aac aaa gcg gcg gac atc gta ttg cag gca gct att gcc gca      780
Ala Thr Asn Lys Ala Ala Asp Ile Val Leu Gln Ala Ala Ile Ala Ala
145                 150                 155                 160 ggc gcg ccg aaa gat ctg atc ggt tgg atc gac cag cct tcc gta gaa      828
Gly Ala Pro Lys Asp Leu Ile Gly Trp Ile Asp Gln Pro Ser Val Glu
                165                 170                 175 ctg tct aac gca ctg atg cat cat cct gac atc aac ctg atc ctc gcc      876
Leu Ser Asn Ala Leu Met His His Pro Asp Ile Asn Leu Ile Leu Ala
            180                 185                 190 acc ggc ggc cca ggt atg gtt aag gcc gct tat agc tcc ggt aaa cca      924
Thr Gly Gly Pro Gly Met Val Lys Ala Ala Tyr Ser Ser Gly Lys Pro
        195                 200                 205 gct atc ggc gtt ggc gcg ggc aac acg ccg gtt gtt att gat gaa acg      972
Ala Ile Gly Val Gly Ala Gly Asn Thr Pro Val Val Ile Asp Glu Thr
210                 215                 220 gct gat atc aaa cgc gct gtg gcg tcc gta ctg atg tca aaa acc ttc     1020
Ala Asp Ile Lys Arg Ala Val Ala Ser Val Leu Met Ser Lys Thr Phe
225                 230                 235                 240 gat aac ggc gtt atc tgt gct tct gaa caa tcc gtg gtg gtt gtc gac     1068
Asp Asn Gly Val Ile Cys Ala Ser Glu Gln Ser Val Val Val Val Asp
                245                 250                 255 tcc gtc tac gac gcc gtc cgc gag cgt ttt gcc agc cat ggc ggc tac     1116
Ser Val Tyr Asp Ala Val Arg Glu Arg Phe Ala Ser His Gly Gly Tyr
            260                 265                 270 ctg ctg cag ggt aaa gag ctg aaa gcc gtt cag gac atc atc ctg aaa     1164
Leu Leu Gln Gly Lys Glu Leu Lys Ala Val Gln Asp Ile Ile Leu Lys
        275                 280                 285 aat ggc gcg ctg aat gcg gcg atc gtt ggt caa cca gcg gca aaa atc     1212
Asn Gly Ala Leu Asn Ala Ala Ile Val Gly Gln Pro Ala Ala Lys Ile
290                 295                 300 gct gaa ctg gca ggc ttc acc gtg cca gcc acc act aag att ctg atc     1260
Ala Glu Leu Ala Gly Phe Thr Val Pro Ala Thr Thr Lys Ile Leu Ile
305                 310                 315                 320 ggc gaa gtt acc gac gtt gac gaa agc gaa ccg ttc gct cac gaa aaa     1308
Gly Glu Val Thr Asp Val Asp Glu Ser Glu Pro Phe Ala His Glu Lys
                325                 330                 335 ctg tct ccg acg ctg gca atg tac cgt gcg aaa gat ttc gaa gac gcg     1356
Leu Ser Pro Thr Leu Ala Met Tyr Arg Ala Lys Asp Phe Glu Asp Ala
            340                 345                 350 gtc aat aaa gca gaa aaa ctg gtc gcc atg ggc ggt atc ggt cac acc     1404
Val Asn Lys Ala Glu Lys Leu Val Ala Met Gly Gly Ile Gly His Thr
        355                 360                 365 tct tgc ctg tac acc gac cag gac aac cag ccg gct cgc gtg gcc tac     1452
Ser Cys Leu Tyr Thr Asp Gln Asp Asn Gln Pro Ala Arg Val Ala Tyr
370                 375                 380 ttc ggc cag atg atg aaa acc gcg cgt atc ctg atc aac acc ccg gct     1500
Phe Gly Gln Met Met Lys Thr Ala Arg Ile Leu Ile Asn Thr Pro Ala
385                 390                 395                 400 tcc cag ggt ggt atc ggc gac ctg tat aac ttc aag ctc gca cct tcc     1548
Ser Gln Gly Gly Ile Gly Asp Leu Tyr Asn Phe Lys Leu Ala Pro Ser
                405                 410                 415 ctg act ctg ggt tgt ggt tcc tgg ggt ggt aac tcc atc tct gaa aac     1596
```

| | | | | | | | | | | | | | | | |
|---|---|---|---|---|---|---|---|---|---|---|---|---|---|---|---|
|Leu|Thr|Leu|Gly|Cys|Gly|Ser|Trp|Gly|Gly|Asn|Ser|Ile|Ser|Glu|Asn|
| | | |420| | | |425| | | |430| | | | |

```
gtt ggt ccg aaa cac ctg atc aac aag aaa acc gtt gct aag cga gct     1644
Val Gly Pro Lys His Leu Ile Asn Lys Lys Thr Val Ala Lys Arg Ala
        435                 440                 445 gaa aac atg ttg tgg cat aaa ctt ccg aaa tct atc tac ttc cgt cgt     1692
Glu Asn Met Leu Trp His Lys Leu Pro Lys Ser Ile Tyr Phe Arg Arg
    450                 455                 460 ggc tca ctg cca atc gca ctg gat gaa gtg att act gat ggt cac aaa     1740
Gly Ser Leu Pro Ile Ala Leu Asp Glu Val Ile Thr Asp Gly His Lys
465                 470                 475                 480 cgc gcg ctg att gtg act gac cgc ttc ctg ttc aac aac ggt tac gcg     1788
Arg Ala Leu Ile Val Thr Asp Arg Phe Leu Phe Asn Asn Gly Tyr Ala
                485                 490                 495 gac cag atc act tcc gta ctg aaa gcg gct ggc gta gaa acc gaa gtg     1836
Asp Gln Ile Thr Ser Val Leu Lys Ala Ala Gly Val Glu Thr Glu Val
            500                 505                 510 ttc ttt gaa gtt gaa gct gac cca acg ctg act atc gtg cgt aaa ggc     1884
Phe Phe Glu Val Glu Ala Asp Pro Thr Leu Thr Ile Val Arg Lys Gly
        515                 520                 525 gcg gat ctg gcc aac tcc ttc aaa cca gac gta atc atc gcc ctg ggc     1932
Ala Asp Leu Ala Asn Ser Phe Lys Pro Asp Val Ile Ile Ala Leu Gly
530                 535                 540 ggc ggt tcc ccg atg gat gcg gca aaa atc atg tgg gtc atg tac gag     1980
Gly Gly Ser Pro Met Asp Ala Ala Lys Ile Met Trp Val Met Tyr Glu
545                 550                 555                 560 cac ccg gaa acc cac ttc gaa gaa ctg gcg ctg cgc ttt atg gat atc     2028
His Pro Glu Thr His Phe Glu Glu Leu Ala Leu Arg Phe Met Asp Ile
                565                 570                 575 cgt aaa cgt atc tac aag ttc ccg aaa atg ggc gtc aaa gcc aag atg     2076
Arg Lys Arg Ile Tyr Lys Phe Pro Lys Met Gly Val Lys Ala Lys Met
            580                 585                 590 gtt gcc att acc acc acc tcc ggt acc ggt tct gaa gtt acc ccg ttc     2124
Val Ala Ile Thr Thr Thr Ser Gly Thr Gly Ser Glu Val Thr Pro Phe
        595                 600                 605 gcc gta gta acc gac gat gca act gga cag aaa tat ccg ctg gct gac     2172
Ala Val Val Thr Asp Asp Ala Thr Gly Gln Lys Tyr Pro Leu Ala Asp
610                 615                 620 tac gct ctg act ccg gat atg gcg att gtc gat gcc aac ctg gtc atg     2220
Tyr Ala Leu Thr Pro Asp Met Ala Ile Val Asp Ala Asn Leu Val Met
625                 630                 635                 640 gat atg ccg aag tct ctc tgt gcc ttc ggt ggt ctg gat gcc gtg act     2268
Asp Met Pro Lys Ser Leu Cys Ala Phe Gly Gly Leu Asp Ala Val Thr
                645                 650                 655 cac gct ctg gaa gct tac gtc tcc gta ctg gct tct gag ttc tcc gat     2316
His Ala Leu Glu Ala Tyr Val Ser Val Leu Ala Ser Glu Phe Ser Asp
            660                 665                 670 ggt cag gct ctg cag gcg ctg aaa ctg ctg aaa gag tat ctg ccg gcc     2364
Gly Gln Ala Leu Gln Ala Leu Lys Leu Leu Lys Glu Tyr Leu Pro Ala
        675                 680                 685 tct tac cat gaa ggt tct aag aac ccg gta gcc cgc gaa cgt gtg cac     2412
Ser Tyr His Glu Gly Ser Lys Asn Pro Val Ala Arg Glu Arg Val His
690                 695                 700 agc gcc gcc act atc gcc ggt atc gcg ttt gct aac gcc ttc ctc ggc     2460
Ser Ala Ala Thr Ile Ala Gly Ile Ala Phe Ala Asn Ala Phe Leu Gly
705                 710                 715                 720 gtg tgc cac tca atg gcg cac aaa ctg ggc tcg cag ttc cac att cct     2508
Val Cys His Ser Met Ala His Lys Leu Gly Ser Gln Phe His Ile Pro
                725                 730                 735 cac ggt ctg gca aac gcc ctg ctg atc agc aac gtt atc cgc tat aac     2556
```

```
                His Gly Leu Ala Asn Ala Leu Leu Ile Ser Asn Val Ile Arg Tyr Asn
                                740                 745                 750 gcg aat gac aac ccg acc aag cag acc gca ttc agc cag tat gac cgt      2604
Ala Asn Asp Asn Pro Thr Lys Gln Thr Ala Phe Ser Gln Tyr Asp Arg
            755                 760                 765 ccg cag gcg cgc cgt cgc tac gct gag atc gca gac cac ctg ggc ctg      2652
Pro Gln Ala Arg Arg Arg Tyr Ala Glu Ile Ala Asp His Leu Gly Leu
        770                 775                 780 agc gct ccg ggc gac cgc act gcg gcg aaa atc gag aaa ctg ctg gca      2700
Ser Ala Pro Gly Asp Arg Thr Ala Ala Lys Ile Glu Lys Leu Leu Ala
785                 790                 795                 800 tgg ctg gaa agc ctc aaa gct gaa ctg ggt att ccg aaa tct att cgc      2748
Trp Leu Glu Ser Leu Lys Ala Glu Leu Gly Ile Pro Lys Ser Ile Arg
                805                 810                 815 gaa gcc ggc gtt cag gaa gct gat ttc ctg gct cac gtt gat aag ctg      2796
Glu Ala Gly Val Gln Glu Ala Asp Phe Leu Ala His Val Asp Lys Leu
            820                 825                 830 tct gaa gac gcc ttc gat gac cag tgc acc ggc gct aac ccg cgc tac      2844
Ser Glu Asp Ala Phe Asp Asp Gln Cys Thr Gly Ala Asn Pro Arg Tyr
        835                 840                 845 ccg ctg atc gcc gag ctg aaa cag att ctg ctg gat acc tac tac ggt      2892
Pro Leu Ile Ala Glu Leu Lys Gln Ile Leu Leu Asp Thr Tyr Tyr Gly
850                 855                 860 cgt gac ttt gta gaa ggt gaa gcg gcg gct gtg aaa aaa gaa gcg gct      2940
Arg Asp Phe Val Glu Gly Glu Ala Ala Ala Val Lys Lys Glu Ala Ala
865                 870                 875                 880 ccg gcc aaa gct gag aaa aaa gac gaa aaa atc cgc tta att cgc aga      2988
Pro Ala Lys Ala Glu Lys Lys Asp Glu Lys Ile Arg Leu Ile Arg Arg
                885                 890                 895 att gaa atg aac gaa gcc cca tct att gat ggg gct ttt ttt ata ttc      3036
Ile Glu Met Asn Glu Ala Pro Ser Ile Asp Gly Ala Phe Phe Ile Phe
            900                 905                 910 gta ctt tat tag agtttcatcc aggagtattg tatgcaatga atctggtgaa           3088
Val Leu Tyr
        915 gtcggaataa aggaaccgat tccataaaag acaacaggcg ccatttagac gcctgaaggt     3148 aatgaaatta cagcattatt cgccgtggcg cagcttactt tgcacctgag ttaatgaacc     3208 ggtgcttaac gcctctttat aatgcttacg gcatacggaa acgtaccgct cattaccgcc     3268 aatcactacc tgttctcctt cattgtatgg ccgcccttcc tgatcaaggc gtaacaccat     3328 gcttgcctta cggccacaga                                                 3348

<210> SEQ ID NO 22
<211> LENGTH: 3420
<212> TYPE: DNA
<213> ORGANISM: Brevibacterium fluvum
<220> FEATURE:
<221> NAME/KEY: CDS
<222> LOCATION: (1)..(3420)

<400> SEQUENCE: 22 atg tcg act cac aca tct tca acg ctt cca gca ttc aaa aag atc ttg       48
Met Ser Thr His Thr Ser Ser Thr Leu Pro Ala Phe Lys Lys Ile Leu
1               5                   10                  15 gta gca aac cgc ggc gaa atc gcg gtc cgt gct ttc cgt gca gca ctc       96
Val Ala Asn Arg Gly Glu Ile Ala Val Arg Ala Phe Arg Ala Ala Leu
                20                  25                  30 gaa acc ggt gca gcc acg gta gct att tac ccc cgt gaa gat cgg gga      144
Glu Thr Gly Ala Ala Thr Val Ala Ile Tyr Pro Arg Glu Asp Arg Gly
            35                  40                  45
```

| | | | | | | | | | | | | | | | | |
|---|---|---|---|---|---|---|---|---|---|---|---|---|---|---|---|---|
| tca | ttc | cac | cgc | tct | ttt | gct | tct | gaa | gct | gtc | cgc | att | ggt | act | gaa | 192 |
| Ser | Phe | His | Arg | Ser | Phe | Ala | Ser | Glu | Ala | Val | Arg | Ile | Gly | Thr | Glu | |
| 50 | | | | 55 | | | | | 60 | | | | | | | |
| ggc | tca | cca | gtc | aag | gcg | tac | ctg | gac | atc | gat | gaa | att | atc | ggt | gca | 240 |
| Gly | Ser | Pro | Val | Lys | Ala | Tyr | Leu | Asp | Ile | Asp | Glu | Ile | Ile | Gly | Ala | |
| 65 | | | | 70 | | | | 75 | | | | | | 80 | | |
| gct | aaa | aaa | gtt | aaa | gca | gat | gct | att | tac | ccg | gga | tat | ggc | ttc | ctg | 288 |
| Ala | Lys | Lys | Val | Lys | Ala | Asp | Ala | Ile | Tyr | Pro | Gly | Tyr | Gly | Phe | Leu | |
| | | | | 85 | | | | | 90 | | | | | 95 | | |
| tct | gaa | aat | gcc | cag | ctt | gcc | cgc | gag | tgc | gcg | gaa | aac | ggc | att | act | 336 |
| Ser | Glu | Asn | Ala | Gln | Leu | Ala | Arg | Glu | Cys | Ala | Glu | Asn | Gly | Ile | Thr | |
| | | | 100 | | | | | 105 | | | | | 110 | | | |
| ttt | att | ggc | cca | acc | cca | gag | gtt | ctt | gat | ctc | acc | ggt | gat | aag | tct | 384 |
| Phe | Ile | Gly | Pro | Thr | Pro | Glu | Val | Leu | Asp | Leu | Thr | Gly | Asp | Lys | Ser | |
| | | 115 | | | | | 120 | | | | | 125 | | | | |
| cgt | gcg | gta | acc | gcc | gcg | aag | aag | gct | ggt | ctg | cca | gtt | ttg | gcg | gaa | 432 |
| Arg | Ala | Val | Thr | Ala | Ala | Lys | Lys | Ala | Gly | Leu | Pro | Val | Leu | Ala | Glu | |
| 130 | | | | | 135 | | | | | 140 | | | | | | |
| tcc | acc | ccg | agc | aaa | aac | atc | gat | gac | atc | gtt | aaa | agc | gct | gaa | ggc | 480 |
| Ser | Thr | Pro | Ser | Lys | Asn | Ile | Asp | Asp | Ile | Val | Lys | Ser | Ala | Glu | Gly | |
| 145 | | | | 150 | | | | | 155 | | | | | 160 | | |
| cag | act | tac | ccc | atc | ttt | gta | aag | gca | gtt | gcc | ggt | ggt | ggc | gga | cgc | 528 |
| Gln | Thr | Tyr | Pro | Ile | Phe | Val | Lys | Ala | Val | Ala | Gly | Gly | Gly | Gly | Arg | |
| | | | | 165 | | | | | 170 | | | | | 175 | | |
| ggt | atg | cgc | ttt | gtt | tct | tca | cct | gat | gag | ctt | cgc | aaa | ttg | gca | aca | 576 |
| Gly | Met | Arg | Phe | Val | Ser | Ser | Pro | Asp | Glu | Leu | Arg | Lys | Leu | Ala | Thr | |
| | | | 180 | | | | | 185 | | | | | 190 | | | |
| gaa | gca | tct | cgt | gaa | gct | gaa | gcg | gca | ttc | ggc | gac | ggt | tcg | gta | tat | 624 |
| Glu | Ala | Ser | Arg | Glu | Ala | Glu | Ala | Ala | Phe | Gly | Asp | Gly | Ser | Val | Tyr | |
| | | 195 | | | | | 200 | | | | | 205 | | | | |
| gtc | gag | cgt | gct | gtg | att | aac | ccc | cag | cac | att | gaa | gtg | cag | atc | ctt | 672 |
| Val | Glu | Arg | Ala | Val | Ile | Asn | Pro | Gln | His | Ile | Glu | Val | Gln | Ile | Leu | |
| 210 | | | | | 215 | | | | | 220 | | | | | | |
| ggc | gat | cgc | act | gga | gaa | gtt | gta | cac | ctt | tat | gaa | cgt | gac | tgc | tca | 720 |
| Gly | Asp | Arg | Thr | Gly | Glu | Val | Val | His | Leu | Tyr | Glu | Arg | Asp | Cys | Ser | |
| 225 | | | | 230 | | | | | 235 | | | | | 240 | | |
| ctg | cag | cgt | cgt | cac | caa | aaa | gtt | gtc | gaa | att | gcg | cca | gca | cag | cat | 768 |
| Leu | Gln | Arg | Arg | His | Gln | Lys | Val | Val | Glu | Ile | Ala | Pro | Ala | Gln | His | |
| | | | | 245 | | | | | 250 | | | | | 255 | | |
| ttg | gat | cca | gaa | ctg | cgt | gat | cgc | att | tgt | gcg | gat | gca | gta | aag | ttc | 816 |
| Leu | Asp | Pro | Glu | Leu | Arg | Asp | Arg | Ile | Cys | Ala | Asp | Ala | Val | Lys | Phe | |
| | | | 260 | | | | | 265 | | | | | 270 | | | |
| tgc | cgc | tcc | att | ggt | tac | cag | ggc | gcg | gga | act | gtg | gaa | ttc | ttg | gtc | 864 |
| Cys | Arg | Ser | Ile | Gly | Tyr | Gln | Gly | Ala | Gly | Thr | Val | Glu | Phe | Leu | Val | |
| | | 275 | | | | | 280 | | | | | 285 | | | | |
| gat | gaa | aag | ggc | aac | cac | gtt | ttc | atc | gaa | atg | aac | cca | cgt | atc | cag | 912 |
| Asp | Glu | Lys | Gly | Asn | His | Val | Phe | Ile | Glu | Met | Asn | Pro | Arg | Ile | Gln | |
| 290 | | | | | 295 | | | | | 300 | | | | | | |
| gtt | gag | cac | acc | gtg | act | gaa | gaa | gtc | acc | gag | gtg | gac | ctg | gtg | aag | 960 |
| Val | Glu | His | Thr | Val | Thr | Glu | Glu | Val | Thr | Glu | Val | Asp | Leu | Val | Lys | |
| 305 | | | | 310 | | | | | 315 | | | | | 320 | | |
| gcg | cag | atg | cgc | ttg | gct | gct | ggt | gca | acc | ttg | aag | gaa | ttg | ggt | ctg | 1008 |
| Ala | Gln | Met | Arg | Leu | Ala | Ala | Gly | Ala | Thr | Leu | Lys | Glu | Leu | Gly | Leu | |
| | | | | 325 | | | | | 330 | | | | | 335 | | |
| acc | caa | gat | aag | atc | aag | acc | cac | ggt | gcg | gca | ctg | cag | tgc | cgc | atc | 1056 |
| Thr | Gln | Asp | Lys | Ile | Lys | Thr | His | Gly | Ala | Ala | Leu | Gln | Cys | Arg | Ile | |
| | | | 340 | | | | | 345 | | | | | 350 | | | |
| acc | acg | gaa | gat | cca | aac | aac | ggc | ttc | cgc | cca | gat | acc | gga | act | atc | 1104 |
| Thr | Thr | Glu | Asp | Pro | Asn | Asn | Gly | Phe | Arg | Pro | Asp | Thr | Gly | Thr | Ile | |
| | | 355 | | | | | 360 | | | | | 365 | | | | |

```
acc gcg tac cgc tca cca ggc gga gct ggc gtt cgt ctt gac ggt gca    1152
Thr Ala Tyr Arg Ser Pro Gly Gly Ala Gly Val Arg Leu Asp Gly Ala
        370             375                 380 gct cag ctc ggt ggc gaa atc acc gca cac ttt gac tcc atg ctg gtg    1200
Ala Gln Leu Gly Gly Glu Ile Thr Ala His Phe Asp Ser Met Leu Val
385             390                 395                 400 aaa atg acc tgc cgt ggt tcc gat ttt gaa act gct gtt gct cgt gca    1248
Lys Met Thr Cys Arg Gly Ser Asp Phe Glu Thr Ala Val Ala Arg Ala
            405                 410                 415 cag cgc gcg ttg gct gag ttc acc gtg tct ggt gtt gca acc aac att    1296
Gln Arg Ala Leu Ala Glu Phe Thr Val Ser Gly Val Ala Thr Asn Ile
        420                 425                 430 ggt ttc ttg cgt gcg ttg ctg cgt gaa gag gac ttt act tcc aag cgc    1344
Gly Phe Leu Arg Ala Leu Leu Arg Glu Glu Asp Phe Thr Ser Lys Arg
            435                 440                 445 atc gcc acc gga ttt atc ggc gat cac cca cac ctc ctt cag gct cca    1392
Ile Ala Thr Gly Phe Ile Gly Asp His Pro His Leu Leu Gln Ala Pro
        450                 455                 460 cct gcg gat gat gag cag gga cgc atc ctg gat tac ttg gca gat gtc    1440
Pro Ala Asp Asp Glu Gln Gly Arg Ile Leu Asp Tyr Leu Ala Asp Val
465                 470                 475                 480 acc gtg aac aag cct cat ggt gtg cgt cca aag gat gtt gca gca cca    1488
Thr Val Asn Lys Pro His Gly Val Arg Pro Lys Asp Val Ala Ala Pro
            485                 490                 495 atc gat aag ctg ccc aac atc aag gat ctg cca ctg cca cgc ggt tcc    1536
Ile Asp Lys Leu Pro Asn Ile Lys Asp Leu Pro Leu Pro Arg Gly Ser
        500                 505                 510 cgt gac cgc ctg aag cag ctt gga cca gca gcg ttt gcc cgc gat ctc    1584
Arg Asp Arg Leu Lys Gln Leu Gly Pro Ala Ala Phe Ala Arg Asp Leu
            515                 520                 525 cgt gag cag gac gca ctg gca gtt act gat acc acc ttc cgc gat gca    1632
Arg Glu Gln Asp Ala Leu Ala Val Thr Asp Thr Thr Phe Arg Asp Ala
        530                 535                 540 cac cag tct ttg ctt gcg acc cga gtc cgc tca ttc gca ctg aag cct    1680
His Gln Ser Leu Leu Ala Thr Arg Val Arg Ser Phe Ala Leu Lys Pro
545                 550                 555                 560 gcg gca gag gcc gtc gca aag ctg act cct gag ctt ttg tcc gtg gag    1728
Ala Ala Glu Ala Val Ala Lys Leu Thr Pro Glu Leu Leu Ser Val Glu
            565                 570                 575 gcc tgg ggc ggt gcg acc tac gat gtg gcg atg cgt ttc ctc ttt gag    1776
Ala Trp Gly Gly Ala Thr Tyr Asp Val Ala Met Arg Phe Leu Phe Glu
        580                 585                 590 gat ccg tgg gac agg ctc gac gag ctg cgc gag gcg atg ccg aat gtg    1824
Asp Pro Trp Asp Arg Leu Asp Glu Leu Arg Glu Ala Met Pro Asn Val
            595                 600                 605 aac att cag atg ctg ctt cgc ggc cgc aac acc gtg gga tac acc cca    1872
Asn Ile Gln Met Leu Leu Arg Gly Arg Asn Thr Val Gly Tyr Thr Pro
        610                 615                 620 tac cca gac tcc gtc tgt cgc gcg ttt gtt aag gaa gct gcc acc tcc    1920
Tyr Pro Asp Ser Val Cys Arg Ala Phe Val Lys Glu Ala Ala Thr Ser
625                 630                 635                 640 ggc gtg gac atc ttc cgc atc ttc gac gcg ctt aac gac gtc tcc cag    1968
Gly Val Asp Ile Phe Arg Ile Phe Asp Ala Leu Asn Asp Val Ser Gln
            645                 650                 655 atg cgt cca gca atc gac gca gtc ctg gag acc aac acc gcg gtc gct    2016
Met Arg Pro Ala Ile Asp Ala Val Leu Glu Thr Asn Thr Ala Val Ala
        660                 665                 670 gaa gtg gct atg gct tat tct ggt gat ctt tcc gat ccg aat gaa aag    2064
Glu Val Ala Met Ala Tyr Ser Gly Asp Leu Ser Asp Pro Asn Glu Lys
            675                 680                 685
```

```
ctc tac acc ctg gat tac tac ctg aag atg gca gag gag atc gtc aag    2112
Leu Tyr Thr Leu Asp Tyr Tyr Leu Lys Met Ala Glu Glu Ile Val Lys
    690             695                 700 tct ggc gct cac att ctg gct att aag gat atg gct ggt ctg ctt cgc    2160
Ser Gly Ala His Ile Leu Ala Ile Lys Asp Met Ala Gly Leu Leu Arg
705             710                 715                 720 cca gct gca gcc acc aag ctg gtc acc gca ctg cgc cgt gaa ttt gat    2208
Pro Ala Ala Ala Thr Lys Leu Val Thr Ala Leu Arg Arg Glu Phe Asp
                725                 730                 735 ctg cca gtg cac gtg cac acc cac gac act gcg ggt ggc cag ctg gca    2256
Leu Pro Val His Val His Thr His Asp Thr Ala Gly Gly Gln Leu Ala
            740                 745                 750 acc tac ttt gct gca gct caa gct ggt gca gat gct gtt gac ggt gct    2304
Thr Tyr Phe Ala Ala Ala Gln Ala Gly Ala Asp Ala Val Asp Gly Ala
        755                 760                 765 tcc gca cca ctg tct ggc acc acc tcc cag cca tcc ctg tct gcc att    2352
Ser Ala Pro Leu Ser Gly Thr Thr Ser Gln Pro Ser Leu Ser Ala Ile
    770                 775                 780 gtt gct gca ttc gcg cac acc cgt cgc gat acc ggt ttg agc ctc gag    2400
Val Ala Ala Phe Ala His Thr Arg Arg Asp Thr Gly Leu Ser Leu Glu
785             790                 795                 800 gct gtt tct gac ctc gag cca tac tgg gaa gca gtg cgc gga ctg tac    2448
Ala Val Ser Asp Leu Glu Pro Tyr Trp Glu Ala Val Arg Gly Leu Tyr
                805                 810                 815 ctg cca ttt gag tct gga acc cca ggc cca acc ggt cgc gtc tac cgc    2496
Leu Pro Phe Glu Ser Gly Thr Pro Gly Pro Thr Gly Arg Val Tyr Arg
            820                 825                 830 cac gaa atc cca ggc gga cag ctg tcc aac ctg cgt gca cag gcc acc    2544
His Glu Ile Pro Gly Gly Gln Leu Ser Asn Leu Arg Ala Gln Ala Thr
        835                 840                 845 gca ctg ggc ctt gcg gat cgt ttc gaa ctc atc gaa gac aac tac gcg    2592
Ala Leu Gly Leu Ala Asp Arg Phe Glu Leu Ile Glu Asp Asn Tyr Ala
    850                 855                 860 gca gtt aat gag atg ctg gga cgc cca acc aag gtc acc cca tcc tcc    2640
Ala Val Asn Glu Met Leu Gly Arg Pro Thr Lys Val Thr Pro Ser Ser
865             870                 875                 880 aag gtt gtt ggc gac ctc gca ctc cac ctc gtt ggt gcg ggt gtg gat    2688
Lys Val Val Gly Asp Leu Ala Leu His Leu Val Gly Ala Gly Val Asp
                885                 890                 895 cca gca gac ttt gct gca gat cca caa aag tac gac atc cca gac tct    2736
Pro Ala Asp Phe Ala Ala Asp Pro Gln Lys Tyr Asp Ile Pro Asp Ser
            900                 905                 910 gtc atc gcg ttc ctg cgc ggc gag ctt ggt aac cct cca ggt ggc tgg    2784
Val Ile Ala Phe Leu Arg Gly Glu Leu Gly Asn Pro Pro Gly Gly Trp
        915                 920                 925 cca gag cca ctg cgc acc cgc gca ctg gaa ggc cgc tcc gaa ggc aag    2832
Pro Glu Pro Leu Arg Thr Arg Ala Leu Glu Gly Arg Ser Glu Gly Lys
    930                 935                 940 gca cct ctg acg gaa gtt cct gag gaa gag cag gcg cac ctc gac gct    2880
Ala Pro Leu Thr Glu Val Pro Glu Glu Glu Gln Ala His Leu Asp Ala
945             950                 955                 960 gat gat tcc aag gaa cgt cgc aac agc ctc aac cgc ctg ctg ttc ccg    2928
Asp Asp Ser Lys Glu Arg Arg Asn Ser Leu Asn Arg Leu Leu Phe Pro
                965                 970                 975 aag cca acc gaa gag ttc ctc gag cac cgt cgc cgc ttc ggc aac acc    2976
Lys Pro Thr Glu Glu Phe Leu Glu His Arg Arg Arg Phe Gly Asn Thr
            980                 985                 990 tct gcg ctg gat gat cgt gaa ttc ttc tac ggc ctg gtc gaa ggc cgc    3024
Ser Ala Leu Asp Asp Arg Glu Phe Phe Tyr Gly Leu Val Glu Gly Arg
        995                 1000                1005
```

```
gag act ttg atc cgc ctg cca gat gtg cgc acc cca ctg ctt gtt      3069
Glu Thr Leu Ile Arg Leu Pro Asp Val Arg Thr Pro Leu Leu Val
    1010                1015                1020 cgc ctg gat gcg atc tcc gag cca gac gat aag ggt atg cgc aat      3114
Arg Leu Asp Ala Ile Ser Glu Pro Asp Asp Lys Gly Met Arg Asn
1025                1030                1035 gtt gtg gcc aac gtc aac ggc cag atc cgc cca atg cgt gtg cgt      3159
Val Val Ala Asn Val Asn Gly Gln Ile Arg Pro Met Arg Val Arg
        1040                1045                1050 gac cgc tcc gtt gag tct gtc acc gca acc gca gaa aag gca gat      3204
Asp Arg Ser Val Glu Ser Val Thr Ala Thr Ala Glu Lys Ala Asp
            1055                1060                1065 tcc tcc aac aag ggc cat gtt gct gca cca ttc gct ggt gtt gtc      3249
Ser Ser Asn Lys Gly His Val Ala Ala Pro Phe Ala Gly Val Val
1070                1075                1080 act gtg act gtt gct gaa ggt gat gag gtc aag gct gga gat gca      3294
Thr Val Thr Val Ala Glu Gly Asp Glu Val Lys Ala Gly Asp Ala
        1085                1090                1095 gtc gca atc atc gag gct atg aag atg gaa gca aca atc act gct      3339
Val Ala Ile Ile Glu Ala Met Lys Met Glu Ala Thr Ile Thr Ala
            1100                1105                1110 tct gtt gac ggc aaa atc gat cgc gtt gtg gtt cct gct gca acg      3384
Ser Val Asp Gly Lys Ile Asp Arg Val Val Val Pro Ala Ala Thr
1115                1120                1125 aag gtg gaa ggt ggc gac ttg atc gtc gtc gtt tcc                  3420
Lys Val Glu Gly Gly Asp Leu Ile Val Val Val Ser
        1130                1135                1140

<210> SEQ ID NO 23
<211> LENGTH: 1140
<212> TYPE: PRT
<213> ORGANISM: Brevibacterium fluvum

<400> SEQUENCE: 23

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Asp Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ser Ser Pro Asp Glu Leu Arg Lys Leu Ala Thr
            180                 185                 190
```

-continued

```
Glu Ala Ser Arg Glu Ala Ala Phe Gly Asp Gly Ser Val Tyr
        195                 200                 205
Val Glu Arg Ala Val Ile Asn Pro Gln His Ile Glu Val Gln Ile Leu
210                 215                 220
Gly Asp Arg Thr Gly Glu Val Val His Leu Tyr Glu Arg Asp Cys Ser
225                 230                 235                 240
Leu Gln Arg Arg His Gln Lys Val Val Glu Ile Ala Pro Ala Gln His
                245                 250                 255
Leu Asp Pro Glu Leu Arg Asp Arg Ile Cys Ala Asp Ala Val Lys Phe
                260                 265                 270
Cys Arg Ser Ile Gly Tyr Gln Gly Ala Gly Thr Val Glu Phe Leu Val
                275                 280                 285
Asp Glu Lys Gly Asn His Val Phe Ile Glu Met Asn Pro Arg Ile Gln
            290                 295                 300
Val Glu His Thr Val Thr Glu Glu Val Thr Glu Val Asp Leu Val Lys
305                 310                 315                 320
Ala Gln Met Arg Leu Ala Ala Gly Ala Thr Leu Lys Glu Leu Gly Leu
                325                 330                 335
Thr Gln Asp Lys Ile Lys Thr His Gly Ala Ala Leu Gln Cys Arg Ile
                340                 345                 350
Thr Thr Glu Asp Pro Asn Asn Gly Phe Arg Pro Asp Thr Gly Thr Ile
            355                 360                 365
Thr Ala Tyr Arg Ser Pro Gly Gly Ala Gly Val Arg Leu Asp Gly Ala
370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
                420                 425                 430
Gly Phe Leu Arg Ala Leu Leu Arg Glu Glu Asp Phe Thr Ser Lys Arg
            435                 440                 445
Ile Ala Thr Gly Phe Ile Gly Asp His Pro His Leu Leu Gln Ala Pro
450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
                500                 505                 510
Arg Asp Arg Leu Lys Gln Leu Gly Pro Ala Ala Phe Ala Arg Asp Leu
            515                 520                 525
Arg Glu Gln Asp Ala Leu Ala Val Thr Asp Thr Thr Phe Arg Asp Ala
530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
                580                 585                 590
Asp Pro Trp Asp Arg Leu Asp Glu Leu Arg Glu Ala Met Pro Asn Val
            595                 600                 605
Asn Ile Gln Met Leu Leu Arg Gly Arg Asn Thr Val Gly Tyr Thr Pro
610                 615                 620
```

```
Tyr Pro Asp Ser Val Cys Arg Ala Phe Val Lys Glu Ala Ala Thr Ser
625                 630                 635                 640

Gly Val Asp Ile Phe Arg Ile Phe Asp Ala Leu Asn Asp Val Ser Gln
            645                 650                 655

Met Arg Pro Ala Ile Asp Ala Val Leu Glu Thr Asn Thr Ala Val Ala
        660                 665                 670

Glu Val Ala Met Ala Tyr Ser Gly Asp Leu Ser Asp Pro Asn Glu Lys
    675                 680                 685

Leu Tyr Thr Leu Asp Tyr Tyr Leu Lys Met Ala Glu Glu Ile Val Lys
690                 695                 700

Ser Gly Ala His Ile Leu Ala Ile Lys Asp Met Ala Gly Leu Leu Arg
705                 710                 715                 720

Pro Ala Ala Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
            755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
            965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
```

-continued

```
                    1040                1045                1050

Asp Arg  Ser Val Glu Ser Val  Thr Ala Thr Ala Glu  Lys Ala Asp
        1055                1060                1065

Ser Ser  Asn Lys Gly His Val  Ala Ala Pro Phe Ala  Gly Val Val
        1070                1075                1080

Thr Val  Thr Val Ala Glu Gly  Asp Glu Val Lys Ala  Gly Asp Ala
        1085                1090                1095

Val Ala  Ile Ile Glu Ala Met  Lys Met Glu Ala Thr  Ile Thr Ala
        1100                1105                1110

Ser Val  Asp Gly Lys Ile Asp  Arg Val Val Val Pro  Ala Ala Thr
        1115                1120                1125

Lys Val  Glu Gly Gly Asp Leu  Ile Val Val Val Ser
        1130                1135                1140

<210> SEQ ID NO 24
<211> LENGTH: 545
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(24)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(45)
<223> OTHER INFORMATION: Xaa can be any naturally occurring amino acid
<220> FEATURE:
<221> NAME/KEY: misc_feature
<222> LOCATION: (47)..(51)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
```

```
<221> NAME/KEY: misc_feature
<222> LOCATION: (75)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (84)..(90)
<223> OTHER INFORMATION: Xaa can be any naturally occurring amino acid
<220> FEATURE:
<221> NAME/KEY: misc_feature
<222> LOCATION: (94)..(100)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (105)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: misc_feature
<222> LOCATION: (120)..(123)
<223> OTHER INFORMATION: Xaa can be any naturally occurring amino acid
<220> FEATURE:
<221> NAME/KEY: misc_feature
<222> LOCATION: (127)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (136)..(138)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(158)
<223> OTHER INFORMATION: Xaa can be any naturally occurring amino acid
<220> FEATURE:
<221> NAME/KEY: misc_feature
<222> LOCATION: (160)..(161)
<223> OTHER INFORMATION: Xaa can be any naturally occurring amino acid
<220> FEATURE:
<221> NAME/KEY: misc_feature
<222> LOCATION: (163)..(164)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (171)..(172)
<223> OTHER INFORMATION: Xaa can be any naturally occurring amino acid
<220> FEATURE:
```

```
<221> NAME/KEY: misc_feature
<222> LOCATION: (174)..(179)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (188)..(191)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (196)..(198)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (202)..(203)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (227)..(229)
<223> OTHER INFORMATION: Xaa can be any naturally occurring amino acid
<220> FEATURE:
<221> NAME/KEY: misc_feature
<222> LOCATION: (236)..(239)
<223> OTHER INFORMATION: Xaa can be any naturally occurring amino acid
<220> FEATURE:
<221> NAME/KEY: misc_feature
<222> LOCATION: (241)..(243)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (275)..(276)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
```

-continued

```
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (314)..(318)
<223> OTHER INFORMATION: Xaa can be any naturally occurring amino acid
<220> FEATURE:
<221> NAME/KEY: misc_feature
<222> LOCATION: (320)..(321)
<223> OTHER INFORMATION: Xaa can be any naturally occurring amino acid
<220> FEATURE:
<221> NAME/KEY: misc_feature
<222> LOCATION: (323)..(324)
<223> OTHER INFORMATION: Xaa can be any naturally occurring amino acid
<220> FEATURE:
<221> NAME/KEY: misc_feature
<222> LOCATION: (326)..(328)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (342)..(344)
<223> OTHER INFORMATION: Xaa can be any naturally occurring amino acid
<220> FEATURE:
<221> NAME/KEY: misc_feature
<222> LOCATION: (346)..(352)
<223> OTHER INFORMATION: Xaa can be any naturally occurring amino acid
<220> FEATURE:
<221> NAME/KEY: misc_feature
<222> LOCATION: (354)..(357)
<223> OTHER INFORMATION: Xaa can be any naturally occurring amino acid
<220> FEATURE:
<221> NAME/KEY: misc_feature
<222> LOCATION: (359)..(360)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (380)..(381)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (386)..(386)
<223> OTHER INFORMATION: Xaa can be any naturally occurring amino acid
<220> FEATURE:
```

```
<221> NAME/KEY: misc_feature
<222> LOCATION: (402)..(402)
<223> OTHER INFORMATION: Xaa can be any naturally occurring amino acid
<220> FEATURE:
<221> NAME/KEY: misc_feature
<222> LOCATION: (415)..(415)
<223> OTHER INFORMATION: Xaa can be any naturally occurring amino acid
<220> FEATURE:
<221> NAME/KEY: misc_feature
<222> LOCATION: (419)..(419)
<223> OTHER INFORMATION: Xaa can be any naturally occurring amino acid
<220> FEATURE:
<221> NAME/KEY: misc_feature
<222> LOCATION: (423)..(424)
<223> OTHER INFORMATION: Xaa can be any naturally occurring amino acid
<220> FEATURE:
<221> NAME/KEY: misc_feature
<222> LOCATION: (427)..(428)
<223> OTHER INFORMATION: Xaa can be any naturally occurring amino acid
<220> FEATURE:
<221> NAME/KEY: misc_feature
<222> LOCATION: (431)..(432)
<223> OTHER INFORMATION: Xaa can be any naturally occurring amino acid
<220> FEATURE:
<221> NAME/KEY: misc_feature
<222> LOCATION: (434)..(436)
<223> OTHER INFORMATION: Xaa can be any naturally occurring amino acid
<220> FEATURE:
<221> NAME/KEY: misc_feature
<222> LOCATION: (438)..(439)
<223> OTHER INFORMATION: Xaa can be any naturally occurring amino acid
<220> FEATURE:
<221> NAME/KEY: misc_feature
<222> LOCATION: (450)..(450)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (467)..(468)
<223> OTHER INFORMATION: Xaa can be any naturally occurring amino acid
<220> FEATURE:
<221> NAME/KEY: misc_feature
<222> LOCATION: (470)..(470)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (475)..(479)
<223> OTHER INFORMATION: Xaa can be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (483)..(486)
<223> OTHER INFORMATION: Xaa can be any naturally occurring amino acid
<220> FEATURE:
<221> NAME/KEY: misc_feature
<222> LOCATION: (488)..(489)
<223> OTHER INFORMATION: Xaa can be any naturally occurring amino acid
<220> FEATURE:
<221> NAME/KEY: misc_feature
<222> LOCATION: (491)..(491)
<223> OTHER INFORMATION: Xaa can be any naturally occurring amino acid
<220> FEATURE:
<221> NAME/KEY: misc_feature
<222> LOCATION: (494)..(496)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid
<220> FEATURE:
```

```
<221> NAME/KEY: misc_feature
<222> LOCATION: (505)..(509)
<223> OTHER INFORMATION: Xaa can be any naturally occurring amino acid
<220> FEATURE:
<221> NAME/KEY: misc_feature
<222> LOCATION: (511)..(512)
<223> OTHER INFORMATION: Xaa can be any naturally occurring amino acid
<220> FEATURE:
<221> NAME/KEY: misc_feature
<222> LOCATION: (515)..(515)
<223> OTHER INFORMATION: Xaa can be any naturally occurring amino acid
<220> FEATURE:
<221> NAME/KEY: misc_feature
<222> LOCATION: (519)..(519)
<223> OTHER INFORMATION: Xaa can be any naturally occurring amino acid
<220> FEATURE:
<221> NAME/KEY: misc_feature
<222> LOCATION: (522)..(523)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (529)..(537)
<223> OTHER INFORMATION: Xaa can be any naturally occurring amino acid
<220> FEATURE:
<221> NAME/KEY: misc_feature
<222> LOCATION: (539)..(540)
<223> OTHER INFORMATION: Xaa can be any naturally occurring amino acid
<220> FEATURE:
<221> NAME/KEY: misc_feature
<222> LOCATION: (544)..(545)
<223> OTHER INFORMATION: Xaa can be any naturally occurring amino acid

<400> SEQUENCE: 24

Xaa Xaa Xaa Xaa Xaa Xaa Xaa Xaa Xaa Xaa Leu Xaa Xaa Xaa Gly Xaa
1               5                   10                  15

Xaa Xaa Xaa Xaa Xaa Xaa Xaa Xaa Asn Pro Ser Tyr Xaa Xaa Leu Glu
                20                  25                  30

Xaa Glu Glu Thr Xaa Xaa Xaa Leu Xaa Gly Xaa Xaa Xaa Gly Xaa Xaa
            35                  40                  45

Xaa Xaa Xaa Gly Ala Xaa Xaa Val Xaa Thr Gly Ile Phe Thr Gly Arg
    50                  55                  60

Ser Pro Lys Asp Lys Xaa Ile Val Xaa Asp Xaa Xaa Xaa Xaa Asp Thr
65              70                  75                  80

Xaa Trp Trp Xaa Xaa Xaa Xaa Xaa Xaa Asn Asp Asn Xaa Xaa Xaa Xaa
                85                  90                  95

Xaa Xaa Xaa Xaa Trp Xaa Xaa Leu Xaa Xaa Xaa Xaa Xaa Xaa Xaa Leu
            100                 105                 110

Ser Xaa Lys Xaa Xaa Xaa Val Xaa Xaa Xaa Xaa Cys Gly Ala Xaa Xaa
    115                 120                 125

Xaa Xaa Arg Xaa Xaa Val Arg Xaa Xaa Xaa Glu Val Ala Trp Gln Ala
130                 135                 140

His Phe Val Xaa Asn Met Phe Ile Xaa Pro Xaa Xaa Xaa Xaa Leu Xaa
145                 150                 155                 160

Xaa Phe Xaa Xaa Asp Phe Xaa Val Xaa Asn Xaa Xaa Lys Xaa Xaa Xaa
                165                 170                 175

Xaa Xaa Xaa Lys Glu Xaa Gly Leu Xaa Ser Glu Xaa Xaa Xaa Xaa Phe
            180                 185                 190

Asn Xaa Thr Xaa Xaa Xaa Gln Xaa Ile Xaa Xaa Thr Trp Tyr Gly Gly
        195                 200                 205

Glu Met Lys Lys Gly Met Phe Xaa Met Met Asn Tyr Xaa Leu Pro Leu
210                 215                 220
```

-continued

```
Xaa Gly Xaa Xaa Xaa Met His Cys Ser Ala Asn Xaa Xaa Xaa Gly
225                 230                 235                 240

Xaa Xaa Xaa Ala Xaa Phe Phe Gly Leu Ser Gly Thr Gly Lys Thr Thr
            245                 250                 255

Leu Ser Thr Asp Pro Lys Arg Xaa Leu Ile Gly Asp Asp Glu His Gly
        260                 265                 270

Trp Asp Xaa Xaa Gly Xaa Phe Asn Xaa Glu Gly Gly Cys Tyr Ala Lys
        275                 280                 285

Xaa Ile Xaa Leu Xaa Xaa Glu Xaa Glu Pro Asp Ile Tyr Xaa Ala Ile
    290                 295                 300

Xaa Arg Xaa Ala Leu Leu Glu Asn Val Xaa Xaa Xaa Xaa Gly Xaa
305                 310                 315                 320

Xaa Asp Xaa Xaa Asp Xaa Xaa Xaa Thr Glu Asn Thr Arg Val Ser Tyr
            325                 330                 335

Pro Ile Xaa His Ile Xaa Xaa Xaa Val Xaa Xaa Xaa Xaa Xaa Xaa
            340                 345                 350

Ser Xaa Xaa Xaa Xaa Ala Xaa Xaa Val Ile Phe Leu Xaa Ala Asp Ala
    355                 360                 365

Phe Gly Val Leu Pro Pro Val Ser Xaa Leu Thr Xaa Xaa Gln Thr Xaa
370                 375                 380

Tyr Xaa Phe Leu Ser Gly Phe Thr Ala Lys Leu Ala Gly Thr Glu Arg
385                 390                 395                 400

Gly Xaa Thr Glu Pro Thr Pro Thr Phe Ser Ala Cys Phe Gly Xaa Ala
        405                 410                 415

Phe Leu Xaa Leu His Pro Xaa Xaa Tyr Ala Xaa Xaa Leu Val Xaa Xaa
            420                 425                 430

Met Xaa Xaa Xaa Gly Xaa Xaa Ala Tyr Leu Val Asn Thr Gly Trp Asn
        435                 440                 445

Gly Xaa Gly Lys Arg Ile Ser Ile Lys Asp Thr Arg Xaa Ile Ile Asp
    450                 455                 460

Ala Ile Xaa Xaa Gly Xaa Ile Xaa Lys Ala Xaa Xaa Xaa Xaa Pro
465                 470                 475                 480

Xaa Phe Xaa Xaa Xaa Xaa Pro Xaa Xaa Leu Xaa Gly Val Xaa Xaa Xaa
            485                 490                 495

Ile Leu Asp Pro Xaa Asp Thr Tyr Xaa Xaa Xaa Xaa Trp Xaa Xaa
        500                 505                 510

Lys Ala Xaa Asp Leu Ala Xaa Arg Phe Xaa Xaa Asn Phe Xaa Lys Tyr
        515                 520                 525

Xaa Xaa Xaa Xaa Xaa Xaa Xaa Leu Xaa Xaa Ala Gly Pro Xaa
530                 535                 540

Xaa
545
```

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
tagcgagatc tctgatgtcc ggcggtgctt ttg            33

<210> SEQ ID NO 26
<211> LENGTH: 32
<212> TYPE: DNA
<213> ORGANISM: Artificial Sequence

```
<220> FEATURE:
<223> OTHER INFORMATION: primer

<400> SEQUENCE: 26
aaaaagagct cttacgcccc gccctgccac tc                              32

<210> SEQ ID NO 27
<211> LENGTH: 34
<212> TYPE: DNA
<213> ORGANISM: Artificial Sequence
<220> FEATURE:
<223> OTHER INFORMATION: primer

<400> SEQUENCE: 27
caggatctag aaggagacat gaacgatgaa catc                            34

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
gataaggatc cgaaataaaa gaaaatgcca atagga                          36

<210> SEQ ID NO 29
<211> LENGTH: 31
<212> TYPE: DNA
<213> ORGANISM: Artificial Sequence
<220> FEATURE:
<223> OTHER INFORMATION: primer

<400> SEQUENCE: 29
cctttgagct cgcgggcagt gagcgcaacg c                               31

<210> SEQ ID NO 30
<211> LENGTH: 48
<212> TYPE: DNA
<213> ORGANISM: Artificial Sequence
<220> FEATURE:
<223> OTHER INFORMATION: primer

<400> SEQUENCE: 30
ctagagcggc cgccgatcgg gatcctcctg tgtgaaattg ttatccgc              48

<210> SEQ ID NO 31
<211> LENGTH: 42
<212> TYPE: DNA
<213> ORGANISM: Artificial Sequence
<220> FEATURE:
<223> OTHER INFORMATION: primer

<400> SEQUENCE: 31
ctctacgatc gaggaggtta taaaaaatgg atattaatac tg                   42

<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
tcaaagcggc cgcttcttcg tctgtttcta ctggta                          36
```

```
<210> SEQ ID NO 33
<211> LENGTH: 31
<212> TYPE: DNA
<213> ORGANISM: Artificial Sequence
<220> FEATURE:
<223> OTHER INFORMATION: primer

<400> SEQUENCE: 33
cctttggtac cgcgggcagt gagcgcaacg c                              31

<210> SEQ ID NO 34
<211> LENGTH: 34
<212> TYPE: DNA
<213> ORGANISM: Artificial Sequence
<220> FEATURE:
<223> OTHER INFORMATION: primer

<400> SEQUENCE: 34
aacaggaatt ctttgcctgg cggcagtagc gcgg                           34

<210> SEQ ID NO 35
<211> LENGTH: 40
<212> TYPE: DNA
<213> ORGANISM: Artificial Sequence
<220> FEATURE:
<223> OTHER INFORMATION: primer P1

<400> SEQUENCE: 35
ctagtaagat cttgaagcct gcttttttat actaagttgg                     40

<210> SEQ ID NO 36
<211> LENGTH: 41
<212> TYPE: DNA
<213> ORGANISM: Artificial Sequence
<220> FEATURE:
<223> OTHER INFORMATION: primer P2

<400> SEQUENCE: 36
atgatcgaat tcgaaatcaa ataatgattt tattttgact g                   41

<210> SEQ ID NO 37
<211> LENGTH: 120
<212> TYPE: DNA
<213> ORGANISM: Artificial Sequence
<220> FEATURE:
<223> OTHER INFORMATION: DNA fragment containing attL

<400> SEQUENCE: 37
agatcttgaa gcctgctttt ttatactaag ttggcattat aaaaaagcat tgcttatcaa    60
tttgttgcaa cgaacaggtc actatcagtc aaaataaaat cattatttga tttcgaattc   120

<210> SEQ ID NO 38
<211> LENGTH: 41
<212> TYPE: DNA
<213> ORGANISM: Artificial Sequence
<220> FEATURE:
<223> OTHER INFORMATION: primer P3

<400> SEQUENCE: 38
atgccactgc agtctgttac aggtcactaa taccatctaa g                   41

<210> SEQ ID NO 39
<211> LENGTH: 46
<212> TYPE: DNA
<213> ORGANISM: Artificial Sequence
<220> FEATURE:
<223> OTHER INFORMATION: primer P4
```

```
<400> SEQUENCE: 39
accgttaagc tttctagacg ctcaagttag tataaaaaag ctgaac                      46

<210> SEQ ID NO 40
<211> LENGTH: 184
<212> TYPE: DNA
<213> ORGANISM: Artificial Sequence
<220> FEATURE:
<223> OTHER INFORMATION: DNA fragment containing attR

<400> SEQUENCE: 40
ctgcagtctg ttacaggtca ctaataccat ctaagtagtt gattcatagt gactgcatat       60
gttgtgtttt acagtattat gtagtctgtt ttttatgcaa aatctaattt aatatattga      120
tatttatatc attttacgtt tctcgttcag cttttttata ctaacttgag cgtctagaaa      180
gctt                                                                   184

<210> SEQ ID NO 41
<211> LENGTH: 38
<212> TYPE: DNA
<213> ORGANISM: Artificial Sequence
<220> FEATURE:
<223> OTHER INFORMATION: primer P5

<400> SEQUENCE: 41
ttcttagacg tcaggtggca cttttcgggg aaatgtgc                               38

<210> SEQ ID NO 42
<211> LENGTH: 37
<212> TYPE: DNA
<213> ORGANISM: Artificial Sequence
<220> FEATURE:
<223> OTHER INFORMATION: primer P6

<400> SEQUENCE: 42
taacagagat ctcgcgcaga aaaaaggat ctcaaga                                 37

<210> SEQ ID NO 43
<211> LENGTH: 46
<212> TYPE: DNA
<213> ORGANISM: Artificial Sequence
<220> FEATURE:
<223> OTHER INFORMATION: primer P7

<400> SEQUENCE: 43
aacagagatc taagcttaga tcctttgcct ggcggcagta gcgcgg                      46

<210> SEQ ID NO 44
<211> LENGTH: 35
<212> TYPE: DNA
<213> ORGANISM: Artificial Sequence
<220> FEATURE:
<223> OTHER INFORMATION: primer P8

<400> SEQUENCE: 44
ataaactgca gcaaaaagag tttgtagaaa cgcaa                                  35

<210> SEQ ID NO 45
<211> LENGTH: 1388
<212> TYPE: DNA
<213> ORGANISM: Artificial Sequence
<220> FEATURE:
<223> OTHER INFORMATION: DNA fragment containing Tc gene and ter_thrL

<400> SEQUENCE: 45
```

```
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc atttttcggcg aggaccgctt tcgctggagc gcgacgatga tcggcctgtc     840
gcttgcggta ttcggaatct tgcacgccct cgctcaagcc ttcgtcactg gtcccgccac     900
caaacgtttc ggcgagaagc aggccattat cgccggcatg gcggccgacg cgctgggcta     960
cgtcttgctg gcgttcgcga cgcgaggctg gatggccttc cccattatga ttcttctcgc    1020
ttccggcggc atcgggatgc ccgcgttgca ggccatgctg tccaggcagg tagatgacga    1080
ccatcaggga cagcttcaag gatcgctcgc ggctcttacc agcctaactt cgatcactgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
actagaaagc ttaacacaga aaaagcccg cacctgacag tgcgggcttt ttttttcgac    1380
cactgcag                                                           1388
```

<210> SEQ ID NO 46
<211> LENGTH: 36
<212> TYPE: DNA
<213> ORGANISM: Artificial Sequence
<220> FEATURE:
<223> OTHER INFORMATION: primer P9

<400> SEQUENCE: 46

```
agtaattcta gaaagcttaa cacagaaaaa agcccg                                36
```

<210> SEQ ID NO 47
<211> LENGTH: 43
<212> TYPE: DNA
<213> ORGANISM: Artificial Sequence
<220> FEATURE:
<223> OTHER INFORMATION: primer P10

<400> SEQUENCE: 47

```
ctagtaggat ccctgcagtg gtcgaaaaaa aaagcccgca ctg                        43
```

<210> SEQ ID NO 48
<211> LENGTH: 329
<212> TYPE: PRT
<213> ORGANISM: Enterobacter aerogenes

<400> SEQUENCE: 48

```
Met Lys Ile Ala Val Tyr Ser Thr Lys Gln Tyr Asp Lys Lys Tyr Leu
1               5                   10                  15

Gln His Val Asn Asp Ala Tyr Gly Phe Glu Leu Glu Phe Phe Asp Phe
            20                  25                  30

Leu Leu Thr Glu Lys Thr Ala Lys Thr Ala Asn Gly Cys Glu Ala Val
            35                  40                  45

Cys Ile Phe Val Asn Asp Gly Ser Arg Pro Val Leu Glu Leu
        50                  55                  60

Lys Ala His Gly Val Lys Tyr Ile Ala Leu Arg Cys Ala Gly Phe Asn
65                  70                  75                  80

Asn Val Asp Leu Asp Ala Ala Lys Glu Leu Gly Leu Arg Val Val Arg
                85                  90                  95

Val Pro Ala Tyr Ser Pro Glu Ala Val Ala Glu His Ala Ile Gly Met
                100                 105                 110

Met Met Ser Leu Asn Arg Arg Ile His Arg Ala Tyr Gln Arg Thr Arg
            115                 120                 125

Asp Ala Asn Phe Ser Leu Glu Gly Leu Thr Gly Phe Thr Met Tyr Gly
            130                 135                 140

Lys Thr Ala Gly Val Ile Gly Thr Gly Lys Ile Gly Val Ala Thr Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Asp Leu Gly Val Glu Tyr Val Asp Leu Pro
                180                 185                 190

Thr Leu Tyr Ala Gln Ser Asp Val Ile Ser Leu His Cys Pro Leu Thr
            195                 200                 205

Asn Glu Asn Tyr His Leu Leu Asn Gln Ala Ala Phe Asp Gln Met Lys
            210                 215                 220

Asp Gly Val Met Val Ile Asn Thr Ser Arg Gly Ala Leu Ile Asp Ser
225                 230                 235                 240

Gln Ala Ala Ile Asp Ala Leu Lys His Gln Lys Ile Gly Ala Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Val Phe Arg Arg Leu Ser Ala Cys His
            275                 280                 285

Asn Val Leu Phe Thr Gly His Gln Ala Phe Leu Thr Ala Glu Ala Leu
            290                 295                 300

Ile Gly Ile Ser Glu Thr Thr Leu Gly Asn Leu Gln Gln Val Ala Lys
305                 310                 315                 320

Gly Glu Thr Cys Pro Asn Ala Leu Val
                325

<210> SEQ ID NO 49
<211> LENGTH: 915
<212> TYPE: PRT
<213> ORGANISM: Enterobacter aerogenes

<400> SEQUENCE: 49

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
            35                  40                  45
```

```
Leu Ala Lys Met Ala Val Ala Glu Ser Gly Met Gly Ile Ile Glu Asp
     50                  55                  60
Lys Val Ile Lys Asn His Phe Ala Ser Glu Tyr Ile Tyr Asn Ala Tyr
 65                  70                  75                  80
Lys Asp Glu Lys Thr Cys Gly Val Leu Ser Asp Asp Thr Phe Gly
                 85                  90                  95
Thr Ile Thr Ile Ala Glu Pro Ile Gly Ile Ile Cys Gly Ile Val Pro
                100                 105                 110
Thr Thr Asn Pro Thr Ser Thr Ala Ile Phe Lys Ser Leu Ile Ser Leu
             115                 120                 125
Lys Thr Arg Asn Ala Ile Ile Phe Ser Pro His Pro Arg Ala Lys Asp
130                 135                 140
Ala Thr Asn Lys Ala Ala Asp Ile Val Leu Gln Ala Ala Ile Ala Ala
145                 150                 155                 160
Gly Ala Pro Lys Asp Leu Ile Gly Trp Ile Asp Gln Pro Ser Val Glu
                165                 170                 175
Leu Ser Asn Ala Leu Met His His Pro Asp Ile Asn Leu Ile Leu Ala
             180                 185                 190
Thr Gly Gly Pro Gly Met Val Lys Ala Ala Tyr Ser Ser Gly Lys Pro
         195                 200                 205
Ala Ile Gly Val Gly Ala Gly Asn Thr Pro Val Val Ile Asp Glu Thr
     210                 215                 220
Ala Asp Ile Lys Arg Ala Val Ala Ser Val Leu Met Ser Lys Thr Phe
225                 230                 235                 240
Asp Asn Gly Val Ile Cys Ala Ser Glu Gln Ser Val Val Val Asp
                245                 250                 255
Ser Val Tyr Asp Ala Val Arg Glu Arg Phe Ala Ser His Gly Gly Tyr
         260                 265                 270
Leu Leu Gln Gly Lys Glu Leu Lys Ala Val Gln Asp Ile Ile Leu Lys
     275                 280                 285
Asn Gly Ala Leu Asn Ala Ala Ile Val Gly Gln Pro Ala Ala Lys Ile
290                 295                 300
Ala Glu Leu Ala Gly Phe Thr Val Pro Ala Thr Thr Lys Ile Leu Ile
305                 310                 315                 320
Gly Glu Val Thr Asp Val Asp Glu Ser Glu Pro Phe Ala His Glu Lys
                325                 330                 335
Leu Ser Pro Thr Leu Ala Met Tyr Arg Ala Lys Asp Phe Glu Asp Ala
             340                 345                 350
Val Asn Lys Ala Glu Lys Leu Val Ala Met Gly Gly Ile Gly His Thr
         355                 360                 365
Ser Cys Leu Tyr Thr Asp Gln Asp Asn Gln Pro Ala Arg Val Ala Tyr
     370                 375                 380
Phe Gly Gln Met Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                405                 410                 415
Leu Thr Leu Gly Cys Gly Ser Trp Gly Gly Asn Ser Ile Ser Glu Asn
             420                 425                 430
Val Gly Pro Lys His Leu Ile Asn Lys Lys Thr Val Ala Lys Arg Ala
         435                 440                 445
Glu Asn Met Leu Trp His Lys Leu Pro Lys Ser Ile Tyr Phe Arg Arg
450                 455                 460
Gly Ser Leu Pro Ile Ala Leu Asp Glu Val Ile Thr Asp Gly His Lys
```

```
              465                 470                 475                 480
        Arg Ala Leu Ile Val Thr Asp Arg Phe Leu Phe Asn Asn Gly Tyr Ala
                        485                 490                 495
        Asp Gln Ile Thr Ser Val Leu Lys Ala Ala Gly Val Glu Thr Glu Val
                        500                 505                 510
        Phe Phe Glu Val Glu Ala Asp Pro Thr Leu Thr Ile Val Arg Lys Gly
                        515                 520                 525
        Ala Asp Leu Ala Asn Ser Phe Lys Pro Asp Val Ile Ile Ala Leu Gly
                        530                 535                 540
        Gly Gly Ser Pro Met Asp Ala Ala Lys Ile Met Trp Val Met Tyr Glu
        545                 550                 555                 560
        His Pro Glu Thr His Phe Glu Glu Leu Ala Leu Arg Phe Met Asp Ile
                        565                 570                 575
        Arg Lys Arg Ile Tyr Lys Phe Pro Lys Met Gly Val Lys Ala Lys Met
                        580                 585                 590
        Val Ala Ile Thr Thr Thr Ser Gly Thr Gly Ser Glu Val Thr Pro Phe
                        595                 600                 605
        Ala Val Val Thr Asp Asp Ala Thr Gly Gln Lys Tyr Pro Leu Ala Asp
                        610                 615                 620
        Tyr Ala Leu Thr Pro Asp Met Ala Ile Val Asp Ala Asn Leu Val Met
        625                 630                 635                 640
        Asp Met Pro Lys Ser Leu Cys Ala Phe Gly Gly Leu Asp Ala Val Thr
                        645                 650                 655
        His Ala Leu Glu Ala Tyr Val Ser Val Leu Ala Ser Glu Phe Ser Asp
                        660                 665                 670
        Gly Gln Ala Leu Gln Ala Leu Lys Leu Leu Lys Glu Tyr Leu Pro Ala
                        675                 680                 685
        Ser Tyr His Glu Gly Ser Lys Asn Pro Val Ala Arg Glu Arg Val His
                        690                 695                 700
        Ser Ala Ala Thr Ile Ala Gly Ile Ala Phe Ala Asn Ala Phe Leu Gly
        705                 710                 715                 720
        Val Cys His Ser Met Ala His Lys Leu Gly Ser Gln Phe His Ile Pro
                        725                 730                 735
        His Gly Leu Ala Asn Ala Leu Leu Ile Ser Asn Val Ile Arg Tyr Asn
                        740                 745                 750
        Ala Asn Asp Asn Pro Thr Lys Gln Thr Ala Phe Ser Gln Tyr Asp Arg
                        755                 760                 765
        Pro Gln Ala Arg Arg Arg Tyr Ala Glu Ile Ala Asp His Leu Gly Leu
                        770                 775                 780
        Ser Ala Pro Gly Asp Arg Thr Ala Ala Lys Ile Glu Lys Leu Leu Ala
        785                 790                 795                 800
        Trp Leu Glu Ser Leu Lys Ala Glu Leu Gly Ile Pro Lys Ser Ile Arg
                        805                 810                 815
        Glu Ala Gly Val Gln Glu Ala Asp Phe Leu Ala His Val Asp Lys Leu
                        820                 825                 830
        Ser Glu Asp Ala Phe Asp Asp Gln Cys Thr Gly Ala Asn Pro Arg Tyr
                        835                 840                 845
        Pro Leu Ile Ala Glu Leu Lys Gln Ile Leu Leu Asp Thr Tyr Tyr Gly
                        850                 855                 860
        Arg Asp Phe Val Glu Gly Glu Ala Ala Val Lys Lys Glu Ala Ala
        865                 870                 875                 880
        Pro Ala Lys Ala Glu Lys Lys Asp Glu Lys Ile Arg Leu Ile Arg Arg
                        885                 890                 895
```

```
Ile Glu Met Asn Glu Ala Pro Ser Ile Asp Gly Ala Phe Phe Ile Phe
            900                 905                 910
Val Leu Tyr
        915

<210> SEQ ID NO 50
<211> LENGTH: 2688
<212> TYPE: DNA
<213> ORGANISM: Enterobacter aerogenes
<220> FEATURE:
<221> NAME/KEY: CDS
<222> LOCATION: (301)..(2448)

<400> SEQUENCE: 50
tcgtgaactg tccctgggta aactgggcgt tctgggcttc gaagttgatc acgagcgtaa    60
cctggctgcc cgtttcggca gtctggctt catcaacaaa gaaggcaccc gccctgccgt    120
ggttatcccg accaacgaag agctggtgat cgctcaagac gcacaccgtc tgaccgctta   180
attccacacc gccagcgata atcctgactg cttcgagttg ccacttgaag tatgaacggt   240
aagctggcgg tgctgttttg tatcccgcct aaaactggcg gtaacgaaag aggatatatc   300 gtg tcc cgt act atc atg ctg atc cct acc gga acc agc gta ggc ctg    348
Val Ser Arg Thr Ile Met Leu Ile Pro Thr Gly Thr Ser Val Gly Leu
1               5                  10                  15 acc agc gtc agc ctc ggt gtt atc cgc gct atg gaa cgc aaa ggc gtt    396
Thr Ser Val Ser Leu Gly Val Ile Arg Ala Met Glu Arg Lys Gly Val
            20                  25                  30 cgc ctg agc gtc ttt aaa cct atc gcc cag ccg cgt tcc ggt ggc gat    444
Arg Leu Ser Val Phe Lys Pro Ile Ala Gln Pro Arg Ser Gly Gly Asp
        35                  40                  45 act cca gac cag act acc acc atc gtt cgc gcc agc tct tca acg acg    492
Thr Pro Asp Gln Thr Thr Thr Ile Val Arg Ala Ser Ser Ser Thr Thr
    50                  55                  60 act gcc gct gaa ccg atg aac atg agc cac gtt gag tcg ctg ctg tcc    540
Thr Ala Ala Glu Pro Met Asn Met Ser His Val Glu Ser Leu Leu Ser
65                  70                  75                  80 agc aac cag aaa gac gtg ctg atg gaa gag atc atc gcc aac tac cat    588
Ser Asn Gln Lys Asp Val Leu Met Glu Glu Ile Ile Ala Asn Tyr His
                85                  90                  95 gcc aac act cag gat gct gaa gtg gtg ctg gtt gaa ggc ctg gtc ccg    636
Ala Asn Thr Gln Asp Ala Glu Val Val Leu Val Glu Gly Leu Val Pro
            100                 105                 110 act cgt aaa cac cag ttc gct cag tct ctg aac tac gaa atc gca aaa    684
Thr Arg Lys His Gln Phe Ala Gln Ser Leu Asn Tyr Glu Ile Ala Lys
        115                 120                 125 acg ctt aac gcg gaa atc gtc ttc gtg atg tct cag ggc acc gat acc    732
Thr Leu Asn Ala Glu Ile Val Phe Val Met Ser Gln Gly Thr Asp Thr
    130                 135                 140 ccg gaa cag ctg aac gag cgt atc gaa ctg act cgc aac agc ttc ggc    780
Pro Glu Gln Leu Asn Glu Arg Ile Glu Leu Thr Arg Asn Ser Phe Gly
145                 150                 155                 160 ggc gcg aaa aac acc agc atc act ggc gtt atc gtt aac aaa ctg aat    828
Gly Ala Lys Asn Thr Ser Ile Thr Gly Val Ile Val Asn Lys Leu Asn
                165                 170                 175 gct ccg gtt gat gaa caa ggc cgt aca cgc cct gac ctg tcc gaa atc    876
Ala Pro Val Asp Glu Gln Gly Arg Thr Arg Pro Asp Leu Ser Glu Ile
            180                 185                 190 ttt gac gac tcg tct aaa gcg aaa gtc gtg aag atc gac ccg gct caa    924
Phe Asp Asp Ser Ser Lys Ala Lys Val Val Lys Ile Asp Pro Ala Gln
        195                 200                 205 ctg cag aat ggc agc ccg ctg ccg gtg ctg ggc gcg gtg cca tgg agc    972
```

```
                    Leu Gln Asn Gly Ser Pro Leu Pro Val Leu Gly Ala Val Pro Trp Ser
                        210                 215                 220 ttc gat ctg atc gcc acg cgc gct atc gac atg gcg cat cac ctg aat         1020
Phe Asp Leu Ile Ala Thr Arg Ala Ile Asp Met Ala His His Leu Asn
225                 230                 235                 240 gcg acc gtg atc aac gaa ggc gac atc aat act cgc cgc gtg aag tct         1068
Ala Thr Val Ile Asn Glu Gly Asp Ile Asn Thr Arg Arg Val Lys Ser
            245                 250                 255 gta acc ttc tgc gcg cgc agc att ccg cac atg ctg gaa cac ttc cgt         1116
Val Thr Phe Cys Ala Arg Ser Ile Pro His Met Leu Glu His Phe Arg
            260                 265                 270 ccg ggt tct ctg ctg gtg act tcc gca gac cgt cca gac gta ctg gtc         1164
Pro Gly Ser Leu Leu Val Thr Ser Ala Asp Arg Pro Asp Val Leu Val
        275                 280                 285 gct gcc tgc ctg gcg gcg atg aac ggc gta gaa atc ggc gct atc ctg         1212
Ala Ala Cys Leu Ala Ala Met Asn Gly Val Glu Ile Gly Ala Ile Leu
    290                 295                 300 ctg acc ggc ggc tat gaa atg gac gcg cgc atc agc aag ctg tgc gaa         1260
Leu Thr Gly Gly Tyr Glu Met Asp Ala Arg Ile Ser Lys Leu Cys Glu
305                 310                 315                 320 cgt gct ttc gcc acc ggc ctg ccg gta ttc atg gtt aac acc aac acc         1308
Arg Ala Phe Ala Thr Gly Leu Pro Val Phe Met Val Asn Thr Asn Thr
                325                 330                 335 tgg cag acc tct ctg agc ctg cag agc ttc aac ctg gaa gta ccg gtt         1356
Trp Gln Thr Ser Leu Ser Leu Gln Ser Phe Asn Leu Glu Val Pro Val
            340                 345                 350 gac gat cac gag cgc atc gag aaa gtt cag gaa tac gtt gct aac tat         1404
Asp Asp His Glu Arg Ile Glu Lys Val Gln Glu Tyr Val Ala Asn Tyr
            355                 360                 365 atc aac gcc gac tgg atc gaa tcg ctg acc gcg acc tcc gag cgc agc         1452
Ile Asn Ala Asp Trp Ile Glu Ser Leu Thr Ala Thr Ser Glu Arg Ser
370                 375                 380 cgt cgt ctg tct ccg cct gcc ttc cgc tac cag ctg acc gag ctg gcg         1500
Arg Arg Leu Ser Pro Pro Ala Phe Arg Tyr Gln Leu Thr Glu Leu Ala
385                 390                 395                 400 cgt aaa gcg ggc aaa cgc gtc gtt ctg ccg gaa ggc gac gaa ccg cgt         1548
Arg Lys Ala Gly Lys Arg Val Val Leu Pro Glu Gly Asp Glu Pro Arg
                405                 410                 415 act gtt aaa gcg gcg gcc atc tgt gcc gag cgc ggt att gca acc tgc         1596
Thr Val Lys Ala Ala Ala Ile Cys Ala Glu Arg Gly Ile Ala Thr Cys
            420                 425                 430 gtg ctg ctg ggc aac ccg gat gag atc aac cgc gtt gcg gcc tct cag         1644
Val Leu Leu Gly Asn Pro Asp Glu Ile Asn Arg Val Ala Ala Ser Gln
        435                 440                 445 ggc gta gag ctg ggc gct ggt att gaa atc gtc gat ccg gaa gtg gtt         1692
Gly Val Glu Leu Gly Ala Gly Ile Glu Ile Val Asp Pro Glu Val Val
    450                 455                 460 cgc gaa agc tac gtg gcg cgt ctg gtc gaa ctg cgt aag aac aaa ggc         1740
Arg Glu Ser Tyr Val Ala Arg Leu Val Glu Leu Arg Lys Asn Lys Gly
465                 470                 475                 480 atg acc gaa gcg gtt gcg cgc gaa cag ctg gaa gat aac gtt gtt ctc         1788
Met Thr Glu Ala Val Ala Arg Glu Gln Leu Glu Asp Asn Val Val Leu
                485                 490                 495 ggc acc ctg atg ctg gaa caa gac gaa gtc gac ggc ctg gta tcc ggc         1836
Gly Thr Leu Met Leu Glu Gln Asp Glu Val Asp Gly Leu Val Ser Gly
            500                 505                 510 gcg gtt cac acc acc gcc aat acc atc cgt ccg ccg ctg cag ctt atc         1884
Ala Val His Thr Thr Ala Asn Thr Ile Arg Pro Pro Leu Gln Leu Ile
        515                 520                 525 aaa acg gcg ccg ggc agc tcg ctg gtc tct tcc gta ttc ttc atg ctg         1932
Lys Thr Ala Pro Gly Ser Ser Leu Val Ser Ser Val Phe Phe Met Leu
```

```
                       Lys Thr Ala Pro Gly Ser Ser Leu Val Ser Ser Val Phe Phe Met Leu
                           530                 535                 540 ctg ccg gaa cag gtt tac gtt tac ggc gac tgc gcg atc aac ccg gat        1980
Leu Pro Glu Gln Val Tyr Val Tyr Gly Asp Cys Ala Ile Asn Pro Asp
545                 550                 555                 560 ccg act gct gaa cag ctg gcg gaa atc gcg att cag tcc gct gat tcc        2028
Pro Thr Ala Glu Gln Leu Ala Glu Ile Ala Ile Gln Ser Ala Asp Ser
                565                 570                 575 gcg att gcc ttc ggt atc gaa ccg cgt gtg gcg atg ctc tcc tac tcc        2076
Ala Ile Ala Phe Gly Ile Glu Pro Arg Val Ala Met Leu Ser Tyr Ser
            580                 585                 590 acc ggc acc tcc ggc gca ggt agc gat gta gaa aaa gta cgc gaa gca        2124
Thr Gly Thr Ser Gly Ala Gly Ser Asp Val Glu Lys Val Arg Glu Ala
        595                 600                 605 act cgt ctg gcg caa gaa aaa cgt cct gac ctg atg atc gac ggt ccg        2172
Thr Arg Leu Ala Gln Glu Lys Arg Pro Asp Leu Met Ile Asp Gly Pro
    610                 615                 620 ctg cag tat gat gcc gcg gta atg gcc gat gtt gcg aag tcc aaa gcg        2220
Leu Gln Tyr Asp Ala Ala Val Met Ala Asp Val Ala Lys Ser Lys Ala
625                 630                 635                 640 cca aac tct ccg gta gct ggc cgc gcg acc gtg ttc atc ttc ccg gat        2268
Pro Asn Ser Pro Val Ala Gly Arg Ala Thr Val Phe Ile Phe Pro Asp
                645                 650                 655 ctg aac acc ggt aac acc act tac aaa gcc gta cag cgt tcc gct gac        2316
Leu Asn Thr Gly Asn Thr Thr Tyr Lys Ala Val Gln Arg Ser Ala Asp
            660                 665                 670 ctg atc tcc atc ggg ccg atg ctg cag ggt atg cgt aag ccg gta aac        2364
Leu Ile Ser Ile Gly Pro Met Leu Gln Gly Met Arg Lys Pro Val Asn
        675                 680                 685 gac ctg tcc cgc ggc gcg ctg gta gac gat atc gtc tac acc atc gca        2412
Asp Leu Ser Arg Gly Ala Leu Val Asp Asp Ile Val Tyr Thr Ile Ala
    690                 695                 700 ctg acg gcg att cag tct tct cag cag cag aaa taa tctcccgctg             2458
Leu Thr Ala Ile Gln Ser Ser Gln Gln Gln Lys
705                 710                 715 agacaagaaa ggcagccaaa tggctgcctt ttttatggct ctaacgcgta aaggaaatta     2518
cgcttcgtct tcttccggct cgtcgcgatc gtggccggta ttgcccgcgt tacgggtcat     2578
ccacagcgcc agcgctttca gtgaatcggc ggtgaactca tcgcagcgcg cggtgatctc     2638
ttccggcgtc aaccagcata cctcgctgac ctcttcttcc tgcagggcga                2688

<210> SEQ ID NO 51
<211> LENGTH: 715
<212> TYPE: PRT
<213> ORGANISM: Enterobacter aerogenes

<400> SEQUENCE: 51

Val Ser Arg Thr Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
                20                  25                  30

Arg Leu Ser Val Phe Lys Pro Ile Ala Gln Pro Arg Ser Gly Gly Asp
            35                  40                  45

Thr Pro Asp Gln Thr Thr Thr Ile Val Arg Ala Ser Ser Ser Thr Thr
        50                  55                  60

Thr Ala Ala Glu Pro Met Asn Met Ser His Val Glu Ser Leu Leu Ser
65                  70                  75                  80

Ser Asn Gln Lys Asp Val Leu Met Glu Glu Ile Ile Ala Asn Tyr His
                85                  90                  95
```

Ala Asn Thr Gln Asp Ala Glu Val Val Leu Val Glu Gly Leu Val Pro
                100                 105                 110

Thr Arg Lys His Gln Phe Ala Gln Ser Leu Asn Tyr Glu Ile Ala Lys
                115                 120                 125

Thr Leu Asn Ala Glu Ile Val Phe Val Met Ser Gln Gly Thr Asp Thr
            130                 135                 140

Pro Glu Gln Leu Asn Glu Arg Ile Glu Leu Thr Arg Asn Ser Phe Gly
145                 150                 155                 160

Gly Ala Lys Asn Thr Ser Ile Thr Gly Val Ile Val Asn Lys Leu Asn
                    165                 170                 175

Ala Pro Val Asp Glu Gln Gly Arg Thr Arg Pro Asp Leu Ser Glu Ile
                180                 185                 190

Phe Asp Asp Ser Ser Lys Ala Lys Val Val Lys Ile Asp Pro Ala Gln
            195                 200                 205

Leu Gln Asn Gly Ser Pro Leu Pro Val Leu Gly Ala Val Pro Trp Ser
    210                 215                 220

Phe Asp Leu Ile Ala Thr Arg Ala Ile Asp Met Ala His His Leu Asn
225                 230                 235                 240

Ala Thr Val Ile Asn Glu Gly Asp Ile Asn Thr Arg Arg Val Lys Ser
                    245                 250                 255

Val Thr Phe Cys Ala Arg Ser Ile Pro His Met Leu Glu His Phe Arg
                260                 265                 270

Pro Gly Ser Leu Leu Val Thr Ser Ala Asp Arg Pro Asp Val Leu Val
            275                 280                 285

Ala Ala Cys Leu Ala Ala Met Asn Gly Val Glu Ile Gly Ala Ile Leu
    290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                    325                 330                 335

Trp Gln Thr Ser Leu Ser Leu Gln Ser Phe Asn Leu Glu Val Pro Val
                340                 345                 350

Asp Asp His Glu Arg Ile Glu Lys Val Gln Glu Tyr Val Ala Asn Tyr
            355                 360                 365

Ile Asn Ala Asp Trp Ile Glu Ser Leu Thr Ala Thr Ser Glu Arg Ser
    370                 375                 380

Arg Arg Leu Ser Pro Pro Ala Phe Arg Tyr Gln Leu Thr Glu Leu Ala
385                 390                 395                 400

Arg Lys Ala Gly Lys Arg Val Val Leu Pro Glu Gly Asp Glu Pro Arg
                    405                 410                 415

Thr Val Lys Ala Ala Ile Cys Ala Glu Arg Gly Ile Ala Thr Cys
                420                 425                 430

Val Leu Leu Gly Asn Pro Asp Glu Ile Asn Arg Val Ala Ala Ser Gln
            435                 440                 445

Gly Val Glu Leu Gly Ala Gly Ile Glu Ile Val Asp Pro Glu Val Val
    450                 455                 460

Arg Glu Ser Tyr Val Ala Arg Leu Val Glu Leu Arg Lys Asn Lys Gly
465                 470                 475                 480

Met Thr Glu Ala Val Ala Arg Glu Gln Leu Glu Asp Asn Val Val Leu
                    485                 490                 495

Gly Thr Leu Met Leu Glu Gln Asp Glu Val Asp Gly Leu Val Ser Gly
                500                 505                 510

Ala Val His Thr Thr Ala Asn Thr Ile Arg Pro Pro Leu Gln Leu Ile

```
              515                 520                 525
Lys Thr Ala Pro Gly Ser Ser Leu Val Ser Ser Val Phe Phe Met Leu
         530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ile Ala Phe Gly Ile Glu Pro Arg Val Ala Met Leu Ser Tyr Ser
                580                 585                 590

Thr Gly Thr Ser Gly Ala Gly Ser Asp Val Glu Lys Val Arg Glu Ala
            595                 600                 605

Thr Arg Leu Ala Gln Glu Lys Arg Pro Asp Leu Met Ile Asp Gly Pro
        610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
                660                 665                 670

Leu Ile Ser Ile Gly Pro Met Leu Gln Gly Met Arg Lys Pro Val Asn
            675                 680                 685

Asp Leu Ser Arg Gly Ala Leu Val Asp Asp Ile Val Tyr Thr Ile Ala
        690                 695                 700

Leu Thr Ala Ile Gln Ser Ser Gln Gln Gln Lys
705                 710                 715

<210> SEQ ID NO 52
<211> LENGTH: 1125
<212> TYPE: DNA
<213> ORGANISM: Enterobacter aerogenes
<220> FEATURE:
<221> NAME/KEY: CDS
<222> LOCATION: (181)..(846)

<400> SEQUENCE: 52
agttctttcg ctgcccgggt gaagtgccgc gtccgggcga cggcgacaaa atagcgtaga     60
taacgaagtt ccatatcgaa aacgtctcaa accagcatgg tttctatatt ggaactgtga    120
gctgaatcgg gtcaaccttt atttaacctt tcttatattt gttgaacgag gaagtggctc    180 atg aat cat gct tca gat tgc acc tgt gaa gag agt ctg tgt gaa acg      228
Met Asn His Ala Ser Asp Cys Thr Cys Glu Glu Ser Leu Cys Glu Thr
1               5                  10                  15 cta cgc gcg ttt tcc gct cag cat ccc gat agc gtg ctg tat caa act      276
Leu Arg Ala Phe Ser Ala Gln His Pro Asp Ser Val Leu Tyr Gln Thr
                20                  25                  30 tcg ctg atg agc gcc ctg ctc agc ggc gtc tac gaa ggt acc acc act      324
Ser Leu Met Ser Ala Leu Leu Ser Gly Val Tyr Glu Gly Thr Thr Thr
            35                  40                  45 att gcg gac ctg ctg aag cac ggt gat ttc ggg ctc ggc act ttt aat      372
Ile Ala Asp Leu Leu Lys His Gly Asp Phe Gly Leu Gly Thr Phe Asn
        50                  55                  60 gaa ctc gac ggc gag ctg atc gcg ttt agc agc cag gtt tat caa ctg      420
Glu Leu Asp Gly Glu Leu Ile Ala Phe Ser Ser Gln Val Tyr Gln Leu
65                  70                  75                  80 cgt gcc gac ggc agc gcg cgt aaa gcg cgt ccg gaa cag aaa acg ccg      468
Arg Ala Asp Gly Ser Ala Arg Lys Ala Arg Pro Glu Gln Lys Thr Pro
                85                  90                  95 ttt gca gtg atg acc tgg ttt cag ccg cag tac cgt aaa acc ttt gac      516
```

```
                Phe Ala Val Met Thr Trp Phe Gln Pro Gln Tyr Arg Lys Thr Phe Asp
                                100                 105                 110 cat ccg gtc agc cgc cag cag ctg cat gag gtt att gac cag caa att          564
His Pro Val Ser Arg Gln Gln Leu His Glu Val Ile Asp Gln Gln Ile
            115                 120                 125 cct tcc gac aat ctg ttc tgc gcg ctg cga atc gat ggt cat ttc cgc          612
Pro Ser Asp Asn Leu Phe Cys Ala Leu Arg Ile Asp Gly His Phe Arg
        130                 135                 140 cac gcc cat acc cgc acc gtg cct cgt cag acg ccg ccc tac cgg gcg          660
His Ala His Thr Arg Thr Val Pro Arg Gln Thr Pro Pro Tyr Arg Ala
145                 150                 155                 160 atg acc gac gtg ctc gac gat cag ccg gtt ttc cgc ttt aac cag cgt          708
Met Thr Asp Val Leu Asp Asp Gln Pro Val Phe Arg Phe Asn Gln Arg
                165                 170                 175 gac ggc gta ctg gtc ggt ttt cgg acc ccc agc ata tgc agg gaa tta          756
Asp Gly Val Leu Val Gly Phe Arg Thr Pro Ser Ile Cys Arg Glu Leu
            180                 185                 190 acg tcg ccg gct atc acg aac act tca tta ccg atg acc gcc agg gcg          804
Thr Ser Pro Ala Ile Thr Asn Thr Ser Leu Pro Met Thr Ala Arg Ala
        195                 200                 205 gcg gcc acc tgc tgg act acc agc tcg acc atg ggg tat tga               846
Ala Ala Thr Cys Trp Thr Thr Ser Ser Thr Met Gly Tyr
    210                 215                 220 ccttcggcga aattcataag ctgatgatcg accttcccgc cgacagcgcg ttcctgcagg        906
ccaatttgca tcccgataat ctcgatgccg ccatccgttc agtagaaagt taggaggttc        966
acatggacaa acagtatccg cagcgccagt gggcgcacgg cgccgatctg gtcgtcagcc       1026
aactggaagc gcaaggcgta cggcaggtct tcgggatccc cggcgctaaa atcgataagg       1086
ttttcgactc gttgctggac tcctcaatcc gcattattc                             1125

<210> SEQ ID NO 53
<211> LENGTH: 221
<212> TYPE: PRT
<213> ORGANISM: Enterobacter aerogenes

<400> SEQUENCE: 53

Met Asn His Ala Ser Asp Cys Thr Cys Glu Glu Ser Leu Cys Glu Thr
1               5                   10                  15

Leu Arg Ala Phe Ser Ala Gln His Pro Asp Ser Val Leu Tyr Gln Thr
            20                  25                  30

Ser Leu Met Ser Ala Leu Leu Ser Gly Val Tyr Glu Gly Thr Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Arg Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
```

```
                          165                 170                 175
Asp Gly Val Leu Val Gly Phe Arg Thr Pro Ser Ile Cys Arg Glu Leu
            180                 185                 190

Thr Ser Pro Ala Ile Thr Asn Thr Ser Leu Pro Met Thr Ala Arg Ala
            195                 200                 205

Ala Ala Thr Cys Trp Thr Thr Ser Ser Thr Met Gly Tyr
            210                 215                 220

<210> SEQ ID NO 54
<211> LENGTH: 2823
<212> TYPE: DNA
<213> ORGANISM: Enterobacter aerogenes
<220> FEATURE:
<221> NAME/KEY: CDS
<222> LOCATION: (355)..(2637)

<400> SEQUENCE: 54
cgcagcctga tggacaaagc gatgatcatg gtgttgccgg ttgcgatgtt tgtcgccagc      60
ggctttgaac acagcatcgc taatatgttt atgatcccga tgggtatcgt aattcgcaac     120
tttgcaagcc cggaattctg gaccgctatc ggttcaactc cggagagttt ttctcactta     180
accgttatga acttcatcac tgataacctg attccagtca ctatcggaaa catcatcggc     240
ggtggtttgt tggttgggtt gacatactgg gtcatttacc tgcgtggcga cgatcatcat     300
taatggttgt ctcaggcagt aaataaaaaa tccacttaag aaggtaggtg ttac atg      357
                                                              Met
                                                              1 tcc gag ctt aat gaa aag tta gcc aca gcc tgg gaa ggt ttt gcg aaa      405
Ser Glu Leu Asn Glu Lys Leu Ala Thr Ala Trp Glu Gly Phe Ala Lys
        5                   10                  15 ggt gac tgg cag aac gaa gtc aac gta cgt gac ttt atc cag aaa aac      453
Gly Asp Trp Gln Asn Glu Val Asn Val Arg Asp Phe Ile Gln Lys Asn
            20                  25                  30 tac acc cca tat gaa ggt gac gaa tcc ttc ctg gct ggc gca act gat      501
Tyr Thr Pro Tyr Glu Gly Asp Glu Ser Phe Leu Ala Gly Ala Thr Asp
        35                  40                  45 gcg acc acc aag ctg tgg gac agc gta atg gaa ggc gtt aaa cag gaa      549
Ala Thr Thr Lys Leu Trp Asp Ser Val Met Glu Gly Val Lys Gln Glu
50                  55                  60                  65 aac cgc act cac gcg cct gtt gat ttc gac act tcc ctc gca tcc acc      597
Asn Arg Thr His Ala Pro Val Asp Phe Asp Thr Ser Leu Ala Ser Thr
                70                  75                  80 atc act tct cac gac gcg ggc tac atc gag aaa gcg ctc gag aaa atc      645
Ile Thr Ser His Asp Ala Gly Tyr Ile Glu Lys Ala Leu Glu Lys Ile
            85                  90                  95 gtt ggt ctg caa act gaa gcc ccg ctg aaa cgt gcg att atc ccg ttc      693
Val Gly Leu Gln Thr Glu Ala Pro Leu Lys Arg Ala Ile Ile Pro Phe
        100                 105                 110 ggc ggt atc aaa atg gtt gaa ggt tcc tgc aaa gcg tac aat cgc gaa      741
Gly Gly Ile Lys Met Val Glu Gly Ser Cys Lys Ala Tyr Asn Arg Glu
    115                 120                 125 ctg gac ccg atg ctg aaa aaa atc ttc acc gag tac cgt aaa act cac      789
Leu Asp Pro Met Leu Lys Lys Ile Phe Thr Glu Tyr Arg Lys Thr His
130                 135                 140                 145 aac cag ggc gtt ttc gac gta tat acc ccg gac atc ctg cgc tgc cgt      837
Asn Gln Gly Val Phe Asp Val Tyr Thr Pro Asp Ile Leu Arg Cys Arg
                150                 155                 160 aaa tcc ggc gta ctg acc ggt ctg ccg gat gct tac ggc cgt ggt cgt      885
Lys Ser Gly Val Leu Thr Gly Leu Pro Asp Ala Tyr Gly Arg Gly Arg
            165                 170                 175
```

```
atc atc ggt gac tat cgt cgc gtt gcg ctg tac ggt atc gac ttc ctg      933
Ile Ile Gly Asp Tyr Arg Arg Val Ala Leu Tyr Gly Ile Asp Phe Leu
        180                 185                 190 atg aaa gac aaa ttc gcc cag ttc aac tcg ctg cag gcg aaa ctg gaa      981
Met Lys Asp Lys Phe Ala Gln Phe Asn Ser Leu Gln Ala Lys Leu Glu
    195                 200                 205 agc ggc gaa gat ctg gaa gca acc atc cgt ctg cgt gaa gaa att gct     1029
Ser Gly Glu Asp Leu Glu Ala Thr Ile Arg Leu Arg Glu Glu Ile Ala
210                 215                 220                 225 gaa cag cat cgc gcg ctg ggt cag atc aaa gag atg gcg gct aaa tat     1077
Glu Gln His Arg Ala Leu Gly Gln Ile Lys Glu Met Ala Ala Lys Tyr
                230                 235                 240 ggc tac gac atc tcc ggt ccg gcg act acc gct cag gaa gct att cag     1125
Gly Tyr Asp Ile Ser Gly Pro Ala Thr Thr Ala Gln Glu Ala Ile Gln
            245                 250                 255 tgg acc tac ttc ggt tac ctg gcc gcc gtt aaa tct cag aac ggc gcg     1173
Trp Thr Tyr Phe Gly Tyr Leu Ala Ala Val Lys Ser Gln Asn Gly Ala
        260                 265                 270 gca atg tcc ttc ggt cgt act tcc agc ttc ctg gat atc tac atc gaa     1221
Ala Met Ser Phe Gly Arg Thr Ser Ser Phe Leu Asp Ile Tyr Ile Glu
    275                 280                 285 cgt gac ctg cag gcg ggt aaa atc acc gag caa gac gcg cag gaa atg     1269
Arg Asp Leu Gln Ala Gly Lys Ile Thr Glu Gln Asp Ala Gln Glu Met
290                 295                 300                 305 gtt gac cac ctg gtc atg aaa ctg cgt atg gtt cgc ttc ctg cgt acc     1317
Val Asp His Leu Val Met Lys Leu Arg Met Val Arg Phe Leu Arg Thr
                310                 315                 320 ccg gaa tat gat gaa ctg ttc tcc ggc gac ccg att tgg gca acg gaa     1365
Pro Glu Tyr Asp Glu Leu Phe Ser Gly Asp Pro Ile Trp Ala Thr Glu
            325                 330                 335 tct atc ggt ggt atg ggc gtt gac ggc cgt act ctg gta acc aaa aac     1413
Ser Ile Gly Gly Met Gly Val Asp Gly Arg Thr Leu Val Thr Lys Asn
        340                 345                 350 agc ttc cgc ttc ctg aac acc ctg tac acc atg ggg ccg tct ccg gag     1461
Ser Phe Arg Phe Leu Asn Thr Leu Tyr Thr Met Gly Pro Ser Pro Glu
    355                 360                 365 ccg aac atc act atc ctg tgg tct gaa aaa ctg ccg ctg agc ttt aag     1509
Pro Asn Ile Thr Ile Leu Trp Ser Glu Lys Leu Pro Leu Ser Phe Lys
370                 375                 380                 385 aaa ttc gcc gct aaa gta tcc atc gat acc tct tct ctg cag tac gag     1557
Lys Phe Ala Ala Lys Val Ser Ile Asp Thr Ser Ser Leu Gln Tyr Glu
                390                 395                 400 aac gat gac ctg atg cgc ccg gac ttc aac aac gac gat tac gct atc     1605
Asn Asp Asp Leu Met Arg Pro Asp Phe Asn Asn Asp Asp Tyr Ala Ile
            405                 410                 415 gca tgc tgc gta agc ccg atg att gtt ggt aaa caa atg cag ttc ttc     1653
Ala Cys Cys Val Ser Pro Met Ile Val Gly Lys Gln Met Gln Phe Phe
        420                 425                 430 ggc gct cgc gct aac ctc gcg aaa acc atg ctg tat gct atc aac ggc     1701
Gly Ala Arg Ala Asn Leu Ala Lys Thr Met Leu Tyr Ala Ile Asn Gly
    435                 440                 445 ggc gtt gat gaa aaa ctg aaa atg cag gtt ggt ccg aaa tct gaa ccg     1749
Gly Val Asp Glu Lys Leu Lys Met Gln Val Gly Pro Lys Ser Glu Pro
450                 455                 460                 465 atc aaa ggc gac gtc ctg aac ttc gac gaa gtt atg gag cgc atg gat     1797
Ile Lys Gly Asp Val Leu Asn Phe Asp Glu Val Met Glu Arg Met Asp
                470                 475                 480 cac ttc atg gac tgg ctg gct aaa cag tac gtc acc gcg ctg aac atc     1845
His Phe Met Asp Trp Leu Ala Lys Gln Tyr Val Thr Ala Leu Asn Ile
            485                 490                 495
```

| | | | | | | | | | | | | | | | |
|---|---|---|---|---|---|---|---|---|---|---|---|---|---|---|---|
| att | cat | tac | atg | cat | gac | aag | tac | agc | tac | gaa | gcc | tct | ctg | atg | gcg | 1893
| Ile | His | Tyr | Met | His | Asp | Lys | Tyr | Ser | Tyr | Glu | Ala | Ser | Leu | Met | Ala |
| | 500 | | | | 505 | | | | | 510 | | | | | |

```
att cat tac atg cat gac aag tac agc tac gaa gcc tct ctg atg gcg      1893
Ile His Tyr Met His Asp Lys Tyr Ser Tyr Glu Ala Ser Leu Met Ala
    500                 505                 510 ctg cac gac cgt gac gtt atc cgc acc atg gcg tgt ggt atc gca ggt      1941
Leu His Asp Arg Asp Val Ile Arg Thr Met Ala Cys Gly Ile Ala Gly
515                 520                 525 ctg tcc gtt gct gct gac tcc ctg tct gct atc aaa tat gcg aaa gtt      1989
Leu Ser Val Ala Ala Asp Ser Leu Ser Ala Ile Lys Tyr Ala Lys Val
530                 535                 540                 545 aaa ccg att cgt gac gaa gac ggt ctg gct gtt gac ttc gaa atc gaa      2037
Lys Pro Ile Arg Asp Glu Asp Gly Leu Ala Val Asp Phe Glu Ile Glu
                550                 555                 560 ggc gaa tac ccg cag ttt ggt aac aac gat gct cgc gtc gat gac atg      2085
Gly Glu Tyr Pro Gln Phe Gly Asn Asn Asp Ala Arg Val Asp Asp Met
            565                 570                 575 gcc gtt gac ctg gtt gaa cgt ttc atg aag aaa att cag aaa ctg cac      2133
Ala Val Asp Leu Val Glu Arg Phe Met Lys Lys Ile Gln Lys Leu His
        580                 585                 590 acc tac cgc aac gct atc ccg act cag tcc gtt ctg acc atc act tct      2181
Thr Tyr Arg Asn Ala Ile Pro Thr Gln Ser Val Leu Thr Ile Thr Ser
595                 600                 605 aac gtc gtg tat ggt aag aaa acc ggt aac acc cca gat ggt cgt cgc      2229
Asn Val Val Tyr Gly Lys Lys Thr Gly Asn Thr Pro Asp Gly Arg Arg
610                 615                 620                 625 gct ggc gcg ccg ttc gga cca ggt gct aac ccg atg cac ggc cgt gac      2277
Ala Gly Ala Pro Phe Gly Pro Gly Ala Asn Pro Met His Gly Arg Asp
                630                 635                 640 cag aaa ggt gct gta gcc tct ctg act tcc gtt gct aaa ctg ccg ttt      2325
Gln Lys Gly Ala Val Ala Ser Leu Thr Ser Val Ala Lys Leu Pro Phe
            645                 650                 655 gct tac gct aaa gat ggt atc tct tac acc ttc tct atc gtg ccg aac      2373
Ala Tyr Ala Lys Asp Gly Ile Ser Tyr Thr Phe Ser Ile Val Pro Asn
        660                 665                 670 gcg ctg ggt aaa gat gac gaa gtt cgt aag acc aac ctg gcg ggc ctg      2421
Ala Leu Gly Lys Asp Asp Glu Val Arg Lys Thr Asn Leu Ala Gly Leu
675                 680                 685 atg gat ggt tac ttc cac cac gaa gcg tcc atc gaa ggt ggt cag cac      2469
Met Asp Gly Tyr Phe His His Glu Ala Ser Ile Glu Gly Gly Gln His
690                 695                 700                 705 ctg aac gtg aac gtc atg aac cgc gaa atg ctc ctc gac gcg atg gaa      2517
Leu Asn Val Asn Val Met Asn Arg Glu Met Leu Leu Asp Ala Met Glu
                710                 715                 720 aac ccg gaa aaa tat ccg cag ctg acc att cgt gta tct ggc tac gcg      2565
Asn Pro Glu Lys Tyr Pro Gln Leu Thr Ile Arg Val Ser Gly Tyr Ala
            725                 730                 735 gta cgt ttt aac tcc ctg act aaa gaa cag cag cag gat gtt att acc      2613
Val Arg Phe Asn Ser Leu Thr Lys Glu Gln Gln Gln Asp Val Ile Thr
        740                 745                 750 cgt acc ttc act cag acc atg taa ttccctgtct gactgaaaaa gcgtacaata    2667
Arg Thr Phe Thr Gln Thr Met
755                 760 aaggccccac atcagtgggg ccttttttaac acgtgattcc ctgccccagc ctgctttgcc   2727
agttatctat actttgggta cctgtcaaaa cagacttaac acagccggtt tgagctgtgc   2787
atcacaggcc ctggagggcc gaacccggag atatca                             2823

<210> SEQ ID NO 55
<211> LENGTH: 760
<212> TYPE: PRT
<213> ORGANISM: Enterobacter aerogenes
```

-continued

```
<400> SEQUENCE: 55

Met Ser Glu Leu Asn Glu Lys Leu Ala Thr Ala Trp Glu Gly Phe Ala
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Asp Ala Thr Thr Lys Leu Trp Asp Ser Val Met Glu Gly Val Lys Gln
    50                  55                  60

Glu Asn Arg Thr His Ala Pro Val Asp Phe Asp Thr Ser Leu Ala Ser
65                  70                  75                  80

Thr Ile Thr Ser His Asp Ala Gly Tyr Ile Glu Lys Ala Leu Glu Lys
                85                  90                  95

Ile Val Gly Leu Gln Thr Glu Ala Pro Leu Lys Arg Ala Ile Ile Pro
            100                 105                 110

Phe Gly Gly Ile Lys Met Val Glu Gly Ser Cys Lys Ala Tyr Asn Arg
        115                 120                 125

Glu Leu Asp Pro Met Leu Lys Lys Ile Phe Thr Glu Tyr Arg Lys Thr
130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Phe
            180                 185                 190

Leu Met Lys Asp Lys Phe Ala Gln Phe Asn Ser Leu Gln Ala Lys Leu
        195                 200                 205

Glu Ser Gly Glu Asp Leu Glu Ala Thr Ile Arg Leu Arg Glu Glu Ile
    210                 215                 220

Ala Glu Gln His Arg Ala Leu Gly Gln Ile Lys Glu Met Ala Ala Lys
225                 230                 235                 240

Tyr Gly Tyr Asp Ile Ser Gly Pro Ala Thr Thr Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Ser Phe Leu Asp Ile Tyr Ile
        275                 280                 285

Glu Arg Asp Leu Gln Ala Gly Lys Ile Thr Glu Gln Asp Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Val Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Ile Thr Ile Leu Trp Ser Glu Lys Leu Pro Leu Ser Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415
```

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
            435                 440                 445

Gly Gly Val Asp Glu Lys Leu Lys Met Gln Val Gly Pro Lys Ser Glu
450                 455                 460

Pro Ile Lys Gly Asp Val Leu Asn Phe Asp Glu Val Met Glu Arg Met
465                 470                 475                 480

Asp His Phe Met Asp Trp Leu Ala Lys Gln Tyr Val Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
            515                 520                 525

Gly Leu Ser Val Ala Ala Asp Ser Leu Ser Ala Ile Lys Tyr Ala Lys
        530                 535                 540

Val Lys Pro Ile Arg Asp Glu Asp Gly Leu Ala Val Asp Phe Glu Ile
545                 550                 555                 560

Glu Gly Glu Tyr Pro Gln Phe Gly Asn Asn Asp Ala Arg Val Asp Asp
                565                 570                 575

Met Ala Val Asp Leu Val Glu Arg Phe Met Lys Lys Ile Gln Lys Leu
            580                 585                 590

His Thr Tyr Arg Asn Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
        610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
            660                 665                 670

Asn Ala Leu Gly Lys Asp Glu Val Arg Lys Thr Asn Leu Ala Gly
        675                 680                 685

Leu Met Asp Gly Tyr Phe His His Glu Ala Ser Ile Glu Gly Gly Gln
690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Thr Met
        755                 760

<210> SEQ ID NO 56
<211> LENGTH: 89
<212> TYPE: DNA
<213> ORGANISM: Artificial Sequence
<220> FEATURE:
<223> OTHER INFORMATION: primer

<400> SEQUENCE: 56
atgttaacga cgcatacggc tttgaactgg aatttttcga cttcctgctg accgaaaaga     60
tgaagcctgc ttttttatac taagttggc                                       89

```
<210> SEQ ID NO 57
<211> LENGTH: 90
<212> TYPE: DNA
<213> ORGANISM: Artificial Sequence
<220> FEATURE:
<223> OTHER INFORMATION: primer

<400> SEQUENCE: 57
ggcaggcgga gagccggcgg aacacgtcat cctggatgac atcattcgat ttatcttcaa      60
cgctcaagtt agtataaaaa agctgaacga                                      90

<210> SEQ ID NO 58
<211> LENGTH: 89
<212> TYPE: DNA
<213> ORGANISM: Artificial Sequence
<220> FEATURE:
<223> OTHER INFORMATION: primer

<400> SEQUENCE: 58
ctggcggtgc tgttttgtat cccgcctaaa actggcggta acgaaagagg atatatcgtg      60
tgaagcctgc tttttatac taagttggc                                        89

<210> SEQ ID NO 59
<211> LENGTH: 90
<212> TYPE: DNA
<213> ORGANISM: Artificial Sequence
<220> FEATURE:
<223> OTHER INFORMATION: primer

<400> SEQUENCE: 59
gcgttagagc cataaaaaag gcagccattt ggctgccttt cttgtctcag cgggagatta      60
cgctcaagtt agtataaaaa agctgaacga                                      90

<210> SEQ ID NO 60
<211> LENGTH: 89
<212> TYPE: DNA
<213> ORGANISM: Artificial Sequence
<220> FEATURE:
<223> OTHER INFORMATION: primer

<400> SEQUENCE: 60
gaatcgggtc aacctttatt taacctttct tatatttgtt gaacgaggaa gtggctcatg      60
tgaagcctgc tttttatac taagttggc                                        89

<210> SEQ ID NO 61
<211> LENGTH: 90
<212> TYPE: DNA
<213> ORGANISM: Artificial Sequence
<220> FEATURE:
<223> OTHER INFORMATION: primer

<400> SEQUENCE: 61
cagatcggcg ccgtgcgccc actggcgctg cggatactgt ttgtccatgt gaacctccta      60
cgctcaagtt agtataaaaa agctgaacga                                      90

<210> SEQ ID NO 62
<211> LENGTH: 89
<212> TYPE: DNA
<213> ORGANISM: Artificial Sequence
<220> FEATURE:
<223> OTHER INFORMATION: primer

<400> SEQUENCE: 62
```

-continued

```
cattaatggt tgtctcaggc agtaaataaa aaatccactt aagaaggtag gtgttacatg    60
tgaagcctgc ttttttatac taagttggc                                      89

<210> SEQ ID NO 63
<211> LENGTH: 90
<212> TYPE: DNA
<213> ORGANISM: Artificial Sequence
<220> FEATURE:
<223> OTHER INFORMATION: primer

<400> SEQUENCE: 63
aaaaaggccc cactgatgtg gggcctttat tgtacgcttt ttcagtcaga cagggaatta    60
cgctcaagtt agtataaaaa agctgaacga                                     90

<210> SEQ ID NO 64
<211> LENGTH: 1620
<212> TYPE: DNA
<213> ORGANISM: Selenomonas ruminantium
<220> FEATURE:
<221> NAME/KEY: CDS
<222> LOCATION: (1)..(1620)

<400> SEQUENCE: 64
```

| | | | | | | | | | | | | | | | | |
|---|---|---|---|---|---|---|---|---|---|---|---|---|---|---|---|---|
| atg | gca | aac | atc | gat | ctt | agc | caa | tat | ggc | atc | act | ggt | act | acc | gga | 48 |
| Met | Ala | Asn | Ile | Asp | Leu | Ser | Gln | Tyr | Gly | Ile | Thr | Gly | Thr | Thr | Gly | |
| 1 | | | | 5 | | | | | 10 | | | | | 15 | | |

| att | ctc | cac | aat | ccg | tct | tac | aag | acg | ctt | ttt | gaa | gaa | gag | act | aaa | 96 |
|---|---|---|---|---|---|---|---|---|---|---|---|---|---|---|---|---|
| Ile | Leu | His | Asn | Pro | Ser | Tyr | Lys | Thr | Leu | Phe | Glu | Glu | Glu | Thr | Lys | |
| | | | 20 | | | | | 25 | | | | | 30 | | | |

| gaa | ggt | tta | aca | ggc | tac | gaa | cag | ggt | cag | gtt | tcc | gaa | ctg | ggc | gct | 144 |
|---|---|---|---|---|---|---|---|---|---|---|---|---|---|---|---|---|
| Glu | Gly | Leu | Thr | Gly | Tyr | Glu | Gln | Gly | Gln | Val | Ser | Glu | Leu | Gly | Ala | |
| | | 35 | | | | | 40 | | | | | 45 | | | | |

| gtt | aac | gta | aag | act | ggt | att | ttc | acc | ggc | cgt | tct | cct | aaa | gat | aaa | 192 |
|---|---|---|---|---|---|---|---|---|---|---|---|---|---|---|---|---|
| Val | Asn | Val | Lys | Thr | Gly | Ile | Phe | Thr | Gly | Arg | Ser | Pro | Lys | Asp | Lys | |
| | 50 | | | | | 55 | | | | | 60 | | | | | |

| ttc | atc | gtg | gat | gat | gaa | act | tcc | cat | gac | act | gta | tgg | tgg | gat | tcc | 240 |
|---|---|---|---|---|---|---|---|---|---|---|---|---|---|---|---|---|
| Phe | Ile | Val | Asp | Asp | Glu | Thr | Ser | His | Asp | Thr | Val | Trp | Trp | Asp | Ser | |
| 65 | | | | | 70 | | | | | 75 | | | | | 80 | |

| gaa | gat | tat | cac | aac | gat | aac | cac | aga | gct | acg | ccg | gaa | acc | tgg | aac | 288 |
|---|---|---|---|---|---|---|---|---|---|---|---|---|---|---|---|---|
| Glu | Asp | Tyr | His | Asn | Asp | Asn | His | Arg | Ala | Thr | Pro | Glu | Thr | Trp | Asn | |
| | | | | 85 | | | | | 90 | | | | | 95 | | |

| gct | ctg | aaa | gaa | atc | gct | aaa | aag | gaa | ctg | tcc | aac | aag | aaa | ctc | tac | 336 |
|---|---|---|---|---|---|---|---|---|---|---|---|---|---|---|---|---|
| Ala | Leu | Lys | Glu | Ile | Ala | Lys | Lys | Glu | Leu | Ser | Asn | Lys | Lys | Leu | Tyr | |
| | | | 100 | | | | | 105 | | | | | 110 | | | |

| gtt | gta | gat | gct | ttc | tgc | ggt | gcc | aac | aaa | gac | acc | cgc | atg | gct | gtc | 384 |
|---|---|---|---|---|---|---|---|---|---|---|---|---|---|---|---|---|
| Val | Val | Asp | Ala | Phe | Cys | Gly | Ala | Asn | Lys | Asp | Thr | Arg | Met | Ala | Val | |
| | | 115 | | | | | 120 | | | | | 125 | | | | |

| cgc | ttc | atc | gta | gaa | gtt | gct | tgg | cag | gca | cat | ttc | gta | acg | aat | atg | 432 |
|---|---|---|---|---|---|---|---|---|---|---|---|---|---|---|---|---|
| Arg | Phe | Ile | Val | Glu | Val | Ala | Trp | Gln | Ala | His | Phe | Val | Thr | Asn | Met | |
| | 130 | | | | | 135 | | | | | 140 | | | | | |

| ttc | atc | cag | ccg | acg | gaa | gaa | gag | ctg | gct | aac | ttc | aag | ccg | gac | ttc | 480 |
|---|---|---|---|---|---|---|---|---|---|---|---|---|---|---|---|---|
| Phe | Ile | Gln | Pro | Thr | Glu | Glu | Glu | Leu | Ala | Asn | Phe | Lys | Pro | Asp | Phe | |
| 145 | | | | | 150 | | | | | 155 | | | | | 160 | |

| gta | gtt | tac | aac | gct | tcc | aag | gct | aaa | gtt | gaa | aac | tac | aag | gaa | ctt | 528 |
|---|---|---|---|---|---|---|---|---|---|---|---|---|---|---|---|---|
| Val | Val | Tyr | Asn | Ala | Ser | Lys | Ala | Lys | Val | Glu | Asn | Tyr | Lys | Glu | Leu | |
| | | | | 165 | | | | | 170 | | | | | 175 | | |

| ggt | ctc | cat | tcc | gaa | acg | gca | gta | gta | ttt | aac | ctc | acg | agc | cgc | gaa | 576 |
|---|---|---|---|---|---|---|---|---|---|---|---|---|---|---|---|---|
| Gly | Leu | His | Ser | Glu | Thr | Ala | Val | Val | Phe | Asn | Leu | Thr | Ser | Arg | Glu | |
| | | | 180 | | | | | 185 | | | | | 190 | | | |

| cag | gtt | atc | atc | aac | acc | tgg | tac | ggc | ggt | gaa | atg | aag | aag | ggt | atg | 624 |
|---|---|---|---|---|---|---|---|---|---|---|---|---|---|---|---|---|
| Gln | Val | Ile | Ile | Asn | Thr | Trp | Tyr | Gly | Gly | Glu | Met | Lys | Lys | Gly | Met | |
| | | 195 | | | | | 200 | | | | | 205 | | | | |

| | | | | | | | | | | | | | | | | |
|---|---|---|---|---|---|---|---|---|---|---|---|---|---|---|---|---|
| ttt | tcc | atg | atg | aac | tac | ttc | ctg | ccg | ctc | aag | ggg | att | gct | gct | atg | 672 |
| Phe | Ser | Met | Met | Asn | Tyr | Phe | Leu | Pro | Leu | Lys | Gly | Ile | Ala | Ala | Met | |
| | 210 | | | | 215 | | | | | 220 | | | | | | |
| cat | tgc | tcc | gct | aat | acg | gac | aag | cag | ggc | cag | aac | acg | gct | atc | ttc | 720 |
| His | Cys | Ser | Ala | Asn | Thr | Asp | Lys | Gln | Gly | Gln | Asn | Thr | Ala | Ile | Phe | |
| 225 | | | | | 230 | | | | | 235 | | | | | 240 | |
| ttc | ggc | ctc | tcc | ggc | acg | ggt | aaa | acc | acc | ctg | tcc | acg | gac | ccg | aaa | 768 |
| Phe | Gly | Leu | Ser | Gly | Thr | Gly | Lys | Thr | Thr | Leu | Ser | Thr | Asp | Pro | Lys | |
| | | | | 245 | | | | | 250 | | | | | 255 | | |
| cgt | ctc | ctg | att | ggt | gat | gat | gaa | cac | ggc | tgg | gat | gat | gaa | ggc | gta | 816 |
| Arg | Leu | Leu | Ile | Gly | Asp | Asp | Glu | His | Gly | Trp | Asp | Asp | Glu | Gly | Val | |
| | | | 260 | | | | | 265 | | | | | 270 | | | |
| ttc | aac | ttc | gaa | ggc | ggc | tgc | tat | gct | aag | gtt | atc | aac | ctc | gac | atg | 864 |
| Phe | Asn | Phe | Glu | Gly | Gly | Cys | Tyr | Ala | Lys | Val | Ile | Asn | Leu | Asp | Met | |
| | | 275 | | | | | 280 | | | | | 285 | | | | |
| gaa | tcc | gaa | ccg | gac | atc | tat | ggc | gcc | atc | aaa | cgt | aac | gct | ctg | ctc | 912 |
| Glu | Ser | Glu | Pro | Asp | Ile | Tyr | Gly | Ala | Ile | Lys | Arg | Asn | Ala | Leu | Leu | |
| | 290 | | | | | 295 | | | | | 300 | | | | | |
| gaa | aac | gtt | acc | ctc | gac | gac | aag | ggc | aac | atc | gac | ttt | gcc | gat | aag | 960 |
| Glu | Asn | Val | Thr | Leu | Asp | Asp | Lys | Gly | Asn | Ile | Asp | Phe | Ala | Asp | Lys | |
| 305 | | | | | 310 | | | | | 315 | | | | | 320 | |
| acc | atc | acg | gaa | aac | acc | cgt | gta | tcc | tat | cct | atc | gac | cac | atc | aaa | 1008 |
| Thr | Ile | Thr | Glu | Asn | Thr | Arg | Val | Ser | Tyr | Pro | Ile | Asp | His | Ile | Lys | |
| | | | | 325 | | | | | 330 | | | | | 335 | | |
| ggc | acc | gtt | aag | ggc | ttt | gtt | aac | gac | aag | agc | gca | gct | ccg | gca | gct | 1056 |
| Gly | Thr | Val | Lys | Gly | Phe | Val | Asn | Asp | Lys | Ser | Ala | Ala | Pro | Ala | Ala | |
| | | | 340 | | | | | 345 | | | | | 350 | | | |
| aag | agt | gtt | atc | ttc | ctg | tcc | gct | gat | gct | ttc | ggc | gta | ctg | ccc | ccg | 1104 |
| Lys | Ser | Val | Ile | Phe | Leu | Ser | Ala | Asp | Ala | Phe | Gly | Val | Leu | Pro | Pro | |
| | | 355 | | | | | 360 | | | | | 365 | | | | |
| gtt | tcc | atc | ctg | act | ccg | gaa | cag | acg | aag | tat | tac | ttc | ctc | tcc | ggc | 1152 |
| Val | Ser | Ile | Leu | Thr | Pro | Glu | Gln | Thr | Lys | Tyr | Tyr | Phe | Leu | Ser | Gly | |
| | 370 | | | | | 375 | | | | | 380 | | | | | |
| ttc | acg | gct | aaa | ctg | gct | ggt | acg | gaa | cgc | ggc | atc | acc | gaa | ccg | aca | 1200 |
| Phe | Thr | Ala | Lys | Leu | Ala | Gly | Thr | Glu | Arg | Gly | Ile | Thr | Glu | Pro | Thr | |
| 385 | | | | | 390 | | | | | 395 | | | | | 400 | |
| ccg | acc | ttc | tcc | gct | tgc | ttc | ggt | cag | gca | ttc | ctc | gaa | ctg | cat | ccg | 1248 |
| Pro | Thr | Phe | Ser | Ala | Cys | Phe | Gly | Gln | Ala | Phe | Leu | Glu | Leu | His | Pro | |
| | | | | 405 | | | | | 410 | | | | | 415 | | |
| acc | aag | tac | gca | gaa | gaa | ctc | gtt | aag | aag | atg | gag | gct | aac | ggc | acg | 1296 |
| Thr | Lys | Tyr | Ala | Glu | Glu | Leu | Val | Lys | Lys | Met | Glu | Ala | Asn | Gly | Thr | |
| | | | 420 | | | | | 425 | | | | | 430 | | | |
| aag | gca | tac | ctc | gtg | aac | acg | ggc | tgg | aat | ggt | tcc | ggc | aag | cgt | atc | 1344 |
| Lys | Ala | Tyr | Leu | Val | Asn | Thr | Gly | Trp | Asn | Gly | Ser | Gly | Lys | Arg | Ile | |
| | | 435 | | | | | 440 | | | | | 445 | | | | |
| tcc | atc | aaa | gat | acc | cgt | ggc | atc | atc | gat | gct | atc | cat | agc | ggc | gct | 1392 |
| Ser | Ile | Lys | Asp | Thr | Arg | Gly | Ile | Ile | Asp | Ala | Ile | His | Ser | Gly | Ala | |
| | 450 | | | | | 455 | | | | | 460 | | | | | |
| atc | aaa | aaa | gct | ccg | acc | aag | aag | att | ccg | ttc | ttc | aac | ctc | gaa | gta | 1440 |
| Ile | Lys | Lys | Ala | Pro | Thr | Lys | Lys | Ile | Pro | Phe | Phe | Asn | Leu | Glu | Val | |
| 465 | | | | | 470 | | | | | 475 | | | | | 480 | |
| ccg | acg | gaa | ctt | gag | ggc | gtt | gac | acc | aac | atc | ctc | gac | ccg | aag | gat | 1488 |
| Pro | Thr | Glu | Leu | Glu | Gly | Val | Asp | Thr | Asn | Ile | Leu | Asp | Pro | Lys | Asp | |
| | | | | 485 | | | | | 490 | | | | | 495 | | |
| acc | tat | gct | aac | ccg | gct | gat | tgg | gaa | gca | aaa | gca | aaa | gac | ctc | gct | 1536 |
| Thr | Tyr | Ala | Asn | Pro | Ala | Asp | Trp | Glu | Ala | Lys | Ala | Lys | Asp | Leu | Ala | |
| | | | 500 | | | | | 505 | | | | | 510 | | | |
| cag | cgc | ttc | atc | aag | aac | ttc | gac | aaa | tac | acg | aag | aac | aat | gaa | gct | 1584 |
| Gln | Arg | Phe | Ile | Lys | Asn | Phe | Asp | Lys | Tyr | Thr | Lys | Asn | Asn | Glu | Ala | |
| | | 515 | | | | | 520 | | | | | 525 | | | | |

```
ggt aag gct ctc gtt gcc gct ggt ccg cag ctc taa                1620
Gly Lys Ala Leu Val Ala Ala Gly Pro Gln Leu
    530             535

<210> SEQ ID NO 65
<211> LENGTH: 539
<212> TYPE: PRT
<213> ORGANISM: Selenomonas ruminantium

<400> SEQUENCE: 65

Met Ala Asn Ile Asp Leu Ser Gln Tyr Gly Ile Thr Gly Thr Thr Gly
1               5                   10                  15

Ile Leu His Asn Pro Ser Tyr Lys Thr Leu Phe Glu Glu Thr Lys
            20                  25                  30

Glu Gly Leu Thr Gly Tyr Glu Gln Gly Gln Val Ser Glu Leu Gly Ala
        35                  40                  45

Val Asn Val Lys Thr Gly Ile Phe Thr Gly Arg Ser Pro Lys Asp Lys
    50                  55                  60

Phe Ile Val Asp Asp Glu Thr Ser His Asp Thr Val Trp Trp Asp Ser
65                  70                  75                  80

Glu Asp Tyr His Asn Asp Asn His Arg Ala Thr Pro Glu Thr Trp Asn
                85                  90                  95

Ala Leu Lys Glu Ile Ala Lys Lys Glu Leu Ser Asn Lys Lys Leu Tyr
            100                 105                 110

Val Val Asp Ala Phe Cys Gly Ala Asn Lys Asp Thr Arg Met Ala Val
        115                 120                 125

Arg Phe Ile Val Glu Val Ala Trp Gln Ala His Phe Val Thr Asn Met
    130                 135                 140

Phe Ile Gln Pro Thr Glu Glu Leu Ala Asn Phe Lys Pro Asp Phe
145                 150                 155                 160

Val Val Tyr Asn Ala Ser Lys Ala Lys Val Glu Asn Tyr Lys Glu Leu
                165                 170                 175

Gly Leu His Ser Glu Thr Ala Val Val Phe Asn Leu Thr Ser Arg Glu
            180                 185                 190

Gln Val Ile Ile Asn Thr Trp Tyr Gly Gly Glu Met Lys Lys Gly Met
        195                 200                 205

Phe Ser Met Met Asn Tyr Phe Leu Pro Leu Lys Gly Ile Ala Ala Met
    210                 215                 220

His Cys Ser Ala Asn Thr Asp Lys Gln Gly Gln Asn Thr Ala Ile Phe
225                 230                 235                 240

Phe Gly Leu Ser Gly Thr Gly Lys Thr Thr Leu Ser Thr Asp Pro Lys
                245                 250                 255

Arg Leu Leu Ile Gly Asp Asp Glu His Gly Trp Asp Asp Glu Gly Val
            260                 265                 270

Phe Asn Phe Glu Gly Gly Cys Tyr Ala Lys Val Ile Asn Leu Asp Met
        275                 280                 285

Glu Ser Glu Pro Asp Ile Tyr Gly Ala Ile Lys Arg Asn Ala Leu Leu
    290                 295                 300

Glu Asn Val Thr Leu Asp Asp Lys Gly Asn Ile Asp Phe Ala Asp Lys
305                 310                 315                 320

Thr Ile Thr Glu Asn Thr Arg Val Ser Tyr Pro Ile Asp His Ile Lys
                325                 330                 335
```

```
Gly Thr Val Lys Gly Phe Val Asn Asp Lys Ser Ala Ala Pro Ala Ala
                340             345                 350

Lys Ser Val Ile Phe Leu Ser Ala Asp Ala Phe Gly Val Leu Pro Pro
            355                 360                 365

Val Ser Ile Leu Thr Pro Glu Gln Thr Lys Tyr Tyr Phe Leu Ser Gly
    370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Gln Ala Phe Leu Glu Leu His Pro
                405                 410                 415

Thr Lys Tyr Ala Glu Glu Leu Val Lys Lys Met Glu Ala Asn Gly Thr
                420                 425                 430

Lys Ala Tyr Leu Val Asn Thr Gly Trp Asn Gly Ser Gly Lys Arg Ile
            435                 440                 445

Ser Ile Lys Asp Thr Arg Gly Ile Ile Asp Ala Ile His Ser Gly Ala
    450                 455                 460

Ile Lys Lys Ala Pro Thr Lys Lys Ile Pro Phe Phe Asn Leu Glu Val
465                 470                 475                 480

Pro Thr Glu Leu Glu Gly Val Asp Thr Asn Ile Leu Asp Pro Lys Asp
                485                 490                 495

Thr Tyr Ala Asn Pro Ala Asp Trp Glu Ala Lys Ala Lys Asp Leu Ala
                500                 505                 510

Gln Arg Phe Ile Lys Asn Phe Asp Lys Tyr Thr Lys Asn Asn Glu Ala
                515                 520                 525

Gly Lys Ala Leu Val Ala Ala Gly Pro Gln Leu
530                 535
```

<210> SEQ ID NO 66
<211> LENGTH: 37
<212> TYPE: DNA
<213> ORGANISM: Artificial Sequence
<220> FEATURE:
<223> OTHER INFORMATION: primer

<400> SEQUENCE: 66
catggcggcc gcttatttga tttcaattt gtcccac      37

<210> SEQ ID NO 67
<211> LENGTH: 51
<212> TYPE: DNA
<213> ORGANISM: Artificial Sequence
<220> FEATURE:
<223> OTHER INFORMATION: primer

<400> SEQUENCE: 67
gatcccgatc gaaggaggtt ataaaaaatg gaattgaatt cgtgtaattg c      51